United States Patent
Smaill et al.

(10) Patent No.: US 9,101,632 B2
(45) Date of Patent: Aug. 11, 2015

(54) KINASE INHIBITORS, PRODRUG FORMS THEREOF AND THEIR USE IN THERAPY

(75) Inventors: Jeffrey Bruce Smaill, Auckland (NZ); Adam Vorn Patterson, Auckland (NL); Guo-Liang Lu, Auckland (NZ); Ho Huat Lee, Auckland (NZ); Amir Ashoorzadeh, Auckland (NZ); Robert Forbes Anderson, Auckland (NZ); William Robert Wilson, Waiuku (NZ); William Alexander Denny, Manukau (NZ); Huai-Ling Annie Hsu, Auckland (NZ); Andrej Maroz, Auckland (NZ); Stephen Michael Frazer Jamieson, Auckland (NZ); Alexandra Marie Mowday, Auckland (NZ); Kendall Marie Carlin, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 119 days.

(21) Appl. No.: 13/390,398

(22) PCT Filed: Sep. 2, 2010

(86) PCT No.: PCT/NZ2010/000174
§ 371 (c)(1),
(2), (4) Date: Apr. 24, 2012

(87) PCT Pub. No.: WO2011/028135
PCT Pub. Date: Mar. 10, 2011

(65) Prior Publication Data
US 2012/0202832 A1 Aug. 9, 2012

(30) Foreign Application Priority Data
Sep. 2, 2009 (NZ) ........................ 579458

(51) Int. Cl.
A61K 31/519 (2006.01)
A61P 35/00 (2006.01)
C07D 471/04 (2006.01)

(52) U.S. Cl.
CPC ............ *A61K 31/519* (2013.01); *C07D 471/04* (2013.01)

(58) Field of Classification Search
None
See application file for complete search history.

(56) References Cited

FOREIGN PATENT DOCUMENTS

| JP | 2000-502988 | 3/2000 |
|---|---|---|
| JP | 2009-525956 | 7/2009 |
| WO | 97/07101 A1 | 2/1997 |
| WO | WO 97/38983 A1 | 10/1997 |
| WO | 99/09016 | 2/1999 |
| WO | WO 99/06378 A1 | 2/1999 |
| WO | WO 2004/091625 A1 | 10/2004 |
| WO | WO 2007/054551 A1 | 5/2007 |
| WO | 2007/082434 A1 | 7/2007 |
| WO | 2008/151253 A1 | 12/2008 |
| WO | WO 2010/104406 A1 | 9/2010 |
| WO | WO 2010104406 A1 * | 9/2010 |

OTHER PUBLICATIONS

Klutchko, Tyrosine Kinase Inhibitors. 19. 6-Alkynamides of 4-Anilinoquinazolines and 4-Anilinopyrido[3,4-d]pyrimidines as Irreversible Inhibitors of the erbB Family of Tyrosine Kinase Receptors, J. Med. Chem., 2006, 49, pp. 1475-1485.*

Simone, Oncology: Introduction, Cecil Textbook of Medicine, 20th Edition, 1996 vol. 1, pp. 1004-1010.*

Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.*

Tercel, M., et al; "Hypoxia-Selective Antitumor Agents. 16. Nitroarylmethyl Quaternary Salts as Bioreductive Prodrugs of the Alkylating Agent Mechlorethamine"; *J. Med. Chem*.; vol. 44, No. 21, pp. 3511-3522 (2001).

Tercel, M., et al; "Nitrobenzyl Mustard Quaternary Salts: A New Class of Hypoxia-Selective Cytotoxins Showing Very High in Vitro Selectivity"; *J. Med. Chem*.; vol. 36, No. 17, pp. 2578-2579 (1993).

Denny, W.A., et al; "Nitrobenzyl Mustard Quaternary Salts: A New Class of Hypoxia-Selective Cytotoxins Capable of Releasing Diffusible Cytotoxins on Bioreduction"; *Int. J. Radiation Oncology Biol. Phys*.; vol. 29, No. 2, pp. 317-321 (1994).

Tercel, M., et al; "Hypoxia-Selective Antitumor Agents. 12. Nitrobenzyl Quaternary Salts as Bioreductive Prodrugs of the Alkylating Agent Mechlorethamine"; *J. Med. Chem.*; vol. 39, No. 5, pp. 1084-1094 (1996).

Anderson, R.F., et al; "Pulse Radiolysis Studies on the Fragmentation of Arylmethyl Quaternary Nitrogen Mustards by One-Electron Reduction in Aqueous Solution"; *J. Phys. Chem. A.*; vol. 101, No. 50, pp. 9704-9709 (1997).

Wilson, W.R., et al; "Reduction of Nitroarylmethyl Quaternary Ammonium Prodrugs of Mechlorethamine by Radiation"; *Radiation Research*; vol. 149, No. 3; pp. 237-245 (1998).

Wilson, W.R., et al; "Radiation-activated prodrugs as hypoxia-selective cytotoxins: model studies with nitroarylmethyl quaternary salts"; *Anti-Cancer Drug Design*; vol. 13, No. 6, pp. 663-685 (1998).

Kriste, A.G., et al; "Pathways of Reductive Fragmentation of Heterocyclic Nitroarylmethyl Quaternary Ammonlium Prodrugs of Mechlorethamine"; *Radiation Research*; vol. 158, No. 6, pp. 753-762 (2002).

Wissner, A., et al; "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)"; *J. Med. Chem.*; vol. 46, pp. 49-63 (2003).

\* cited by examiner

*Primary Examiner* — Melenie McCormick
*Assistant Examiner* — Andrew Lee
(74) *Attorney, Agent, or Firm* — Kilpatrick Townsend & Stockton LLP

(57) ABSTRACT

The invention provides kinase inhibitors of Formula I:

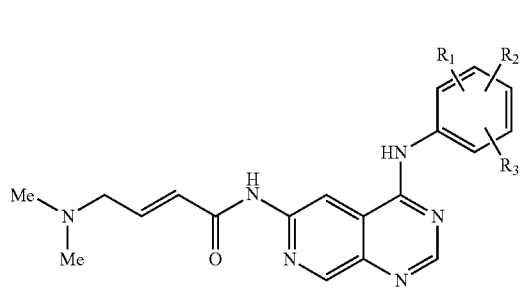

I wherein either:

(1) $R_1$ is H, and
  (a) $R_2$ is (3-chlorobenzyl)oxy-and $R_3$ is chloro;
  (b) $R_2$ and $R_3$, together with the carbon atoms to which they are attached, form 1-(3-fluorobenzyl)-1H-pyrazole;
  (c) $R_2$ is 2-pyridinylmethoxy and $R_3$ is chloro;
  (d) $R_2$ and $R_3$ are both chloro;
  (e) $R_2$ is chloro and $R_1$ is bromo;
  (f) $R_2$ and $R_3$ are both bromo;
  (g) $R_2$ is fluoro and $R_3$ is ethynyl;
  (h) $R_2$ is chloro and $R_3$ is ethynyl;
  (i) $R_2$ is bromo and $R_3$ is ethynyl;
  (j) other than when $R_1$ is in the 3-position in combination with $R_3$, in the 4-position, $R_2$ is bromo and $R_3$ is fluoro;
  (k) $R_2$ is 2-pyridinylmethoxy and $R_3$ is fluoro; or
  (l) $R_2$ is 2-pyridinylmethoxy and $R_1$ is bromo; or (2) at least one of $R_1$, $R_2$ and $R_3$ is selected from benzyloxy, 3-chlorobenzyloxy and 2-pyridinylmethoxy and when at least one of $R_1$, $R_2$ and $R_3$ is not benzyloxy, 3-chlorobenzyloxy or 2-pyridinylmethoxy, each of the others is independently selected from H, halogen, and $C_2$-$C_4$ alkynyl, with the proviso that when one of $R_1$, $R_2$ and $R_3$ is benzyloxy or 2-pyridinylmethoxy, the other two of $R_1$, $R_2$ and $R_3$ are not H; or (3) two of $R_1$, $R_2$ and $R_3$, together with the carbon atoms to which they are attached, form 1-(3-fluorobenzyl)-1H-pyrazole; and the other is selected from H, halogen and $C_2$-$C_4$ alkynyl.

Also provided are reductive prodrugs, comprising a kinase inhibitor as defined above and a reductive trigger linked directly or indirectly to a nitrogen of the kinase inhibitor. Further provided are pharmaceutical compositions, comprising the kinase inhibitors or the prodrugs, and the use of such compositions in therapy, in particular for treating cancer.

17 Claims, 16 Drawing Sheets

KINASE INHIBITORS, PRODRUG FORMS THEREOF AND THEIR USE IN THERAPY

FIELD OF THE INVENTION

The present invention relates to kinase inhibitors, to kinase inhibitors in prodrug form, compositions and medicaments containing them, and processes for the preparation and use of such inhibitors, compositions and medicaments.

BACKGROUND OF THE INVENTION

Kinases represent a large family of enzymes that catalyse the phosphorylation of proteins, lipids and metabolites and play a central role in the regulation of a wide variety of cellular processes. Abnormal kinase activity has been related to a wide range of disorders, including cancers. This has led to the development of kinase inhibitors as therapeutic agents.

This invention generally relates to compounds having activity as kinase inhibitors, including their prodrug forms, as well as to the application of such compounds in therapy.

SUMMARY OF THE INVENTION

In a first aspect, the invention provides a kinase inhibitor of Formula I:

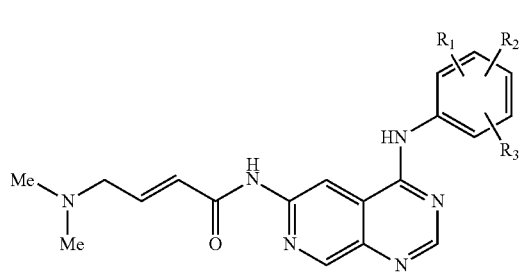

wherein either:
(1) $R_1$ is H, and
   (a) $R_1$ is (3-chlorobenzyl)oxy- and $R_3$ is chloro;
   (b) $R_2$ and $R_3$, together with the carbon atoms to which they are attached, form 1-(3-fluorobenzyl)-1H-pyrazole;
   (c) $R_1$ is 2-pyridinylmethoxy and $R_3$ is chloro;
   (d) $R_2$ and $R_3$ are both chloro;
   (e) $R_2$ is chloro and $R_3$ is bromo;
   (f) $R_2$ and $R_3$ are both bromo;
   (g) $R_2$ is fluoro and $R_3$ is ethynyl;
   (h) $R_2$ is chloro and $R_3$ is ethynyl;
   (i) $R_2$ is bromo and $R_3$ is ethynyl;
   (j) other than when $R_2$ is in the 3-position in combination with $R_3$ in the 4-position, $R_2$ is bromo and $R_3$ is fluoro;
   (k) $R_2$ is 2-pyridinylmethoxy and $R_3$ is fluoro; or
   (l) $R_2$ is 2-pyridinylmethoxy and $R_3$ is bromo; or
(2) at least one of $R_1$, $R_2$ and $R_3$ is selected from benzyloxy, 3-chlorobenzyloxy and 2-pyridinylmethoxy and when at least one of $R_1$, $R_2$ and $R_3$ is not benzyloxy, 3-chlorobenzyloxy or 2-pyridinylmethoxy, each of the others is independently selected from H, halogen, and $C_2$-$C_4$ alkynyl, with the proviso that when one of $R_1$, $R_2$ and $R_3$ is benzyloxy or 2-pyridinylmethoxy, the other two of $R_1$, $R_2$ and $R_3$ are not H; or (3) two of $R_1$, $R_2$ and $R_3$, together with the carbon atoms to which they are attached, form 1-(3-fluorobenzyl)-1H-pyrazole, and the other is selected from H, halogen and $C_2$-$C_4$ alkynyl;

or a pharmaceutically acceptable salt or solvate thereof.

In certain embodiments, the invention provides kinase inhibitors of the Formula IA

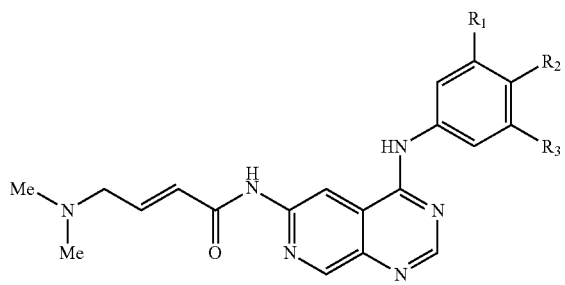

wherein $R_1$ is H, and either
   (a) $R_2$ is (3-chlorobenzyl)oxy- and $R_3$ is chloro;
   (b) $R_2$ and $R_3$, together with the carbon atoms to which they are attached, form 1-(3-fluorobenzyl)-1H-pyrazole;
   (c) $R_2$ is 2-pyridinylmethoxy and $R_3$ is chloro;
   (d) $R_2$ and $R_3$ are both chloro;
   (e) $R_2$ is chloro and $R_3$ is bromo;
   (f) $R_2$ is bromo and $R_3$ is chloro
   (g) $R_2$ and $R_3$ are both bromo;
   (h) $R_2$ is fluoro and $R_3$ is ethynyl;
   (i) $R_2$ is chloro and $R_3$ is ethynyl;
   (j) $R_2$ is bromo and $R_3$ is ethynyl;
   (k) $R_2$ is bromo and $R_3$ is fluoro;
   (l) $R_2$ is 2-pyridinylmethoxy and $R_3$ is fluoro; or
   (m) $R_2$ is 2-pyridinylmethoxy and $R_3$ is bromo;
and pharmaceutically acceptable salts and solvates thereof.

Preferably, the kinase inhibitor is selected from the following:
(2E)-N-(4-{3-chloro-4-[(3-chlorobenzyl)oxy]anilino}pyrido[3,4-d]pyrimidin-6-yl)-4-(dimethylamino)-2-butenamide (1),
(2E)-4-(dimethylamino)-N-(4-{[1-(3-fluorobenzyl)-1H-indazol-5-yl]amino}pyrido[3,4-d]pyrimidin-6-yl)-2-butenamide (2),
(2E)-N-{-[3-chloro-4-(2-pyridinylmethoxy)anilino]pyrido[3,4-d]pyrimidin-6-yl}-4-(dimethylamino)-2-butenamide (3),
(2E)-N-[4-(3,4-dichloroanilino)pyrido[3,4-d]pyrimidin-6-yl]-4-(dimethylamino)-2-butenamide (4),
(2E)-N-[4-(3-bromo-4-chloroanilino)pyrido[3,4-d]pyrimidin-6-yl]-4-(dimethylamino)-2-butenamide (5),
(2E)-N-[4-(4-bromo-3-chloroanilino)pyrido[3,4-d]pyrimidin-6-yl]-4-(dimethylamino)-2-butenamide (6),
(2E)-N-[4-(3,4-dibromoanilino)pyrido[3,4-d]pyrimidin-6-yl]-4-(dimethylamino)-2-butenamide (7),
(2E)-4-(dimethylamino)-N-[4-(3-ethynyl-4-fluoroanilino)pyrido[3,4-d]-pyrimidin-6-yl]-2-butenamide (8),
(2E)-N-[4-(4-chloro-3-ethynylanilino)pyrido[3,4-d]pyrimidin-6-yl]-4-(dimethylamino)-2-butenamide (9),
(2E)-N-[4-(4-bromo-3-ethynylanilino)pyrido[3,4-d]pyrimidin-6-yl]-4-(dimethylamino)-2-butenamide (10),
(2E)-N-[4-(4-bromo-3-fluoroanilino)pyrido[3,4-d]pyrimidin-6-yl]-4-(dimethylamino)-2-butenamide (11), (2E)-4-(dimethylamino)-N-{4-[3-fluoro-4-(2-pyridinyl-methoxy)anilino]pyrido[3,4-d]pyrimidin-6-yl}-2-butenamide (89) and
(2E)-N-{4-[3-bromo-4-(2-pyridinylmethoxy)anilino]pyrido[3,4-d]pyrimidin-6-yl}-4-(dimethylamino)-2-butenamide (90);
and pharmaceutically acceptable salts and hydrates thereof.
The structures of the compounds in the list above are below:
1
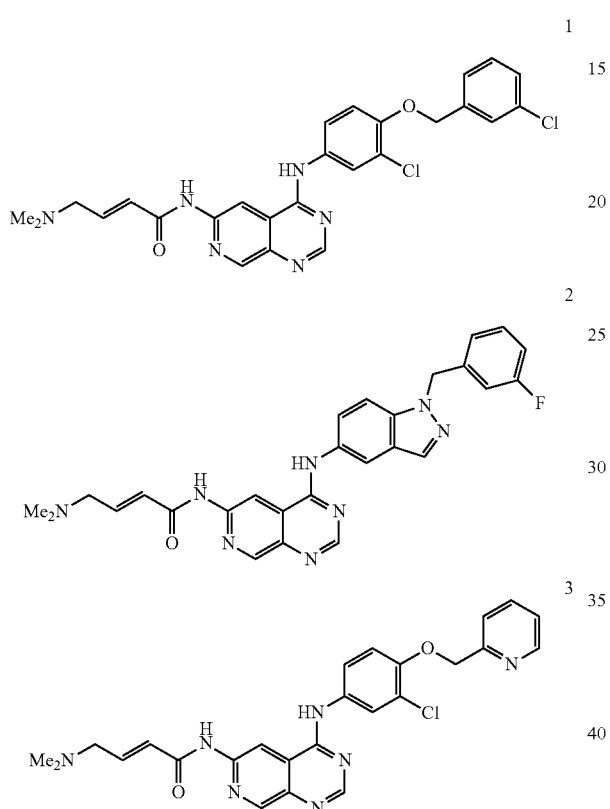
2
3
4
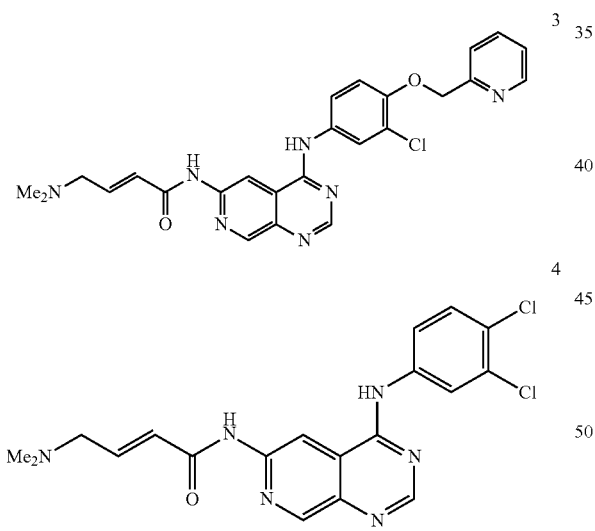
5
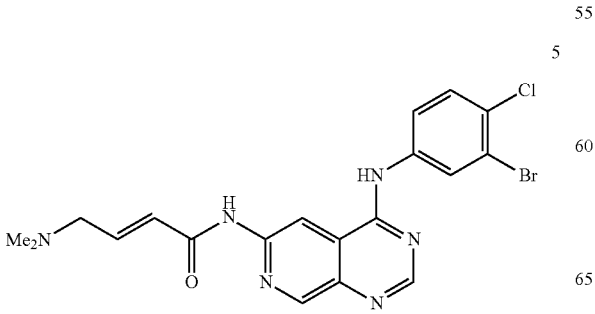
6
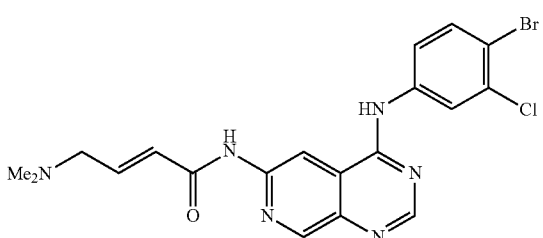
7
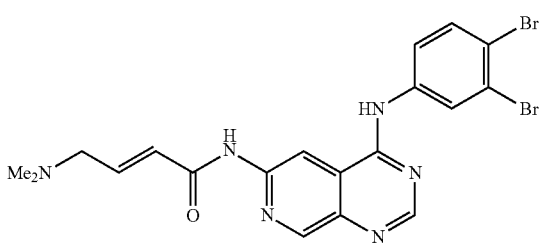
8
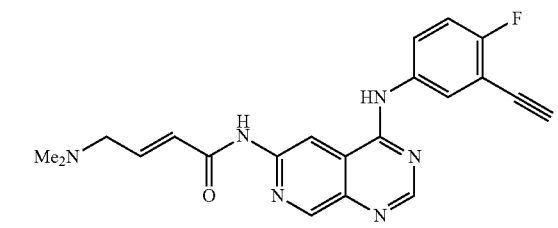
9
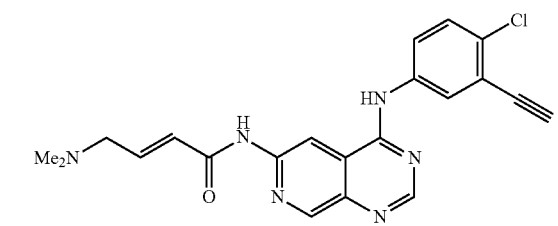
10
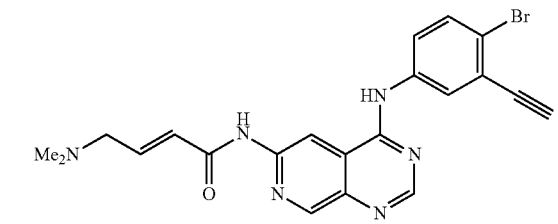
11
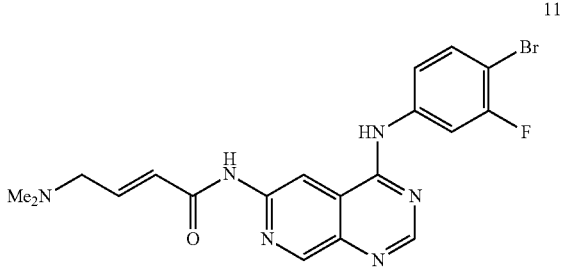

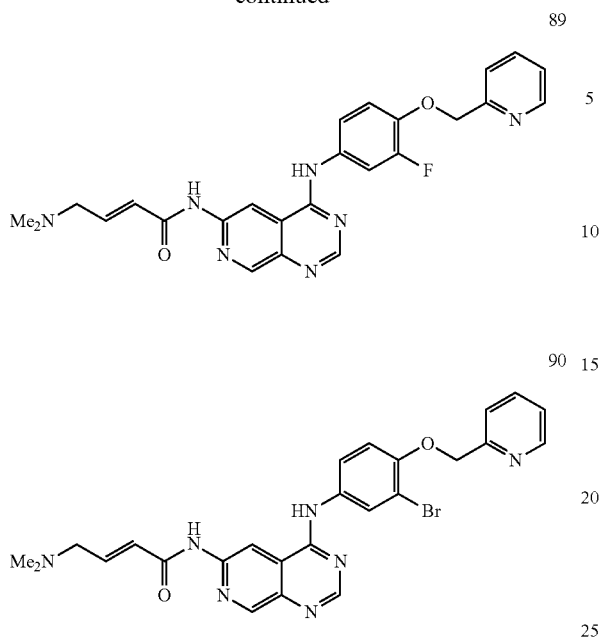

In another aspect, the invention provides the use of a kinase inhibitor of Formula I as defined above, or a salt or solvate thereof, in the preparation of a medicament.

In one preferred embodiment, the medicament is a prodrug and the compound of Formula I or the salt or solvate thereof is linked to a reductive trigger.

In yet a further aspect, the invention provides a reductive prodrug comprising a kinase inhibitor of Formula I as defined above, or a salt or solvate thereof, and a reductive trigger linked directly or indirectly to a nitrogen of the kinase inhibitor.

In certain embodiments, the reductive trigger is of Formula II:

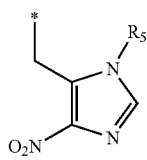

wherein * is a point of attachment to a nitrogen of said kinase inhibitor, and where in Formula II $R_5$ is selected from $C_1$-$C_6$ alkyl and $R_4$ is selected from H, methyl, ethyl, trifluoromethyl, —CN, —CONH$_2$ and propyn-1-yl.

In certain embodiments, the reductive trigger is selected from the group consisting of Formulae IIa to IIg:

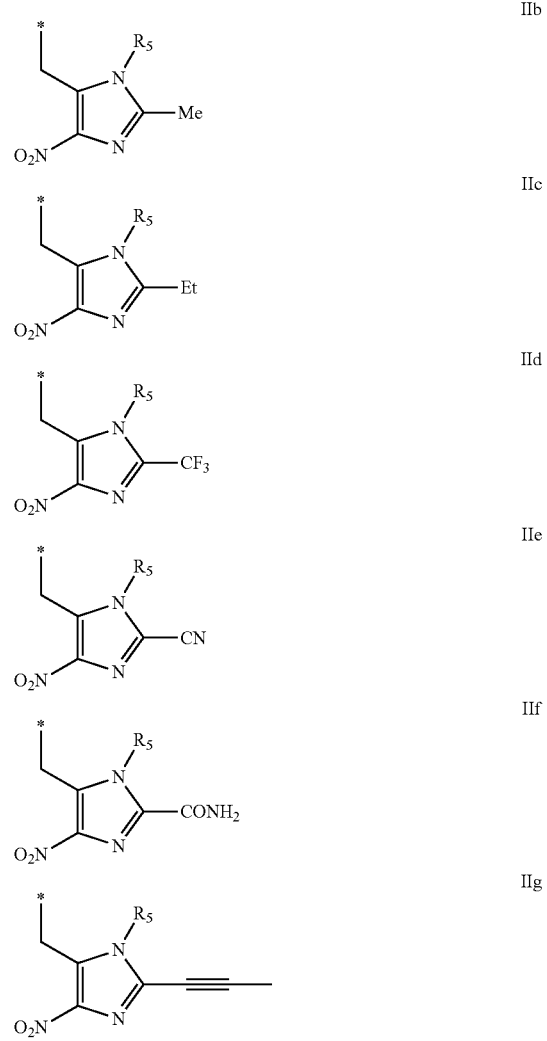

In certain embodiments, $R_5$ is selected from methyl, ethyl and propyl, preferably methyl.

In certain preferred embodiments, the reductive trigger is of Formula IIa, wherein $R_5$ is selected from methyl, ethyl and propyl.

Most preferably, the reductive trigger is of Formula IIa, wherein $R_5$ is selected from methyl.

In one embodiment, the prodrug is a compound of Formula III:

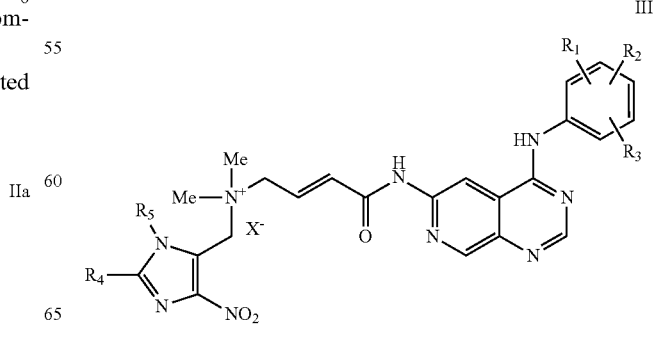

wherein X is any negatively charged counterion, $R_1$, $R_2$ and $R_3$ are as defined for Formula I, $R_4$ is selected from H, methyl, ethyl, trifluoromethyl, —CN, —CONH$_2$ and propyn-1-yl, and $R_5$ is $C_1$-$C_6$ alkyl.

In certain embodiments, the prodrug is a compound of Formula IIIA

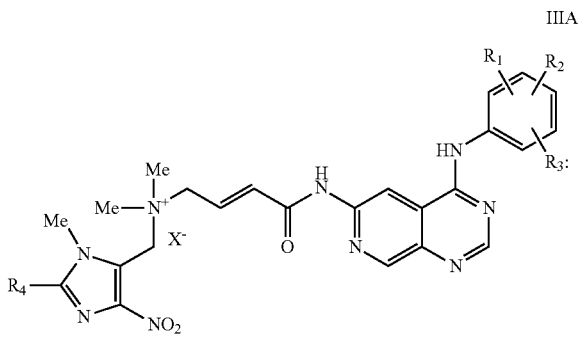

IIIA wherein X is any negatively charged counterion, $R_1$, $R_2$ and $R_3$ are as defined for Formula I and $R_4$ is selected from H, methyl, ethyl, trifluoromethyl, —CN, —CONH$_2$ and propyn-1-yl.

In yet another embodiment, the prodrug is a compound of Formula IIIB

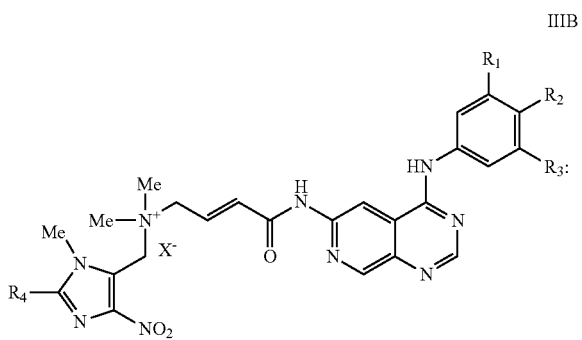

IIIB wherein X is any negatively charged counterion, $R_1$, $R_2$ and $R_3$ are as defined for Formula IA and $R_4$ is selected from H, methyl, ethyl, trifluoromethyl, —CN, —CONH$_2$ and propyn-1-yl.

In preferred embodiments, X is selected from halide (fluoride, chloride, bromide, iodide), methanesulfonate, trifluoromethanesulfonate, acetate, trifluoroacetate, tosylate, lactate, citrate and formate.

More preferably, X is halide, with bromide being most preferred.

Preferably, the compound of Formula III is selected from:
(2E)-4-[(4-{3-chloro-4-[(3-chlorobenzyl)oxy]anilino}pyrido[3,4-d]pyrimidin-6-yl)amino]-N,N-dimethyl-N-[(1-methyl-4-nitro-1H-imidazol-5-yl) methyl]-4-oxo-2-buten-1-ammonium bromide (12),
(2E)-4-[(4-{[1-(3-fluorobenzyl)-1H-indazol-5-yl]amino}pyrido[3,4-d]pyrimidin-6-yl)amino]N,N-dimethyl-N-[(1-methyl-4-nitro-1H-imidazol-5-yl)methyl]-4-oxo-2-buten-1-ammonium bromide (13),
(2E)-N-[(1,2-dimethyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (14),
(2E)-4-({4-[3-chloro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (15),
(2E)-4-{[4-(3,4-dichloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (16),
(2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl) methyl]-4-oxo-2-buten-1-ammonium bromide (17),
(2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (18),
(2E)-4-{[4-(3,4-dibromoanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (19),
(2E)-4-{[4-(3-ethynyl-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (20),
(2E)-4-{[4-(4-chloro-3-ethynylanilino) pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (21),
(2E)-4-[(4-{3-chloro-4-[(3-chlorobenzyl)oxy]anilino}pyrido[3,4-d]pyrimidin-6-yl)amino]-N-[(1,2-dimethyl-4-nitro-1H-imidazol-5-yl)methyl]-N,N-dimethyl-4-oxo-2-buten-1-ammonium bromide (22),
(2E)-4-[(4-{3-chloro-4-[(3-chlorobenzyl)oxy]anilino}pyrido[3,4-d]pyrimidin-6-yl)amino]-N-[(2-ethyl-1-methyl-4-nitro-1H-imidazol-5-yl)methyl]-N,N-dimethyl-4-oxo-2-buten-1-ammonium bromide (23),
(2E)-4-[(4-{3-chloro-4-[(3-chlorobenzyl)oxy]anilino}pyrido[3,4-d]pyrimidin-6-yl)amino]N,N-dimethyl-N-{[1-methyl-4-nitro-2-(trifluoro methyl)-1H-imidazol-5-yl]-methyl}-4-oxo-2-buten-1-ammonium bromide (24),
(2E)-4-[(4-{3-chloro-4-[(3-chlorobenzyl)oxy]anilino}pyrido[3,4-d]pyrimidin-6-yl)amino]-N-[(2-cyano-1-methyl-4-nitro-1H-imidazol-5-yl)methyl]-N,N-dimethyl-4-oxo-2-buten-1-ammonium bromide (25),
(2E)-N-{[2-(aminocarbonyl)-1-methyl-4-nitro-1H-imidazol-5-yl]methyl}-4-[(4-{3-chloro-4-[(3-chlorobenzyl)oxy]anilino}pyrido[3,4-d]pyrimidin-6-yl)amino]-N,N-dimethyl-4-oxo-2-buten-1-ammonium bromide (26),
(2E)-4-[(4-{3-chloro-4-[(3-chlorobenzyl) oxy]anilino}pyrido[3,4-d]pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide (27),
(2E)-N-[(2-ethyl-1-methyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]N,N-dimethyl-4-oxo-2-buten-1-ammonium bromide (28),
(2E)-4-[(4-{[1-(3-fluorobenzyl)-1H-indazol-5-yl]amino}pyrido[3,4-d]pyrimidin-6-yl)amino]-N,N-dimethyl-N-{[1-methyl-4-nitro-2-(trifluoromethyl)-1H-imidazol-5-yl]methyl}-4-oxo-2-buten-1-ammonium bromide (29),
(2E)-N-[(2-cyano-1-methyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (30), (2E)-N-{[2-(aminocarbonyl)-1-methyl-4-nitro-1H-imidazol-5-yl]methyl}-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (31), (2E)-4-[(4-{[1-(3-fluorobenzyl)-1H-indazol-5-yl]amino}pyrido[3,4-d]-pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide (32), (2E)-4-({4-[3-chloro-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide (33), (2E)-4-({-4-[3-chloro-4-(2-pyridinylmethoxy)anilino]pyrido[3,4-d]pyrimidin-6-yl}amino)-N-[(2-ethyl-1-methyl-4-nitro-1H-imidazol-5-yl)methyl]-N,N-dimethyl-4-oxo-2-buten-1-ammonium bromide (34), (2E)-4-({4-[3-chloro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (35), (2E)-4-({4-[3-chloro-4-(2-pyridinylmethoxy) anilino]pyrido[3,4-yl]pyrimidin-6-yl}amino)-N-[(2-cyano-1-methyl-4-nitro-1H-imidazol-5-yl) methyl]-N,N-dimethyl-4-oxo-2-buten-1-ammonium bromide (36), (2E)-N-{[2-(aminocarbonyl)-1-methyl-4-nitro-1H-imidazol-5-yl]methyl}-4-({4-[3-chloro-4-(2-pyridinylmethoxy)anilino]pyrido[3,4-d]pyrimidin-6-yl}amino)-N,N-dimethyl-4-oxo-2-buten-1-ammonium bromide (37), (2E)-4-({4-[3-chloro-4-(2-pyridinylmethoxy) anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (38), (2E)-4-{[4-(3,4-dichloroanilino) pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (39), (2E)-4-{[4-(3,4-dichloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (40), (2E)-4-{[4-(3,4-dichloroanilino)pyrido[3,4-d]pyrimidin-6-yl]amino}-N,N-dimethyl-N-{[1-methyl-4-nitro-2-(trifluoromethyl)-1,1-imidazol-5-yl]methyl}-4-oxo-2-buten-1-ammonium bromide (41), (2E)-N-[(2-cyano-1-methyl-4-nitro-1H-imidazol-5-yl)methyl]-4-{[4-(3,4-dichloroanilino) pyrido[3,4-d]pyrimidin-6-yl]amino}-N,N-dimethyl-4-oxo-2-buten-1-ammonium bromide (42), (2E)-N-{[2-(aminocarbonyl)-1-methyl-4-nitro-1H-imidazol-5-yl]methyl}-4-{[4-(3,4-dichloroanilino)pyrido[3,4-d]-pyrimidin-6-yl]amino}-N,N-dimethyl-4-oxo-2-buten-1-ammonium bromide (43), (2E)-4-{[4-(3,4-dichloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (44), (2E)-4-{[4-(3-bromo-4-chloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (45), (2E)-4-{[4-(3-bromo-4-chloroanilino)pyrido[3,4-a]pyrimidin-6-yl]amino}-N-[(2-ethyl-1-methyl-4-nitro-1H-imidazol-5-yl)methyl]-N,N-dimethyl-4-oxo-2-buten-1-ammonium bromide (46), (2E)-4-{[4-(3-bromo-4-chloroanilino)pyrido[3,4-d]pyrimidin-6-yl]amino}N,N-dimethyl-N-{[1-methyl-4-nitro-2-(trifluoromethyl)-1H-imidazol-5-yl]methyl}-4-oxo-2-buten-1-ammonium bromide (47), (2E)-4-{[4-(3-bromo-4-chloroanilino)pyrido[3,4-d]pyrimidin-6-yl]amino}cyano-1-methyl-4-nitro-1H-imidazol-5-yl)methyl]-N,N-dimethyl-4-oxo-2-buten-1-ammonium bromide (48), (2E)-N-{[2-(aminocarbonyl)-1-methyl-4-nitro-1H-imidazol-5-yl]methyl}-4-{[4-(3-bromo-4-chloroanilino)pyrido[3,4-d]pyrimidin-6-yl]amino}-N,N-dimethyl-4-oxo-2-buten-1-ammonium bromide (49), (2E)-4-{[4-(3-bromo-4-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (50), (2E)-4-{[4-(4-bromo-3-chloroanilino) pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (51), (2E)-4-{[4-(4-bromo-3-chloroanilino) pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (52), (2E)-4-{[4-(4-bromo-3-chloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (53), (2E)-4-{[4-(4-bromo-3-chloroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (54), (2E)-N-{[2-(aminocarbonyl)-1-methyl-4-nitro-1H-imidazol-5-yl]methyl}-4-{[4-(4-bromo-3-chloroanilino)pyrido[3,4-d]pyrimidin-6-yl]amino}-N,N-dimethyl-4-oxo-2-buten-1-ammonium bromide (55), (2E)-4-{[4-(4-bromo-3-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (56), (2E)-4-{[4-(3,4-dibromoanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (57), (2E)-4-{[4-(3,4-dibromoanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (58), (2E)-4-{[4-(3,4-dibromoanilino) pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (59), (2E)-N-[(2-cyano-1-methyl-4-nitro-1H-imidazol-5-yl)methyl]-4-{[4-(3,4-dibromoanilino)pyrido[3,4-d]pyrimidin-6-yl]amino}-N,N-dimethyl-4-oxo-2-buten-1-ammonium bromide (60), (2E)-N-{[2-(aminocarbonyl)-1-methyl-4-nitro-1H-imidazol-5-yl]methyl}-4-{[4-(3,4-dibromoanilino)pyrido[3,4-d]pyrimidin-6-yl]amino}-N,N-dimethyl-4-oxo-2-buten-1-ammonium bromide (61), (2E)-4-{[4-(3,4-dibromoanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (62), (2E)-N-[(1,2-dimethyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (63), (2E)-N-[(2-ethyl-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (64), (2E)-4-{[4-(3-ethynyl-4-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (65), (2E)-N-[(2-cyano-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (66), (2E)-N-{[2-(aminocarbonyl)-1-methyl-4-nitro-1H-imidazol-5-yl]methyl}-4-{[4-(3-ethynyl-4-fluoroanilino)pyrido[3,4-d]pyrimidin-6-yl]amino}-N,N-dimethyl-4-oxo-2-buten-1-ammonium bromide (67), (2E)-4-{[4-(3-ethynyl-4-fluoro anilino) pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (68), (2E)-4-{[4-(4-chloro-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (69), (2E)-4-{[4-(4-chloro-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (70), (2E)-4-{[4-(4-chloro-3-ethynylanilino)pyrido[3,4-a]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (71), (2E)-4-{[4-(4-chloro-3-ethynylanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (72), (2E)-N-{[2-(aminocarbonyl)-1-methyl-4-nitro-1H-imidazol-5-yl]methyl}-4-{[4-(4-chloro-3-ethynylanilino)pyrido[3,4-d]pyrimidin-6-yl]amino}-N,N-dimethyl-4-oxo-2-buten-1-ammonium bromide (73), (2E)-4-{[4-(4-chloro-3-ethynylanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (74), (2E)-4-{[4-(4-bromo-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (75), (2E)-4-{[4-(4-bromo-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (76), (2E)-4-{[4-(4-bromo-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (77), (2E)-4-{[4-(4-bromo-3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (78), (2E)-4-{[4-(4-bromo-3-ethynylanilino) pyrido[3,4-d]pyrimidin-6-yl]amino}-N-[(2-cyano-1-methyl-4-nitro-1H-imidazol-5-yl) methyl]-N,N-dimethyl-4-oxo-2-buten-1-ammonium bromide (79), (2E)-N-{[2-(aminocarbonyl)-1-methyl-4-nitro-1H-imidazol-5-yl]methyl}-4-{[4-(4-bromo-3-ethynylanilino)pyrido[3,4-d]pyrimidin-6-yl]amino}-N,N-dimethyl-4-oxo-2-buten-1-ammonium bromide (80), (2E)-4-{[4-(4-bromo-3-ethynylanilino)pyrido[3,4-d]-pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (81), (2E)-4-{[4-(4-bromo-3-fluoroanilino) pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (82), (2E)-4-{[4-(4-bromo-3-fluoroanilino) pyrido[3,4-d]-pyrimidin-6-yl]amino}-N-[(1,2-dimethyl-4-nitro-1H-imidazol-5-yl)methyl]-N,N-dimethyl-4-oxo-2-buten-1-ammonium bromide (83), (2E)-4-{[4-(4-bromo-3-fluoroanilino)pyrido[3,4-d]pyrimidin-6-yl]amino}-N-[(2-ethyl-1-methyl-4-nitro-1H-imidazol-5-yl) methyl]-N,N-dimethyl-4-oxo-2-buten-1-ammonium bromide (84), (2E)-4-{[4-(4-bromo-3-fluoroanilino)pyrido[3,4-d]-pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (85), (2E)-4-{[4-(4-bromo-3-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (86), (2E)-N-{[2-(aminocarbonyl)-1-methyl-4-nitro-1H-imidazol-5-yl]methyl}-4-{[4-(4-bromo-3-fluoroanilino)pyrido[3,4-d]pyrimidin-6-yl]amino}-N,N-dimethyl-4-oxo-2-buten-1-ammonium bromide (87), (2E)-4-{[4-(4-bromo-3-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (88), (2E)-4-({4-[3-fluoro-4-(2-pyridinylmethoxy) anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (91), (2E)-N-[(1,2-dimethyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide (92), (2E)-N-[(2-ethyl-1-methyl-4-nitro-1H-imidazol-5-yl)methyl]-4-({4-[3-fluoro-4-(2-pyridinylmethoxy) anilino]pyrido[3,4-d]pyrimidin-6-yl}amino)-N,N-dimethyl-4-oxo-2-buten-1-ammonium bromide (93), (2E)-4-({-4-[3-fluoro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (94), (2E)-N-[(2-cyano-1-methyl-4-nitro-1H-imidazol-5-yl)methyl]-4-({-4-[3-fluoro-4-(2-pyridinylmethoxy) anilino]pyrido[3,4-d]pyrimidin-6-yl}amino)-N,N-dimethyl-4-oxo-2-buten-1-ammonium bromide (95), (2E)-N-{[2-(aminocarbonyl)-1-methyl-4-nitro-1H-imidazol-5-yl]methyl}-4-({-4-[3-fluoro-4-(2-pyridinylmethoxy) anilino]pyrido[3,4-d]pyrimidin-6-yl}amino)-N,N-dimethyl-4-oxo-2-buten-1-ammonium bromide (96), (2E)-4-({-4-[3-fluoro-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (97), (2E)-4-({-4-[3-bromo-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (98), (2E)-4-({4-[3-bromo-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide (99), (2E)-4-({4-[3-bromo-4-(2-pyridinylmethoxy)anilino]pyrido[3,4-d]-pyrimidin-6-yl}amino)-N-[(2-ethyl-1-methyl-4-nitro-1H-imidazol-5-yl)methyl]-N,N-dimethyl-4-oxo-2-buten-1-ammonium bromide (100), (2E)-4-({-4-[3-bromo-4-(2-pyridinylmethoxy)anilino]pyrido[3,4-d]-pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (101), (2E)-4-({-4-[3-bromo-4-(2-pyridinylmethoxy)anilino]pyrido[3,4-d]pyrimidin-6-yl}amino)-N-[(2-cyano-1-methyl-4-nitro-1H-imidazol-5-yl)methyl]-N,N-dimethyl-4-oxo-2-buten-1-ammonium bromide (102), (2E)-N-{[2-(amino carbonyl)-1-methyl-4-nitro-1H-imidazol-5-yl]methyl}-4-({-4-[3-bromo-4-(2-pyridinylmethoxy)anilino]pyrido[3,4-d]pyrimidin-6-yl}amino)-N,N-dimethyl-4-oxo-2-buten-1-ammonium bromide (103) and (2E)-4-({4-[3-bromo-4-(2-pyridinylmethoxy)anilino]pyrido[3,4-d]-pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (104).

The structures of the prodrug compounds in the list above are below:

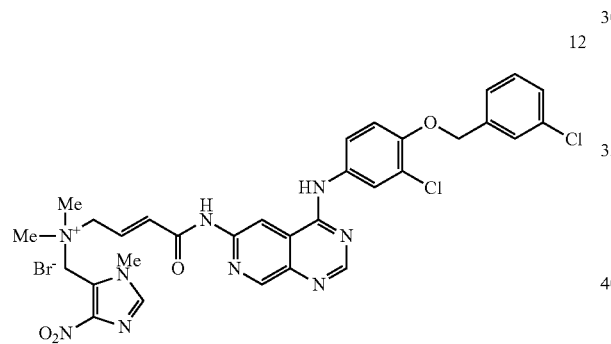

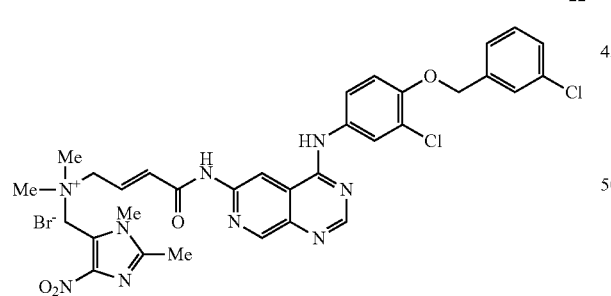

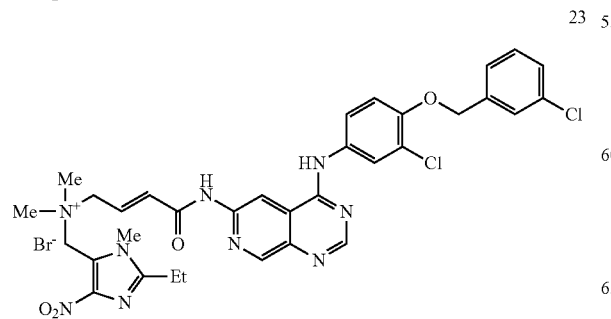

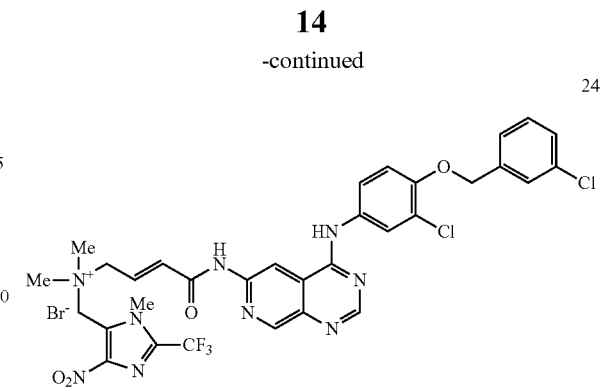

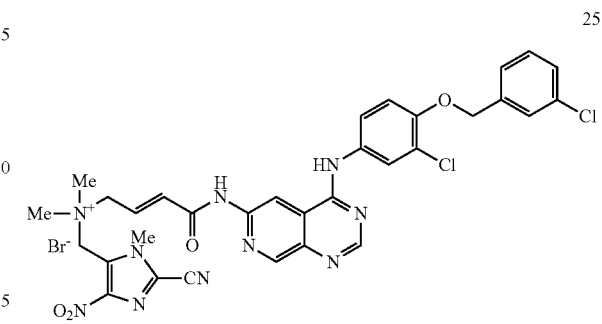

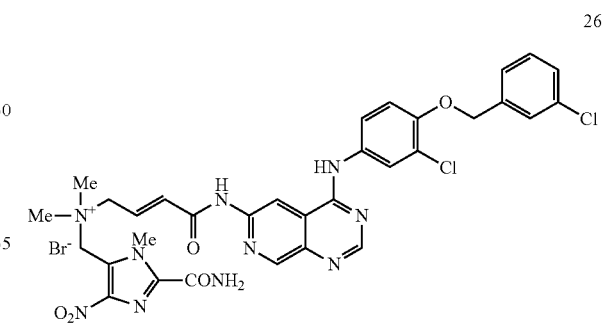

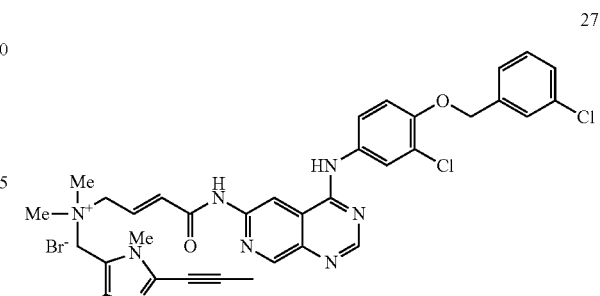

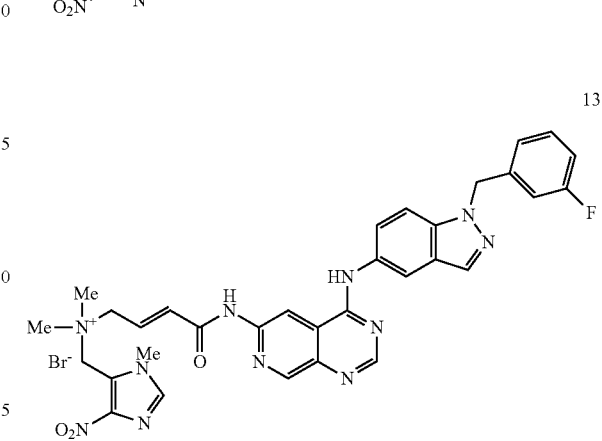

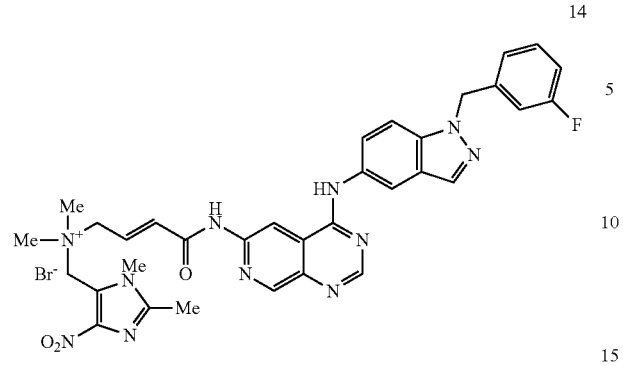
14
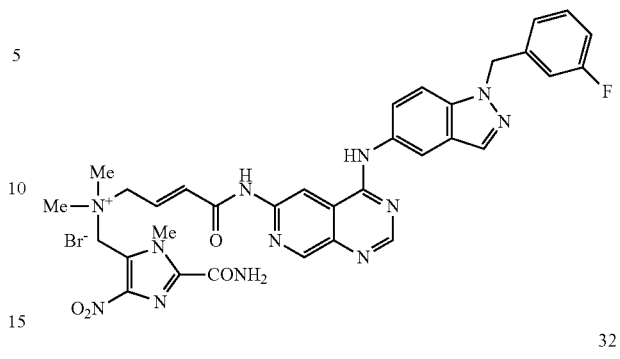
31
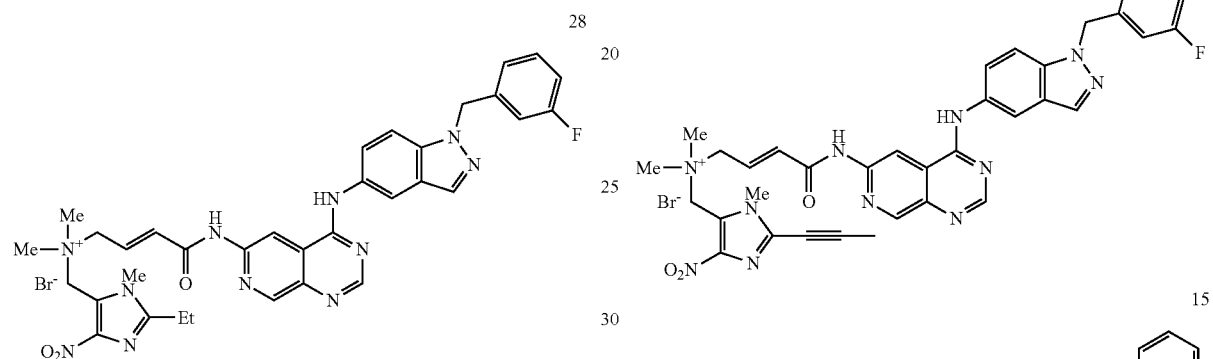
28
32
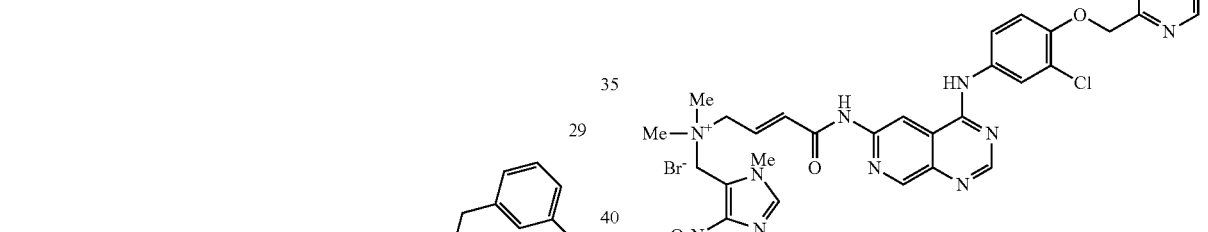
29
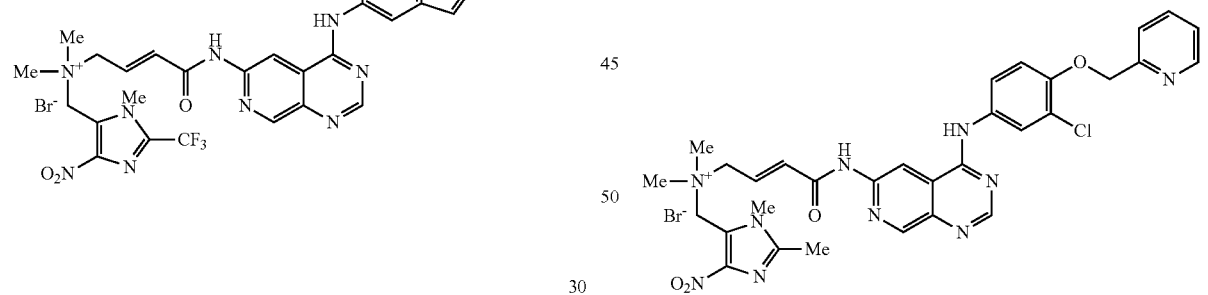
15
30
33
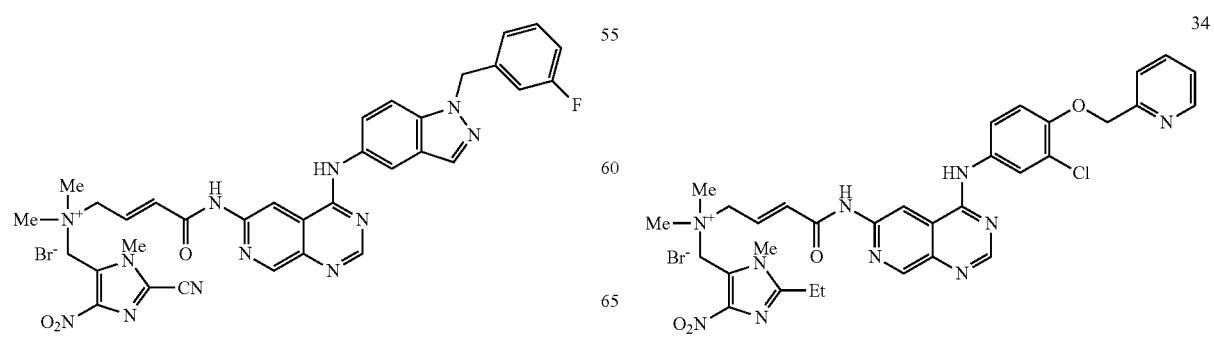
34

35
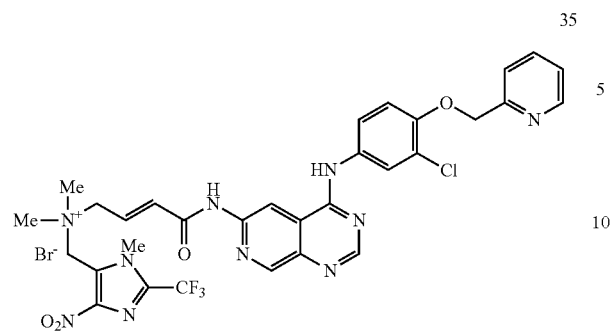
36
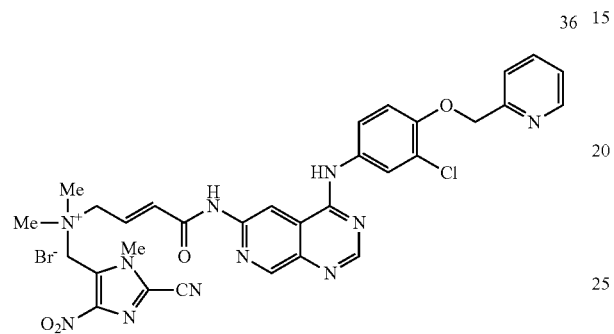
37
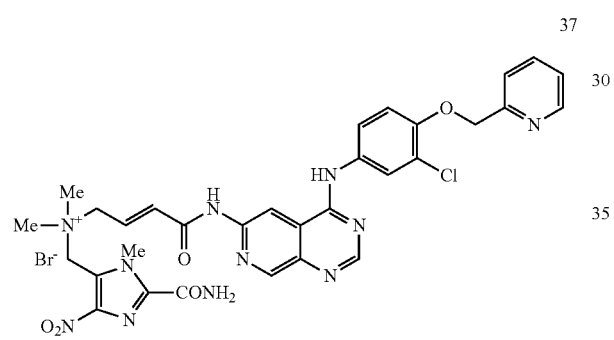
38
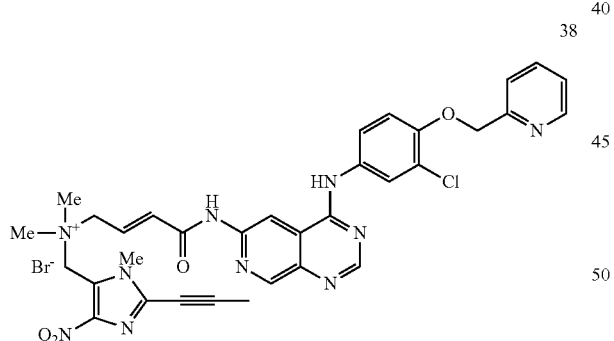
16
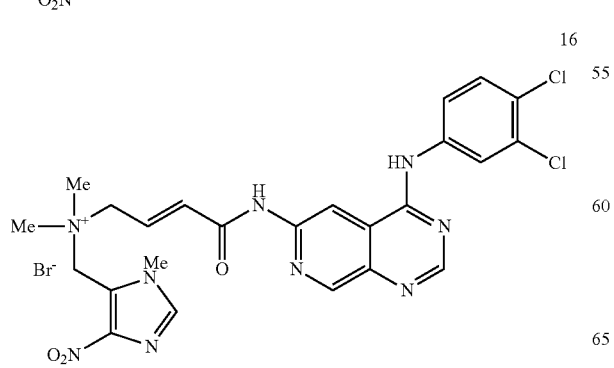
39
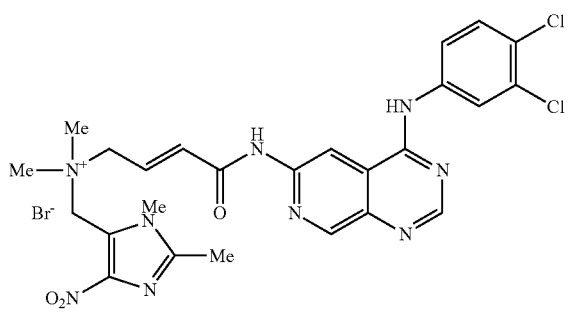
40
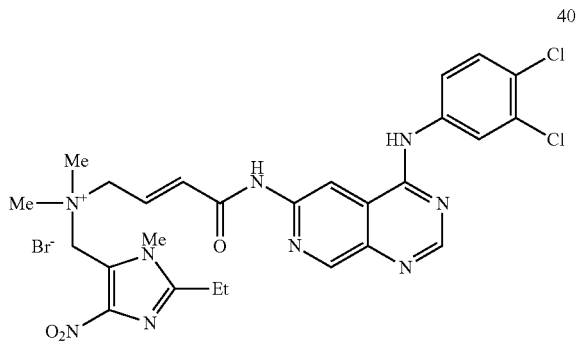
41
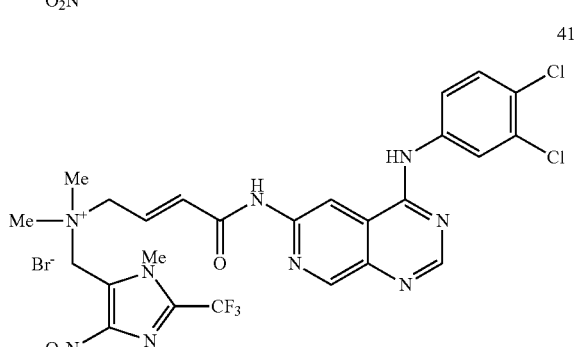
42
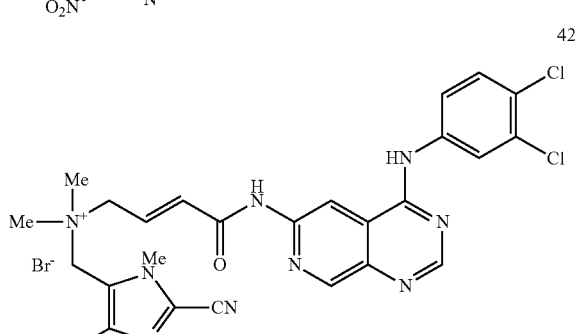
43
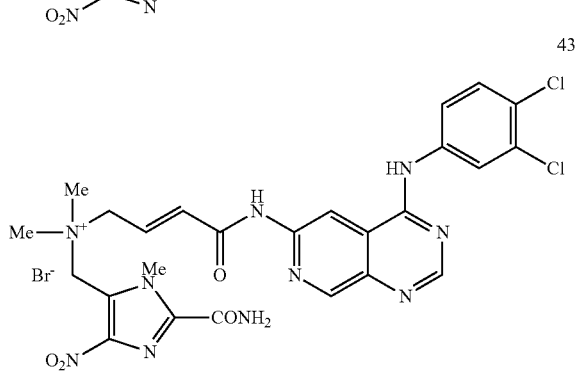

44
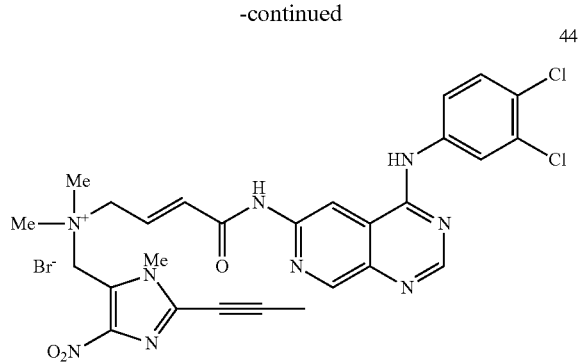
17
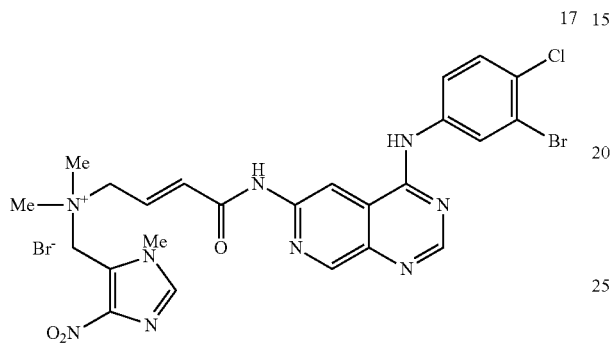
45
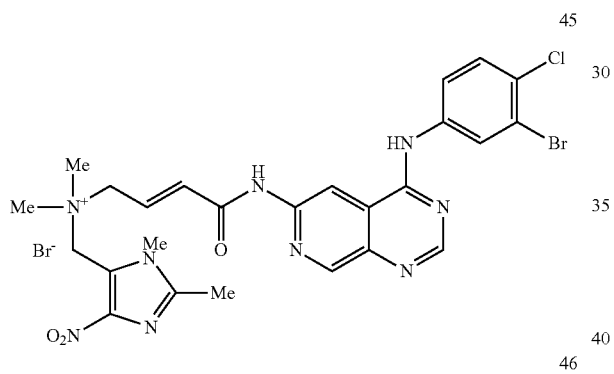
46
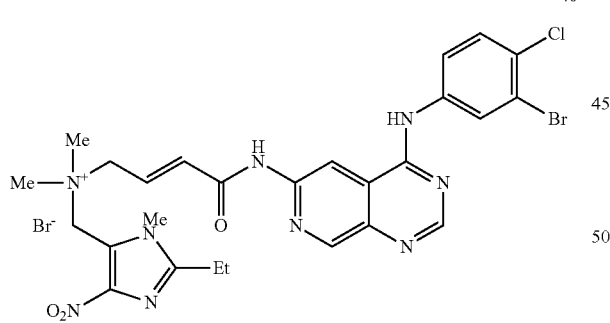
47
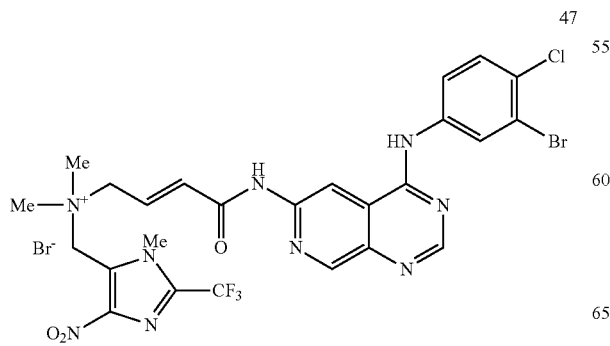
48
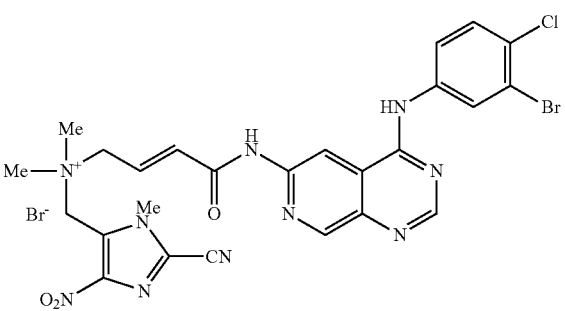
49
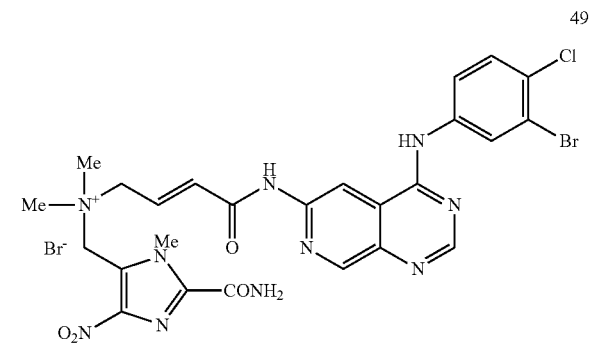
50
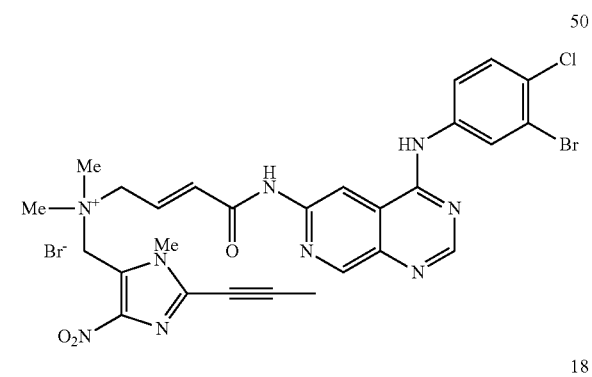
18
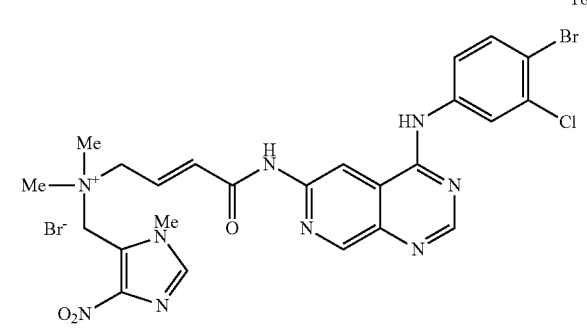
51
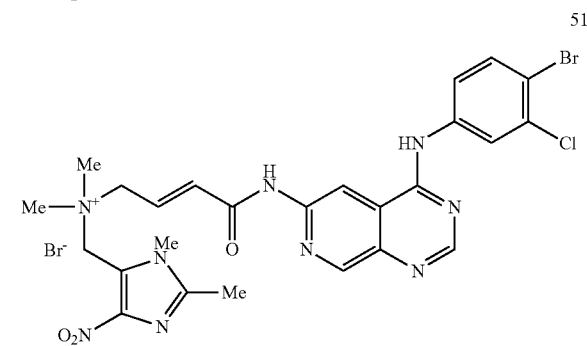

52
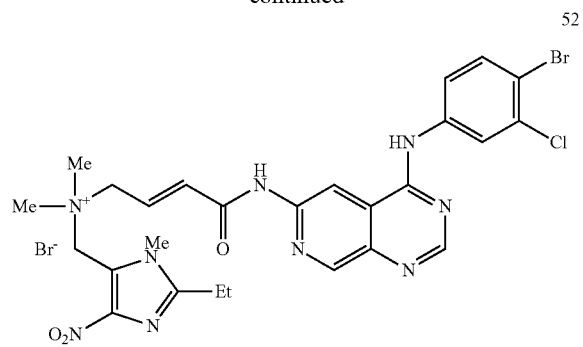
53
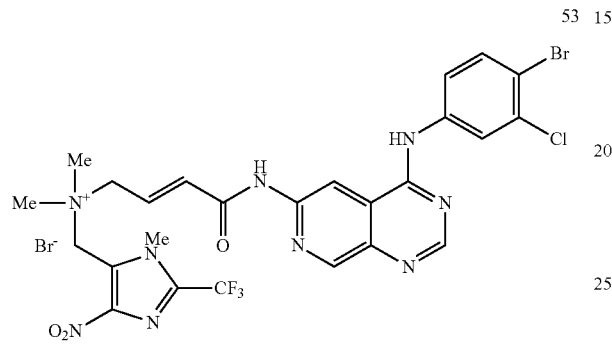
54
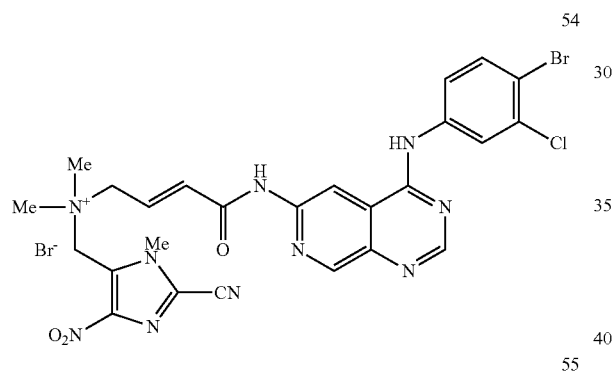
55
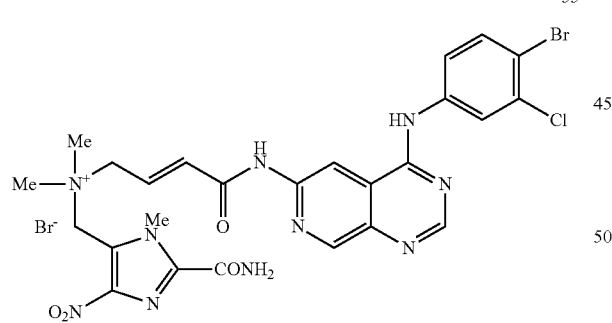
56
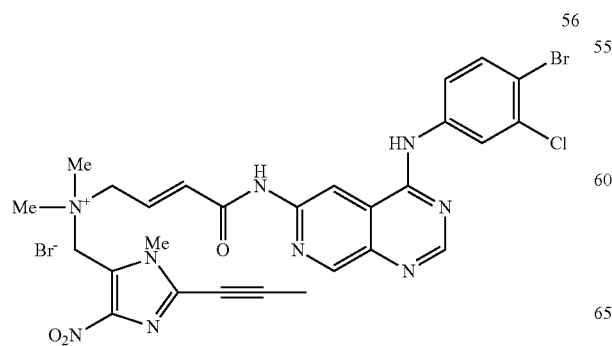
19
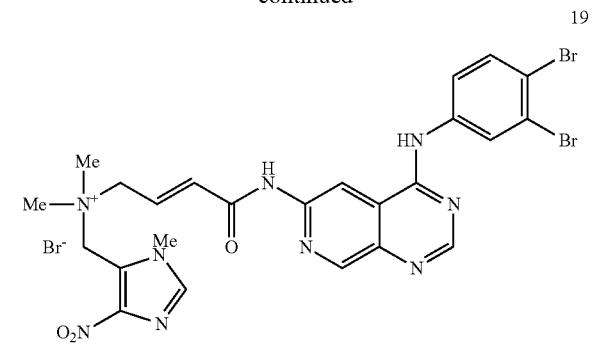
57
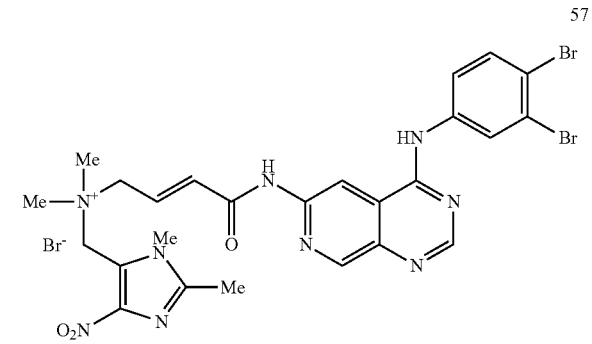
58
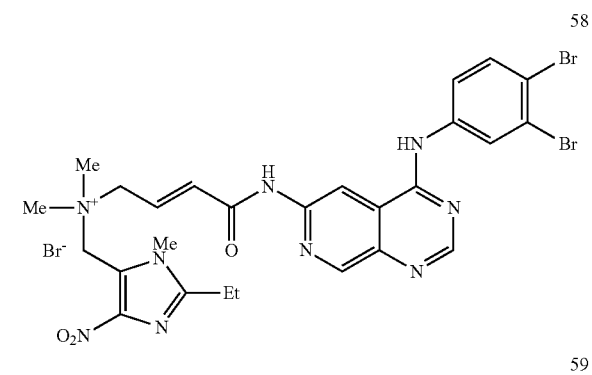
59
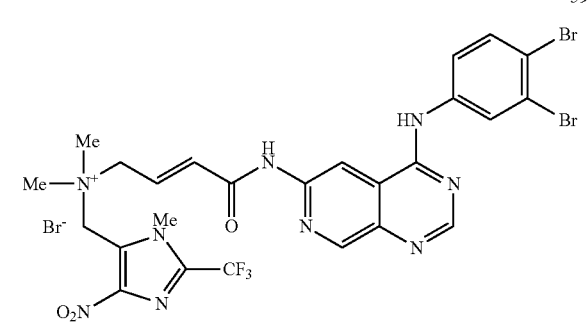
60
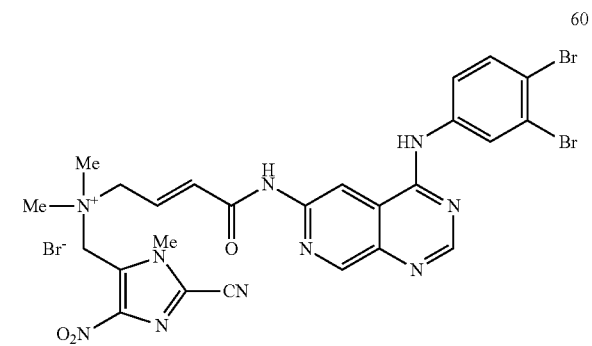

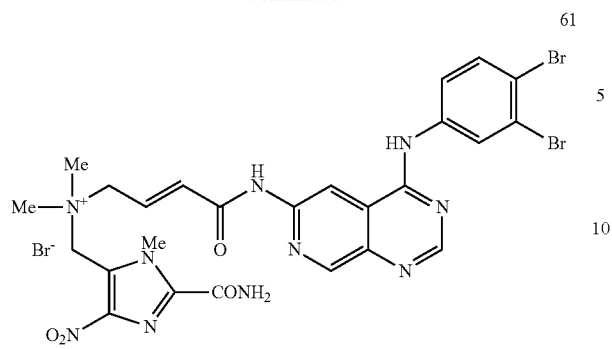
61
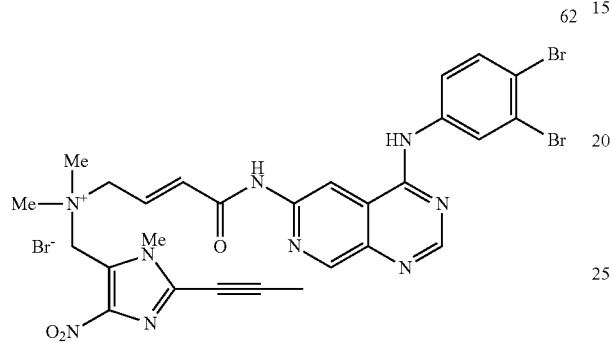
62
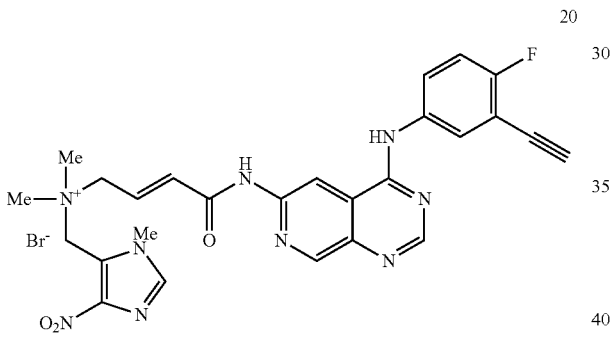
20
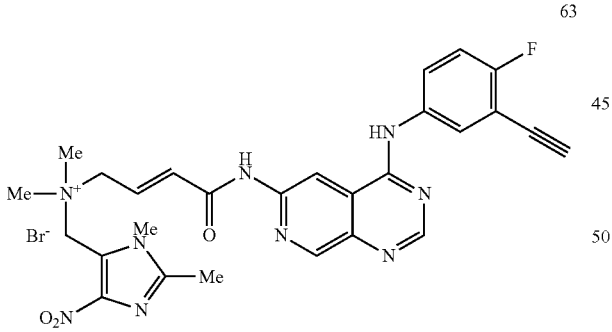
63
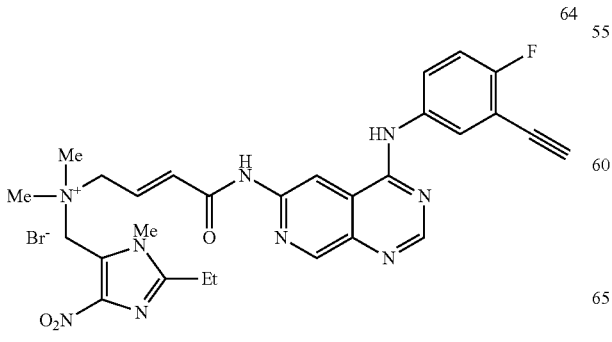
64
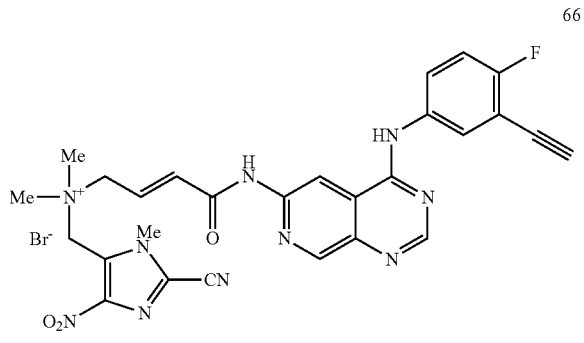
65
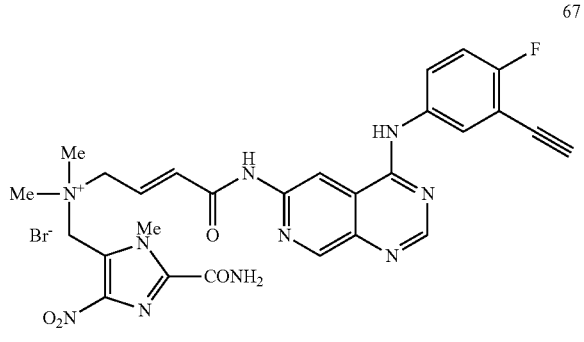
66
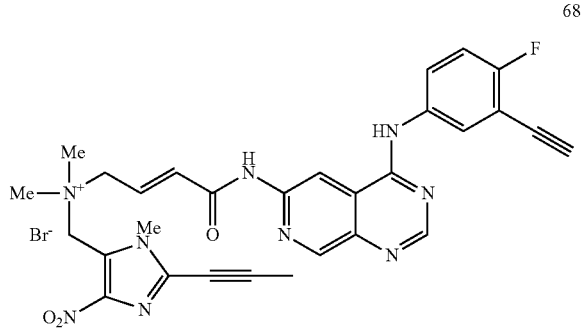
67
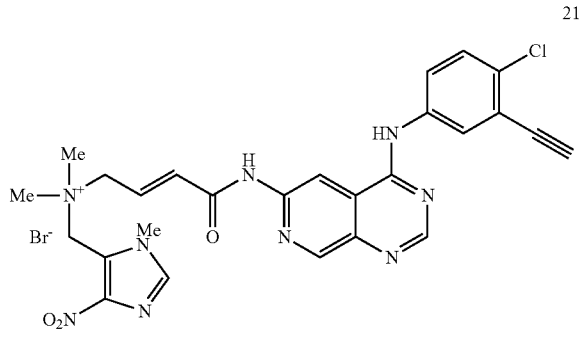
68
21

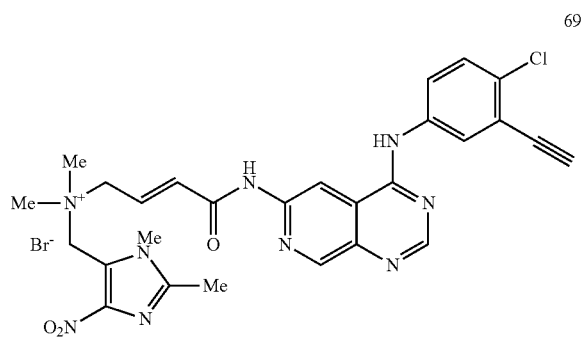
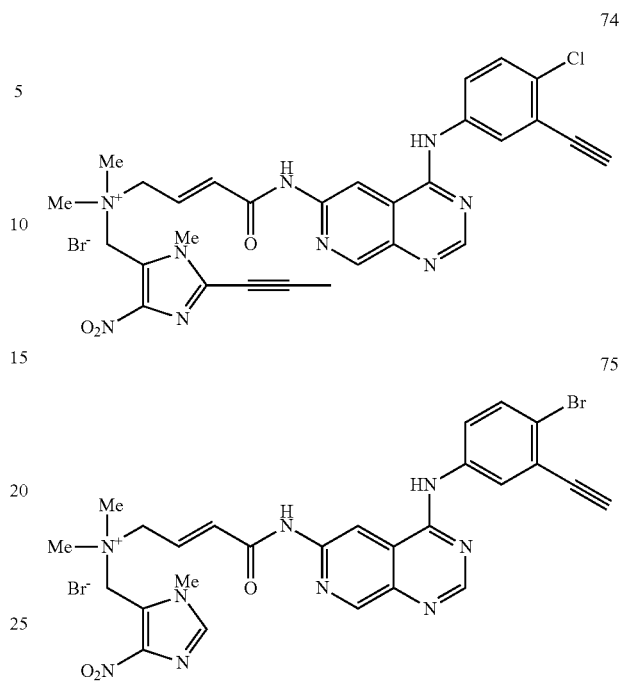
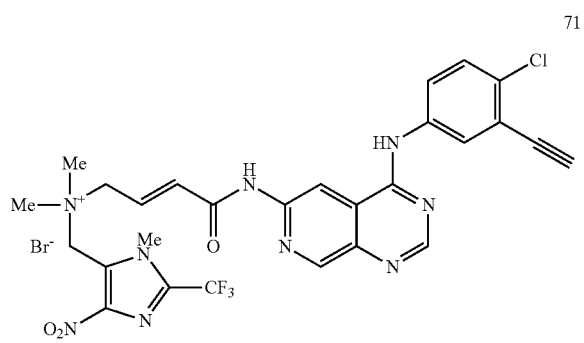
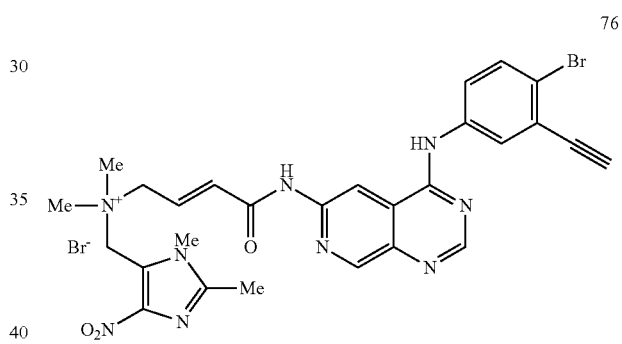
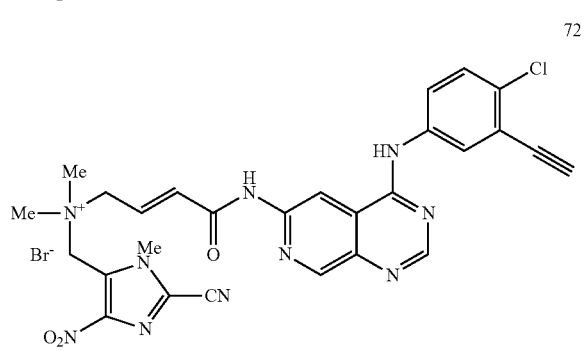
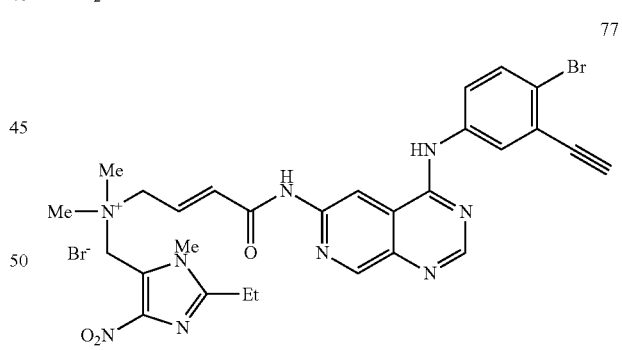
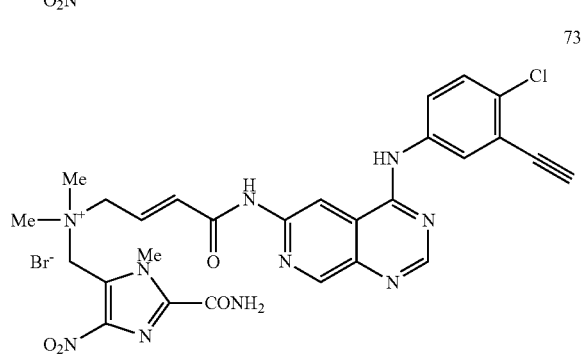
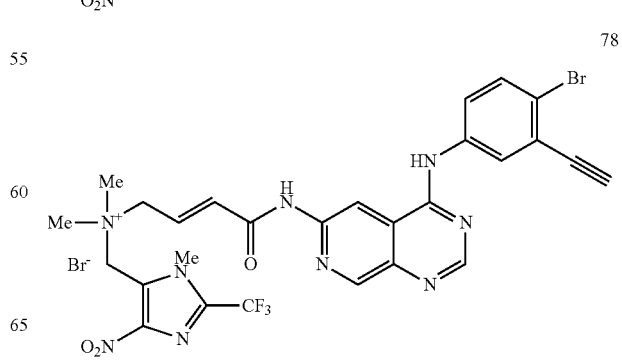

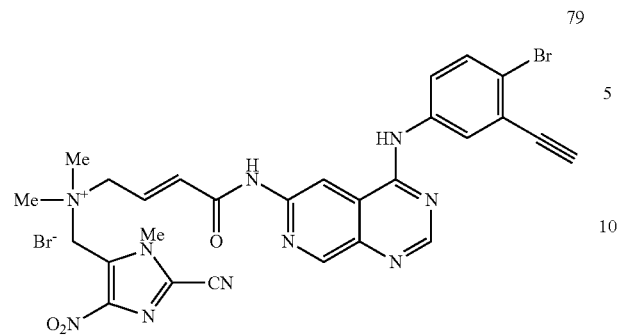
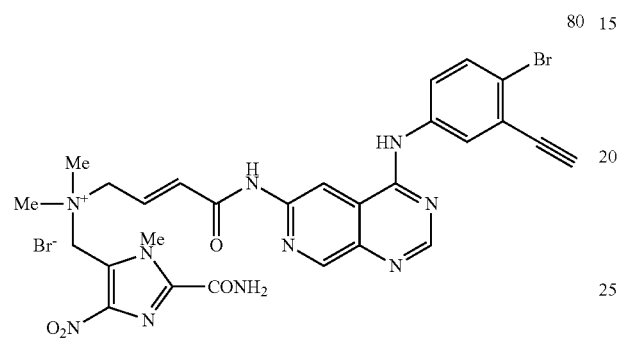
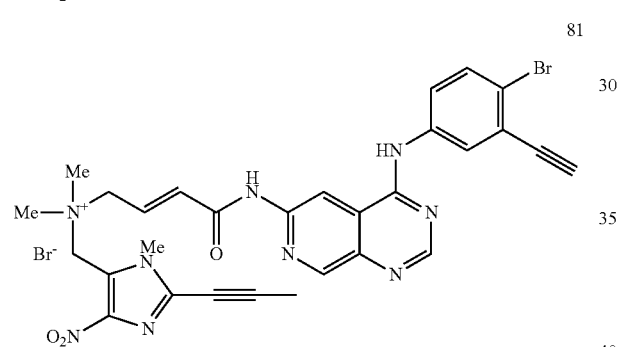
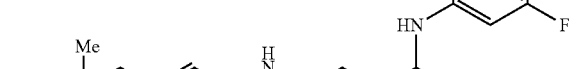
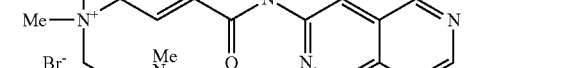
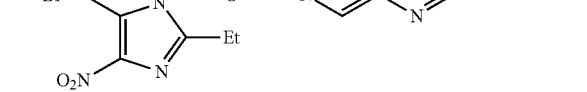

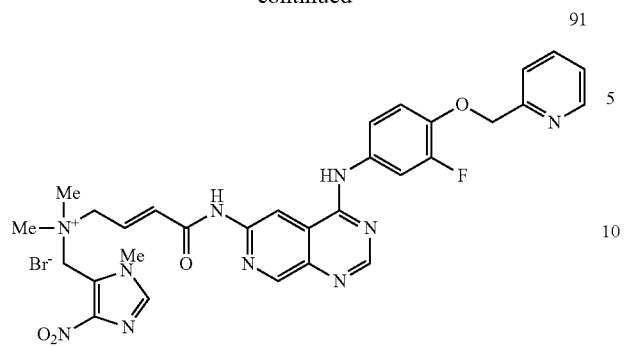
91
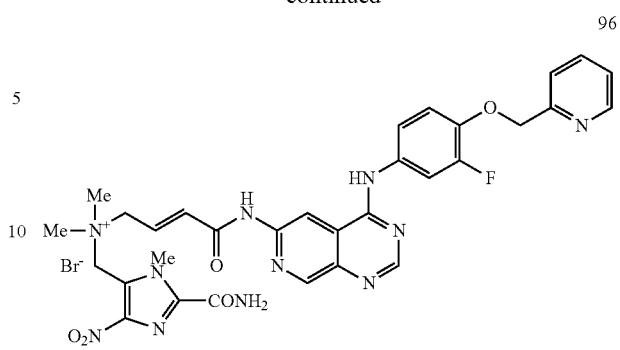
96
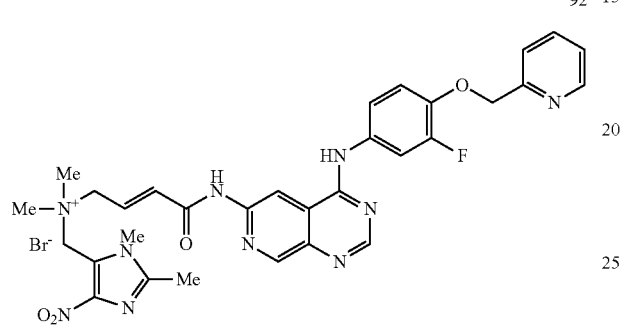
92
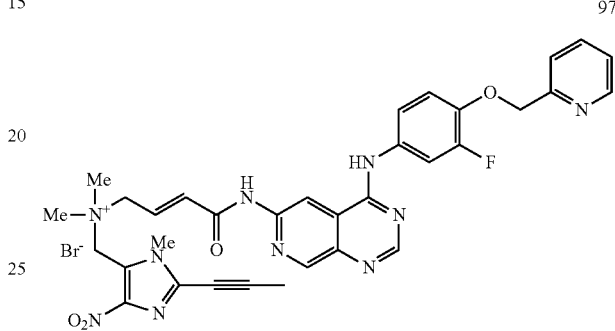
97
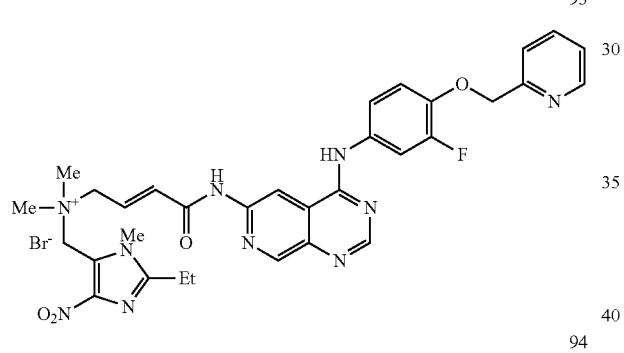
93
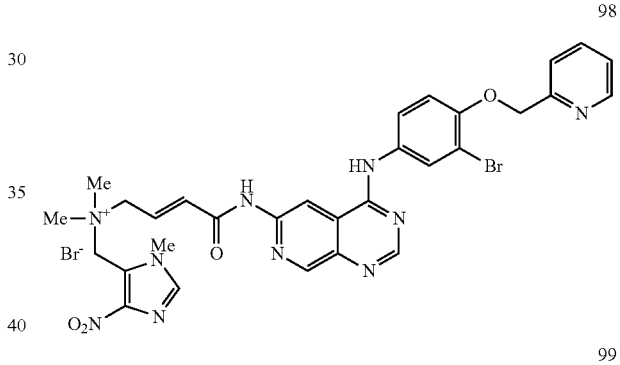
98
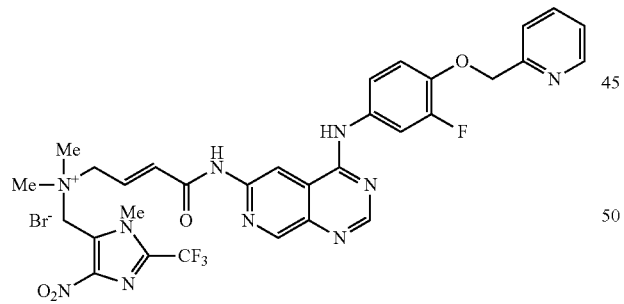
94
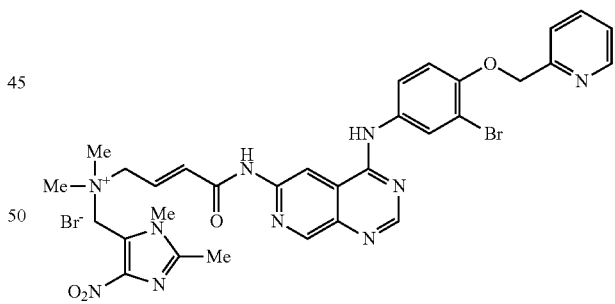
99
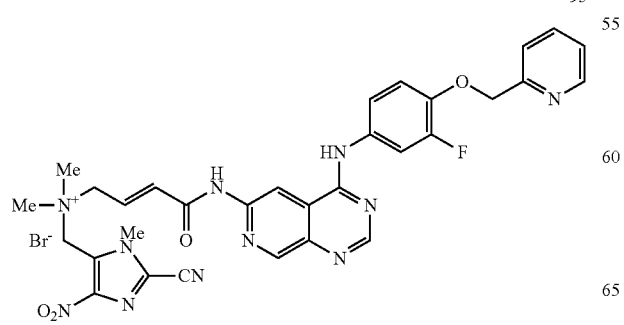
95
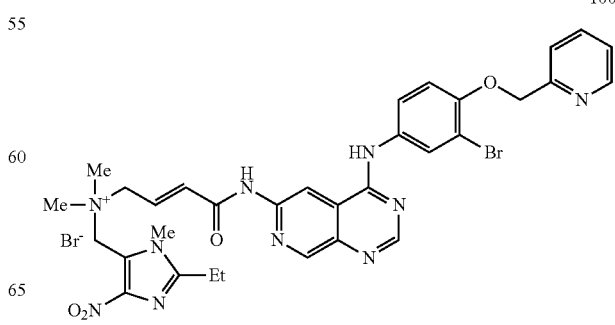
100

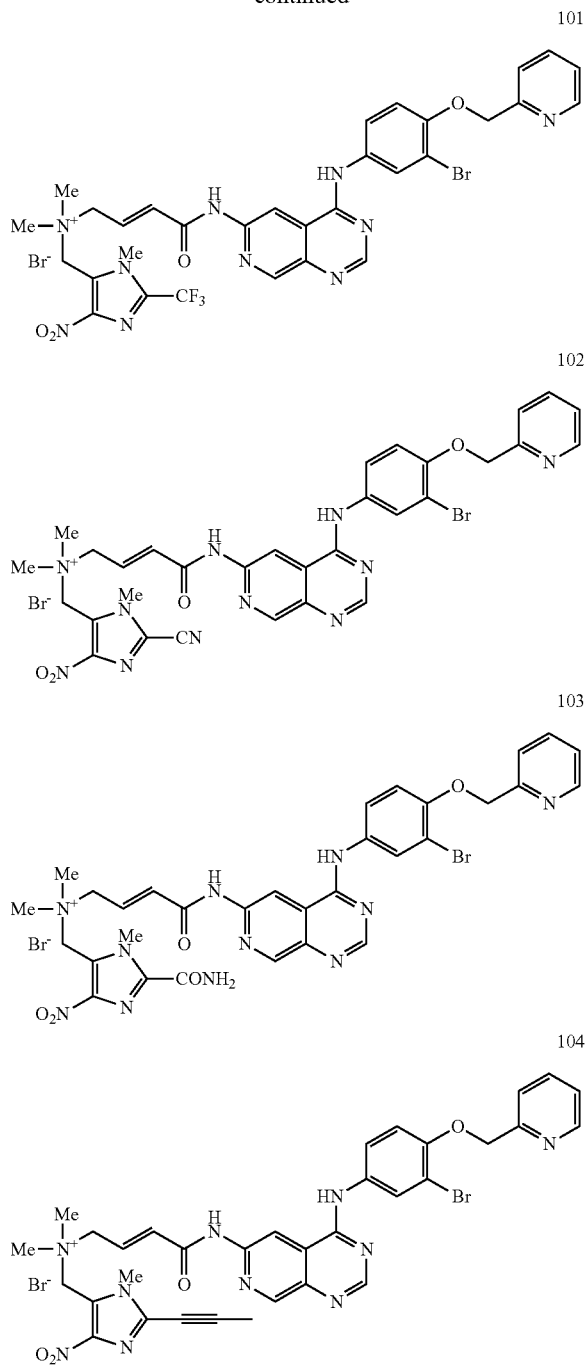

In yet a further aspect, the invention provides a compound of Formula I or salt or solvate thereof as defined above, a reductive prodrug as defined above, or a compound of Formula III or salt or solvate thereof as defined above, for use in therapy.

In still another aspect, the invention provides pharmaceutical compositions comprising a compound of Formula I or salt or solvate thereof as defined above, a reductive prodrug as defined above, or a compound of Formula III or salt or solvate thereof as defined above, in combination with one or more pharmaceutically acceptable excipients or diluents.

In yet a further aspect, the invention provides a method of therapy which includes the step of administering a therapeutically effective amount of a compound of Formula I or salt or solvate thereof as defined above, a reductive prodrug as defined above, or a compound of Formula III or salt or solvate thereof as defined above, to a patient in need of such therapy.

Preferably, the method of therapy is the treatment of cancer.

In yet a further aspect, the invention provides a method of inhibiting kinase activity within a subject which involves the step of administering to said subject an inhibitory amount of a compound of Formula I or salt or solvate thereof as defined above, a reductive prodrug as defined above, or a compound of Formula III or salt or solvate thereof as defined above.

Preferably, said inhibiting of kinase activity is for a therapeutic purpose, including an anti-cancer purpose.

In another aspect, the present invention provides a method for the production of an anti-cancer effect in a warm-blooded animal such as a human, wherein the method comprises administering to the animal an effective amount of a compound of Formula I or salt or solvate thereof as defined above, a reductive prodrug as defined above, or a compound of Formula III or salt or solvate thereof as defined above.

In a further aspect, the present invention provides a method for the production of an anti-cancer effect in a cell, wherein the method comprises contacting the cell with an effective amount of a compound of Formula I or salt or solvate thereof as defined above, a reductive prodrug as defined above, or a compound of Formula III or salt or solvate thereof as defined above.

In a further aspect, the present invention provides a method for the treatment of a cancer in a warm-blooded animal such as a human, which comprises administering to the animal an effective amount of a compound of Formula I or salt or solvate thereof as defined above, a reductive prodrug as defined above, or a compound of Formula III or salt or solvate thereof as defined above.

While the invention is broadly as defined above, it is not limited thereto and also includes embodiments of which the following description provides examples.

BRIEF DESCRIPTION OF THE DRAWINGS

The invention will now be described in more detail, with reference to the accompanying Figures, in which.

DESCRIPTION OF THE INVENTION

Definitions

Figure 1:
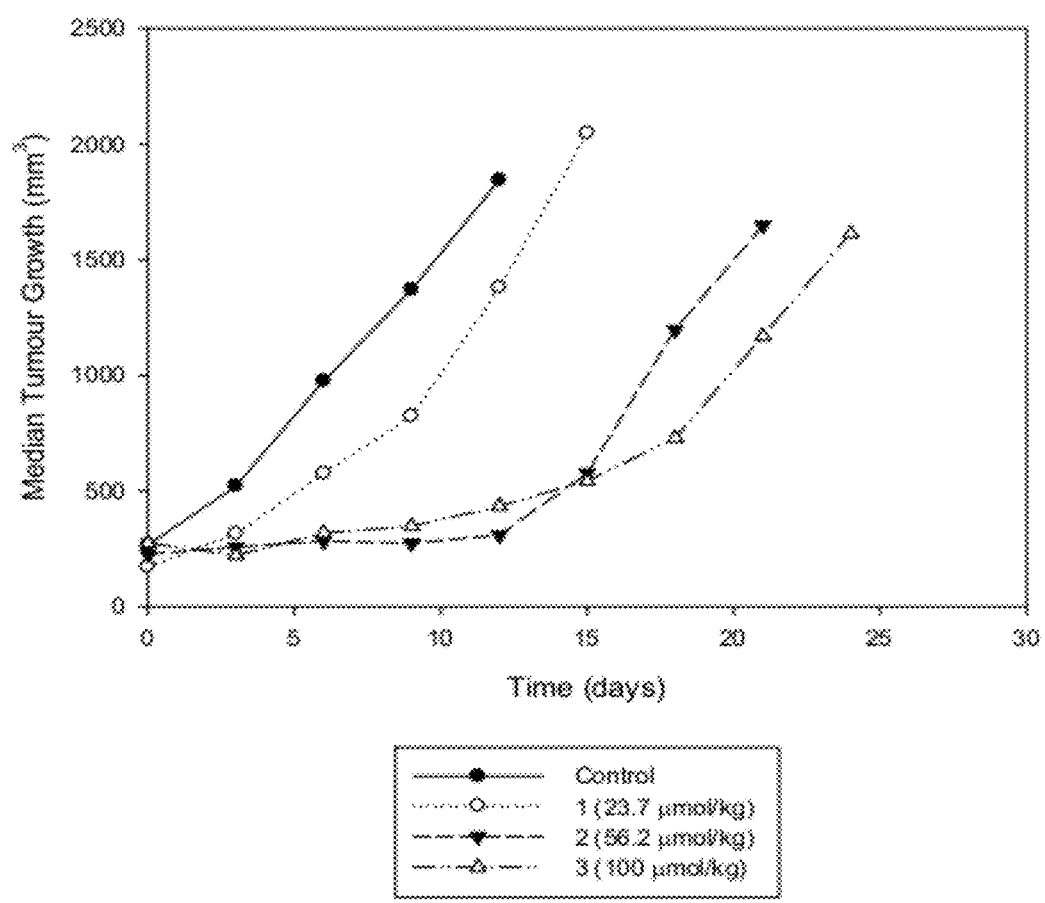
FIG. 1 shows median H1975 tumour growth after q3dx4 treatment with kinase inhibitors 1, 2, 3 (n=3)
Figure 2:
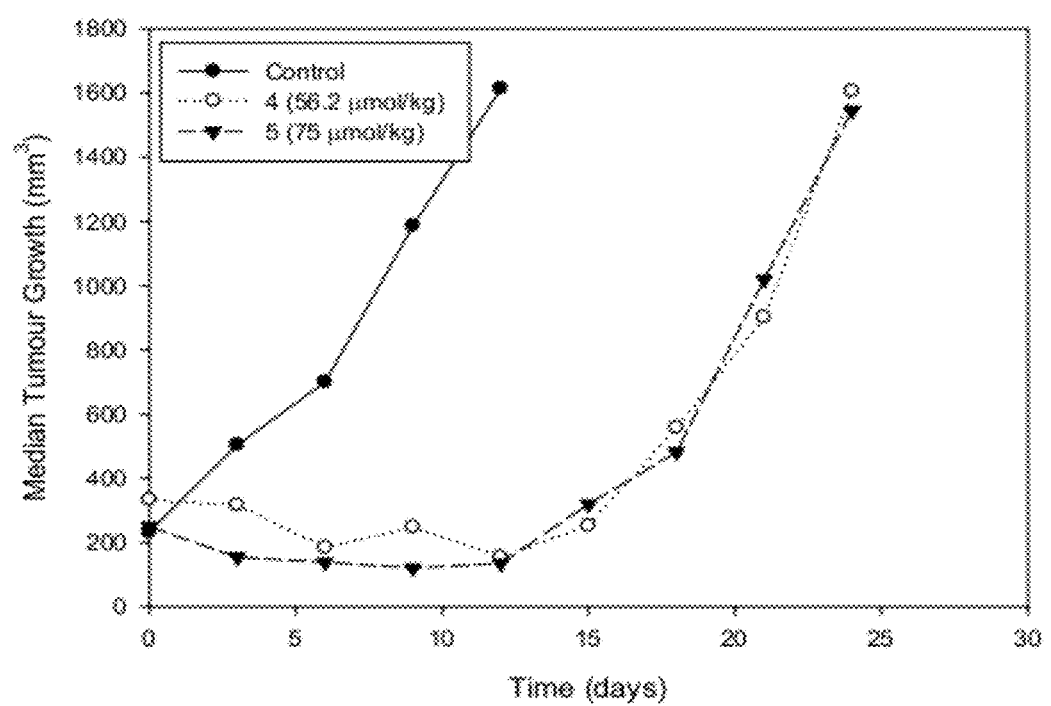
FIG. 2 shows median H1975 tumour growth after q3dx4 treatment with kinase inhibitors 4, 5 (n=3)
Figure 3:
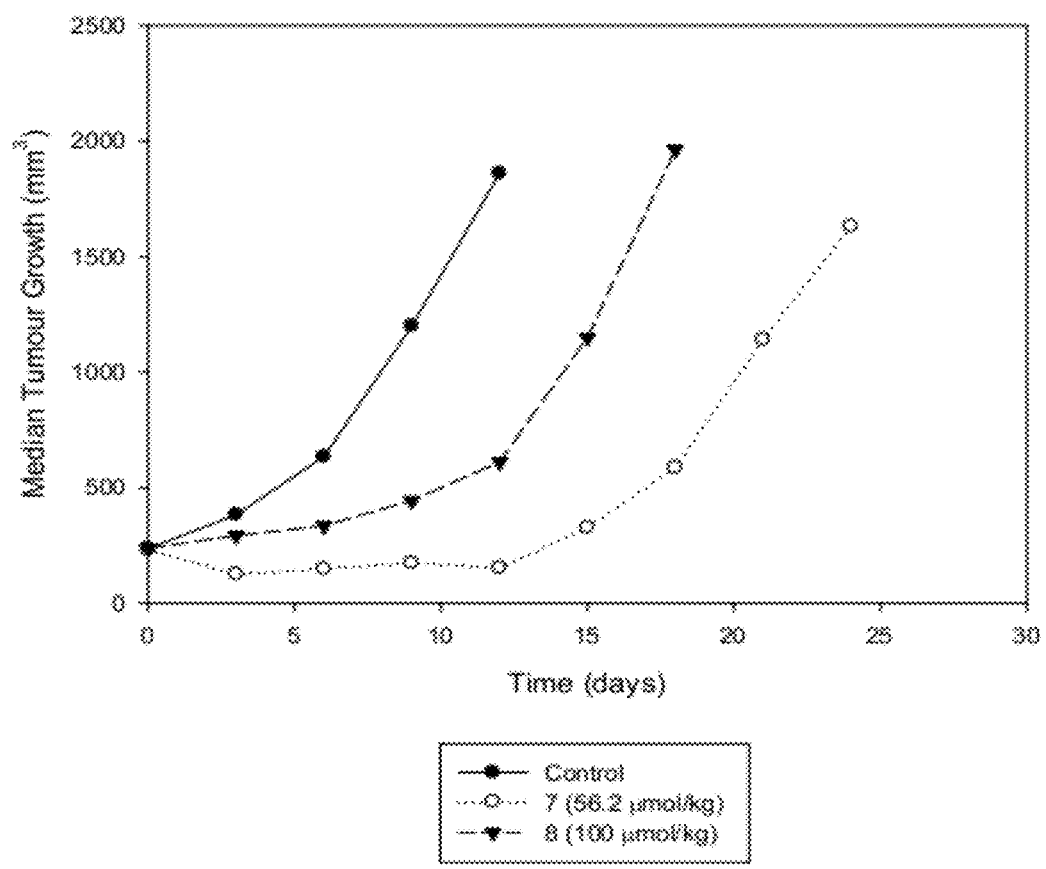
FIG. 3 shows median H1975 tumour growth after q3dx4 treatment with kinase inhibitors 7, 8 (n=3-4)
Figure 4:
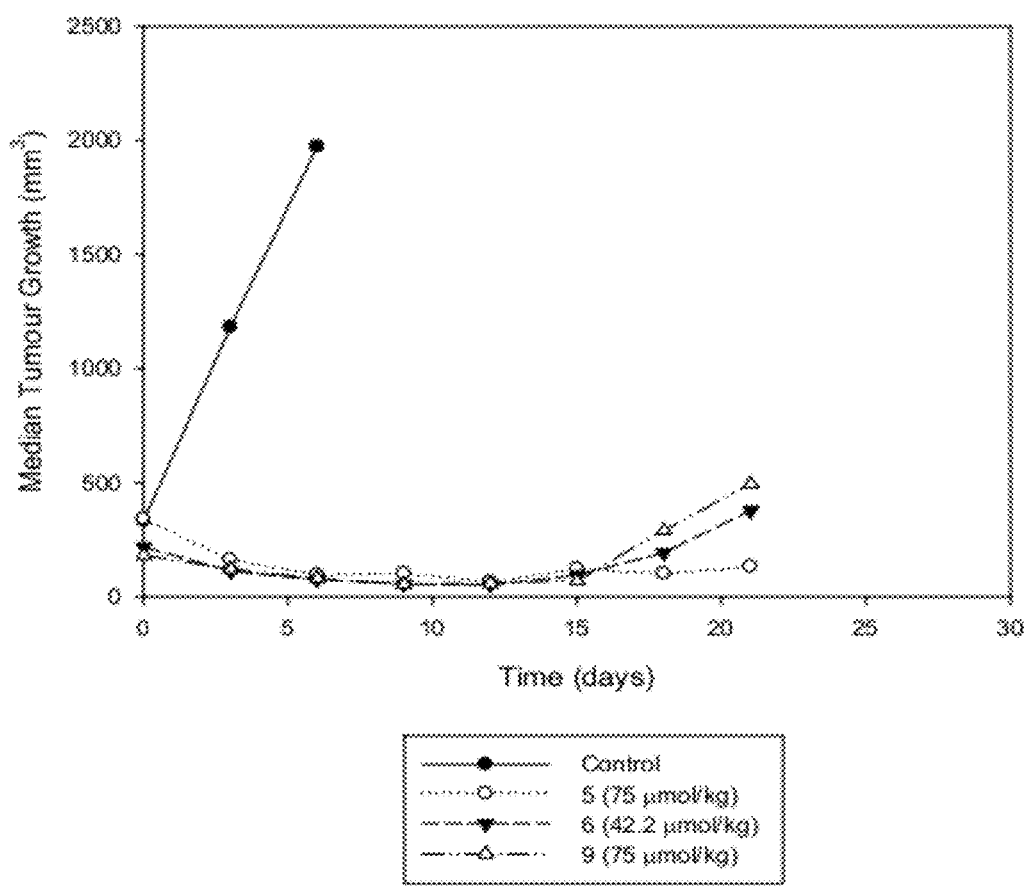
FIG. 4 shows median A431 tumour growth after q3dx4 treatment with kinase inhibitors 5, 6, 9 (n=3)
Figure 5:
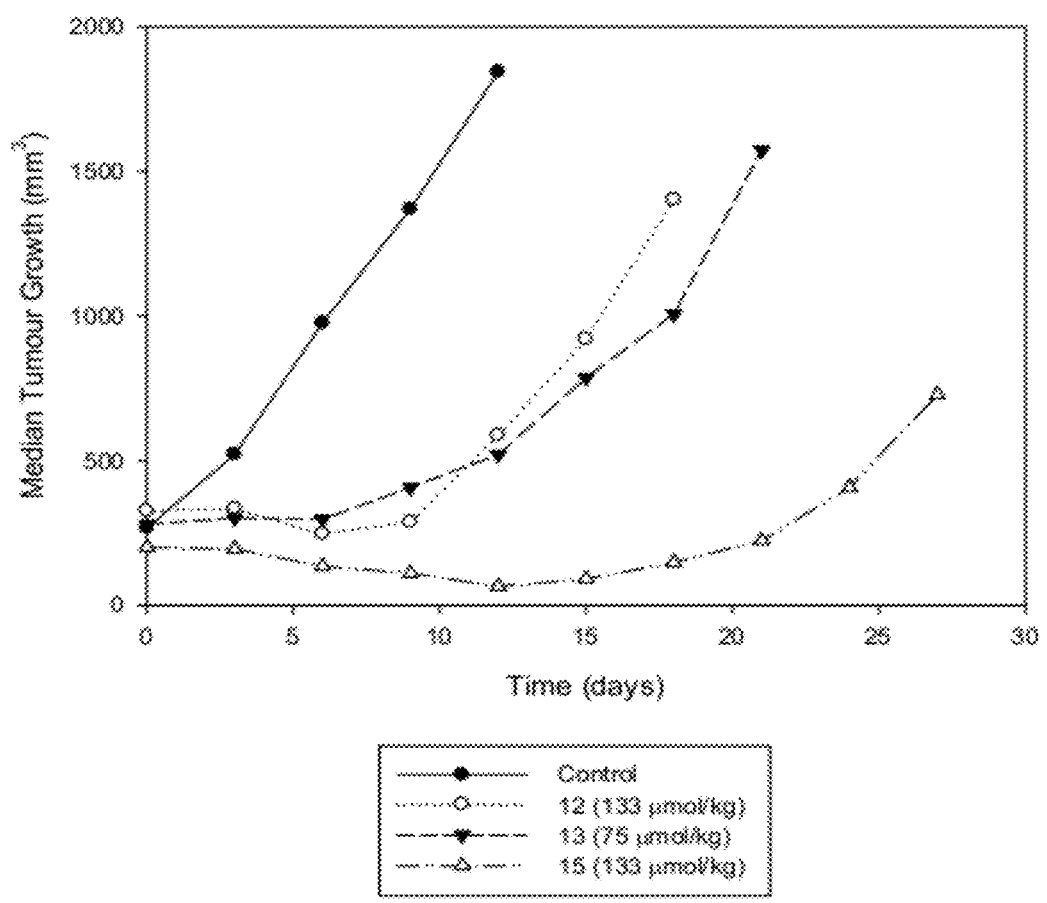
FIG. 5 shows median H1975 tumour growth after q3dx4 treatment with prodrugs 12, 13, 15 (n=3)
Figure 6:
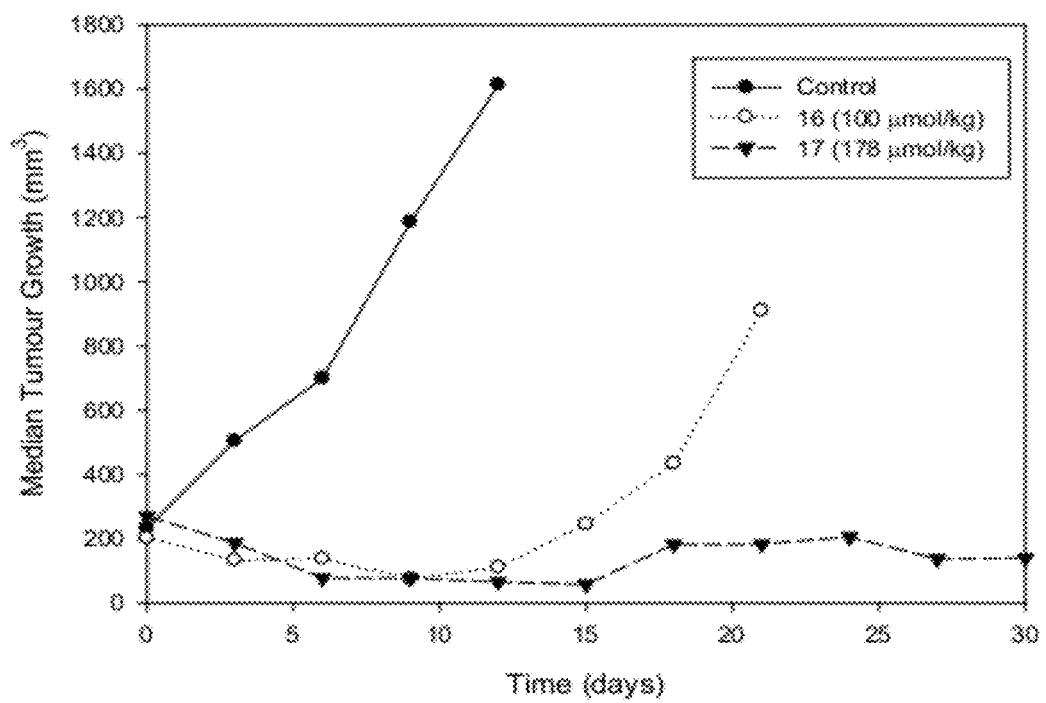
FIG. 6 shows median H1975 tumour growth after q3dx4 treatment with prodrugs 16, 17 (n=3)
Figure 7:
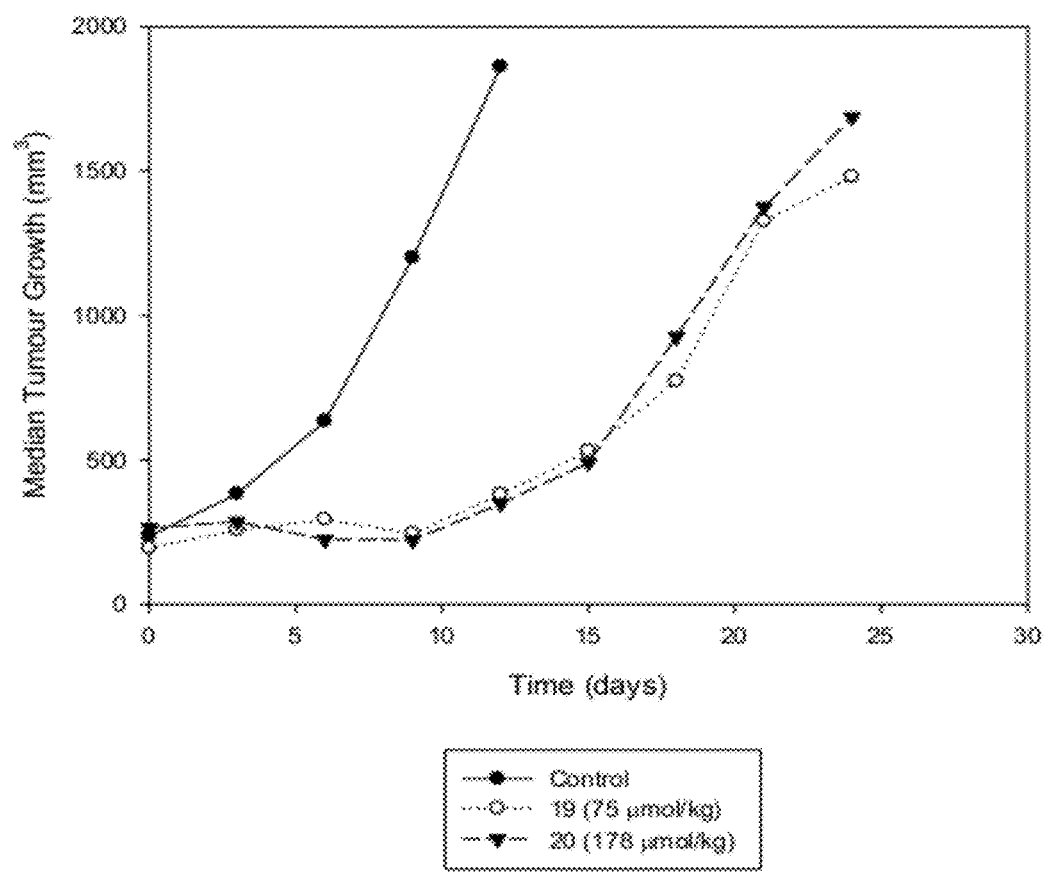
FIG. 7 shows median H1975 tumour growth after q3dx4 treatment with prodrugs 19, 20 (n=3-4)
Figure 8:
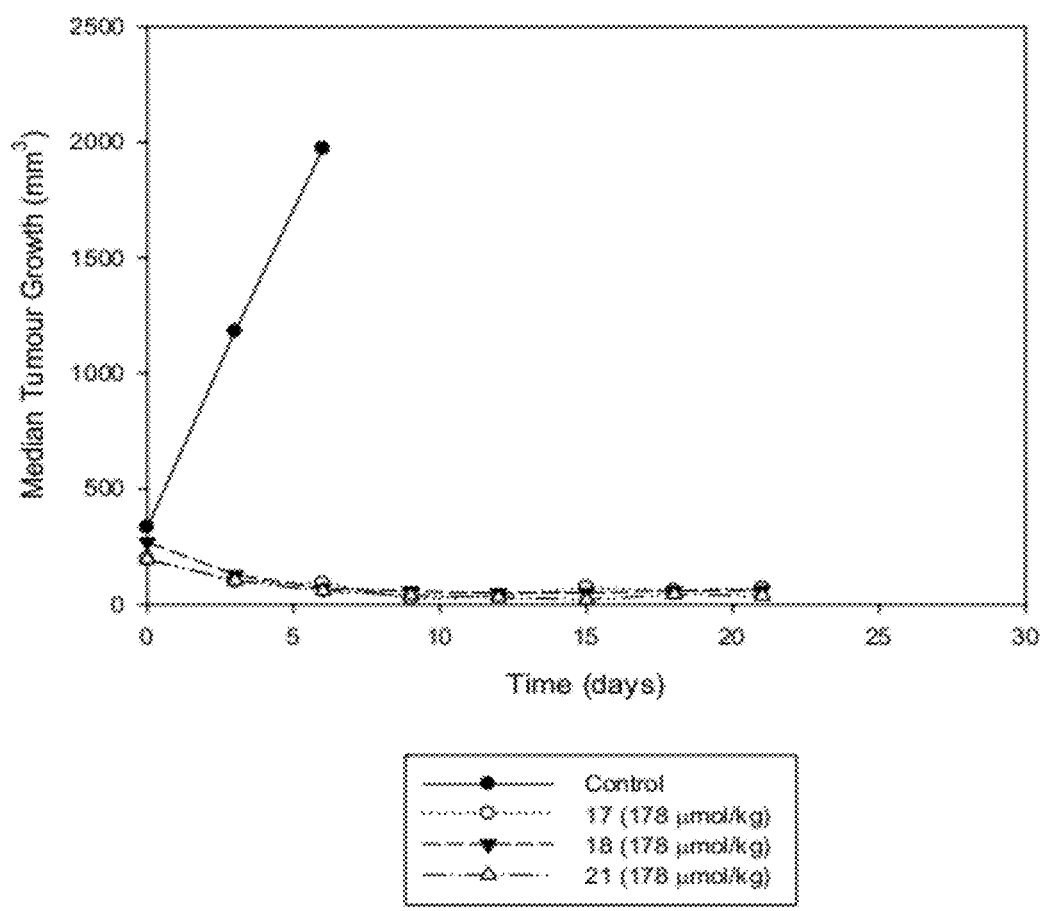
FIG. 8 shows median A431 tumour growth after q3dx4 treatment with prodrugs 17, 18, 21 (n=3)

As used herein, the terms "alkyl" and "alkynyl", unless otherwise specified, include both straight chain and branched chain groups, and unsubstituted and substituted groups. The optional substituents may include, without limitation, halogen, $C_1$-$C_6$ alkoxy, CN, OH, $NH_2$, $NO_2$, $NH(C_1$-$C_6$ alkyl), $N(C_1$-$C_6$ alkyl)$_2$, $CONH_2$, $CO(C_1$-$C_6$ alkyl), $SO_2NH_2$ and $SO_2(C_1$-$C_6$ alkyl).

"Anti-cancer effects" include, but are not limited to, anti-tumour effects, the response rate, the time to disease progression and the survival rate. "Anti-tumour" effects include but are not limited to inhibition of tumour growth, tumour growth delay, regression of tumour, shrinkage of tumour, increased time to regrowth of tumour on cessation of treatment and slowing of disease progression.

"Effective amount" means an amount of a compound that, when administered to a subject for treating a cancer, is sufficient to effect such treatment for the cancer. The "effective amount" will vary depending on the cancer to be treated, the compound to be administered, the severity of the cancer treated, the age and relative health of the subject, the route and form of administration, whether the treatment is monotherapy or combination therapy, the judgement of the attending clinician, and other factors.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid and the like; or formed with organic acids such as acetic acid, methanesulfonic acid, maleic acid, tartaric acid, citric acid and the like; or salts formed when an acidic proton present in the parent compound either is replaced by a metal ion, e.g. an alkali metal ion, an alkaline earth ion, or an aluminium ion; or coordinates with an organic or inorganic base. Acceptable organic bases include ethanolamine, diethanolamine, N-methylglucamine, triethanolamine and the like. Acceptable inorganic bases include aluminium hydroxide, calcium hydroxide, potassium hydroxide, sodium carbonate and sodium hydroxide.

"Warm blooded animal" means any member of the mammalia class including, but not limited to humans, non-human primates such as chimpanzees and other apes and monkey species, farm animals such as cattle, horses, sheep, goats, and swine; domestic animals such as rabbits, dogs and cats; laboratory animals including rodents, such as rats, mice and guinea pigs, and the like.

Compounds of the Invention

As defined above, in broad terms the invention relates to compounds useful as kinase inhibitors. Such compounds have application in therapy.

In one embodiment, the compounds of the invention are 4-anilinopyrido[3,4-d]pyrimidine irreversible erbB1, 2, 4 kinase inhibitors of Formula I.

In another embodiment, the compounds comprise a kinase inhibitor of Formula I and a reductive trigger. The reductive trigger fragments when reduced. Preferably fragmentation of the trigger occurs at the one-electron reduction level and is effectively suppressed by the presence of oxygen, thus providing selective activation in hypoxic environments. This suppression by oxygen may occur through reoxidation of the one-electron radical by oxygen, or by oxidation of reducing intermediates required for prodrug reduction. The latter would include, for example, scavenging by oxygen of radiation-induced reducing radicals such as the aquated electron, or oxidation of reducing intermediates in the catalytic cycle of reductase enzymes. The reduction equivalents required to reduce the trigger may be provided by enzymes, radiation-induced radicals, or chemical reducing agents.

In preferred forms, the trigger is a reductively-activated aromatic nitroheterocycle or aromatic nitrocarbocycle trigger and is linked directly to a quaternisable nitrogen of a compound of Formula I such that a quaternary nitrogen is formed. It is however particularly preferred that the trigger has the structure of Formula II above.

In such embodiments, the compounds act as prodrugs, with reduction of the trigger releasing the kinase inhibitor. It is presently most preferred that the prodrug forms of the compounds of the invention are of Formula III as defined above.

Therapeutic Applications of Compounds of the Invention

The compounds of the invention have application in any therapeutic approach in which inhibition of the activity of a kinase is desirable. The invention therefore relates to methods for treating and preventing diseases, for example, hyper-proliferative, inflammatory and angiogenesis disorders and osteoporosis in mammals by administering a compound of this invention or a pharmaceutical composition comprising one or more compounds of this invention.

The invention particularly relates to a method of treating or preventing cancer and other hyperproliferative disorders by administering a compound of this invention or a pharmaceutical composition comprising one or more compounds of this invention, whether alone as a monotherapy or in combination with a second anti-proliferative agent.

Optional anti-proliferative agents which can also be adminstered include but are not limited to compounds listed on the cancer chemotherapy drug regimens in the 14th Edition of the Merck Index (2006), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Additional anti-proliferative agents include other molecular targeted agents which modulate parallel pathways such as MEK 1/2 inhibitors, AKT inhibitors and mTOR inhibitors, monoclonal antibodies, oxaliplatin, gemcitabine, gefinitib, taxotere, ara A, ara C, herceptin, BCNU, CCNU, DTIC, and actinomycin D. Still further anti-proliferative agents include but are not limited to those compounds acknowledged to be used in the treatment of neoplastic diseases in *Goodman and Gilman's The Pharmacological Basis of Therapeutics* (Eleventh Edition), editor Molinoff et al., publ. by McGraw-Hill, pages 1225-1287 (2006), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, tenipdside, testosterone propionate, thiotepa, trimethylmelamine, uridine, and vinorelbine.

Cancer and hyperproliferative disorders as used herein include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophthalmic glioma, cerebellar and cerebral astrocytoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in man, but also exist with a similar etiology in other warm-blooded animals, and can be treated by pharmaceutical compositions of the present invention.

Conditions within a human or other warm-blooded animal which can be treated by administering a compound of this invention include tumor growth, retinopathy, including diabetic retinopathy, ischemic retinal-vein occlusion, retinopathy of prematurity and age related macular degeneration; psoriasis, or bullous disorder associated with subepidermal blister formation, including bullous pemphigoid, erythema multiforme, or dermatitis herpetiformis, rheumatoid arthritis, osteoarthritis, septic arthritis, tumor metastasis, periodontal disease, cornal ulceration, proteinuria, coronary thrombosis from atherosclerotic plaque, aneurismal aortic, dystrophobic epidermolysis bullosa, degenerative cartilage loss following traumatic joint injury, osteopenias mediated by MiVIP activity, tempero mandibular joint disease or demyelating disease of the nervous system.

It will be appreciated by those skilled in the art that a particular method of therapy will employ a selected route of administration which will in turn depend on a variety of factors, all of which are considered routinely when administering therapeutics. It will be further appreciated by one skilled in the art that the optimal course of treatment, i.e., the mode of treatment and the daily number of doses of a compound of this invention given for a defined number of days, can be ascertained by those skilled in the art using conventional treatment tests.

Therapeutic dosages will likely be in the range of 1 mg to 3000 mg per day. The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Pharmaceutical Compositions of Compounds of the Invention

The invention also includes pharmaceutical compositions including a compound of this invention, and a pharmaceutically acceptable carrier.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Preparation of Quaternary Nitrogen Salt Prodrugs of the Invention

The prodrug compounds of the present invention comprise an effector moiety linked to a reductive trigger, which is preferably a nitroheterocyclic reductive trigger of Formula II, more preferably of Formula IIa, as defined above.

The effector moiety is a 4-anilinopyrido[3,4-d]pyrimidine irreversible erbB1, 2, 4 kinase inhibitor of Formula I.

The 4-anilinopyrido[3,4-d]pyrimidine irreversible erbB1, 2, 4 kinase inhibitors of Formula I possess an amide Michael acceptor in the 6-position, where the Michael acceptor features a double bond that is substituted at the beta carbon with a methylene group that terminates with a tertiary dimethylamine group, as shown below.

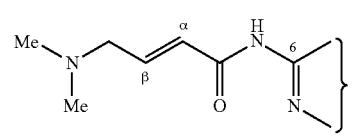

Formula IVa

It will be appreciated that the remainder of the effector moiety not shown in Formula IVa has a bicyclic aromatic ring structure as defined in Formula I.

The preferred prodrug compounds are of Formula III as defined above. In general terms, the preferred prodrug compounds of Formula III may be prepared by quaternising an aliphatic tertiary dimethylamine effector moiety with a nitroheterocyclic reductive trigger moiety. Such methods are described in more detail below.

Preparation of 4-anilinopyrido[3,4-d]pyrimidine irreversible erbB1,2,4 kinase inhibitors Effector compounds related to those of the Formula I as shown above, where the central inhibitor scaffold is a 4-anilinopyrido[3,4-d]pyrimidine and the 6-position is substituted with an amide Michael acceptor may be prepared according to methods described in the art when the amide Michael acceptor, for example, is unsubstituted (Smaill et al. J Med Chem, 1999, 42, 1803-1815), substituted at the N-position, alpha-position or beta-position with a range of groups (Smaill et al. J Med Chem, 2001, 44, 429-440) excluding dimethylaminomethylene as described above and when the Michael acceptor contains a triple bond substituted at the beta-position (Klutchko et al. J Med Chem, 2006, 49, 1475-1485; U.S. Pat. No. 6,602,863). Compounds of Formula I of the present invention may be prepared using analogous methods.

Scheme 1 below illustrates the preparation of 4-anilinopyrido[3,4-d]pyrimidine effector compounds of the invention, from the known intermediate 6-fluoropyrido[3,4-d]pyrimidinone (200) (Rewcastle et al, J Chem Soc, Perkins Trans 1, 1996, 2221-2226) using the methods of Rewcastle et al, J Chem Soc, Perkins Trans 1, 1996, 2221-2226 and Soyka et al, US 2005/0085495 A1.

Scheme 2 below illustrates the preparation of specific effector compounds of the invention. Thionyl chloride mediated conversion of 6-fluoropyrido[3,4-d]pyrimidinone (200) to 4-chloro-6-fluoropyrido[3,4-d]pyrimidine, followed by reaction with the appropriate aniline provided the 4-anilino-6-fluoropyrido[3,4-d]pyrimidines (201-209). Fluorine displacement with 4-methoxybenzyl amine then gave the benzylamines (210-218), which were reacted with trifluoroacetic acid (FA) to provide the amines (219-227). MI-promoted amide coupling with 2-(diethoxyphosphoryl)acetic acid gave the phosphonates (228-236). Horner-Wadsworth-Emmons coupling of these with the aldehyde derived from in situ

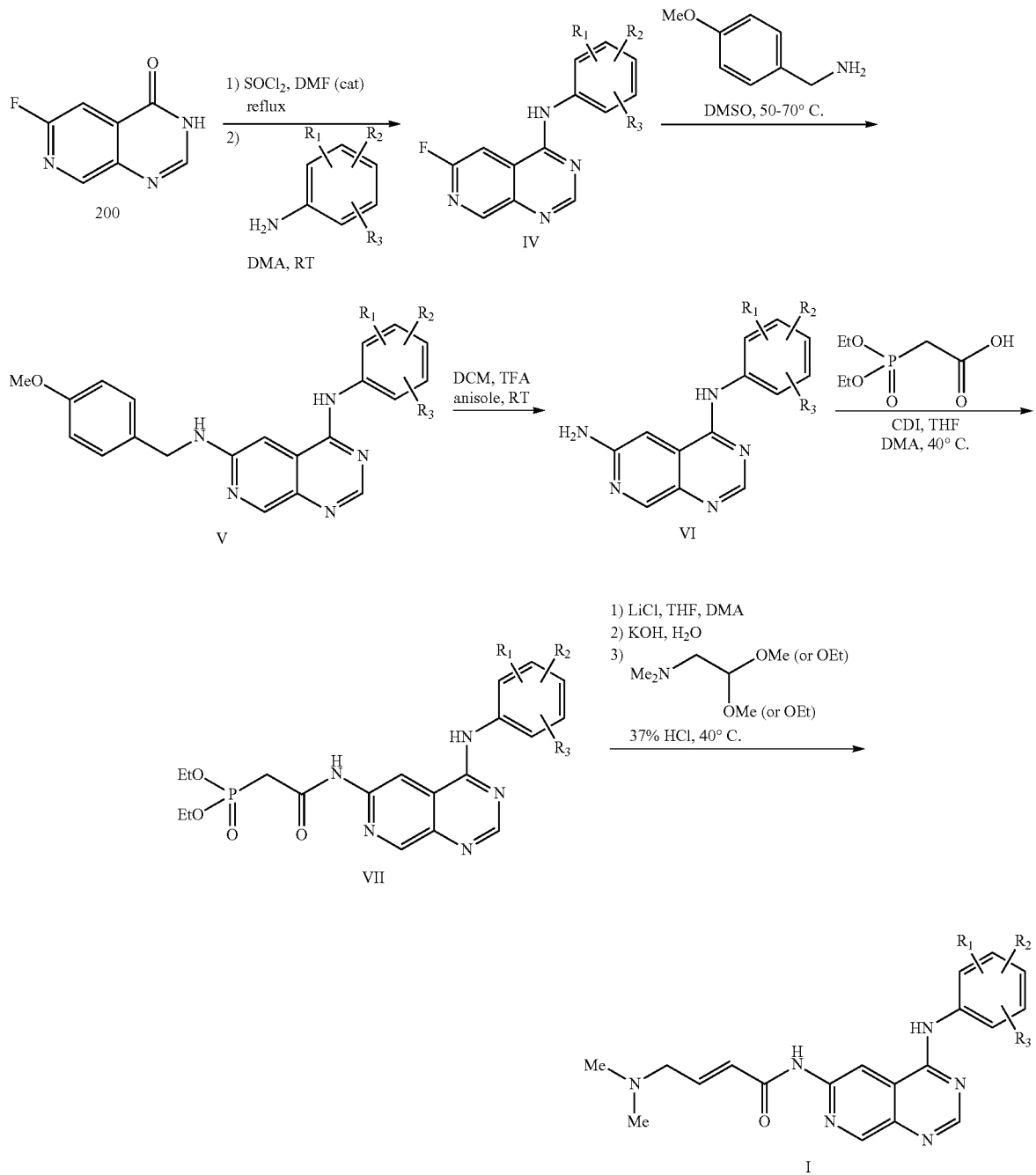

hydrolysis of 2,2-diethoxy-N,N-dimethylethanamine then provided the exemplary effector compounds 1-9.

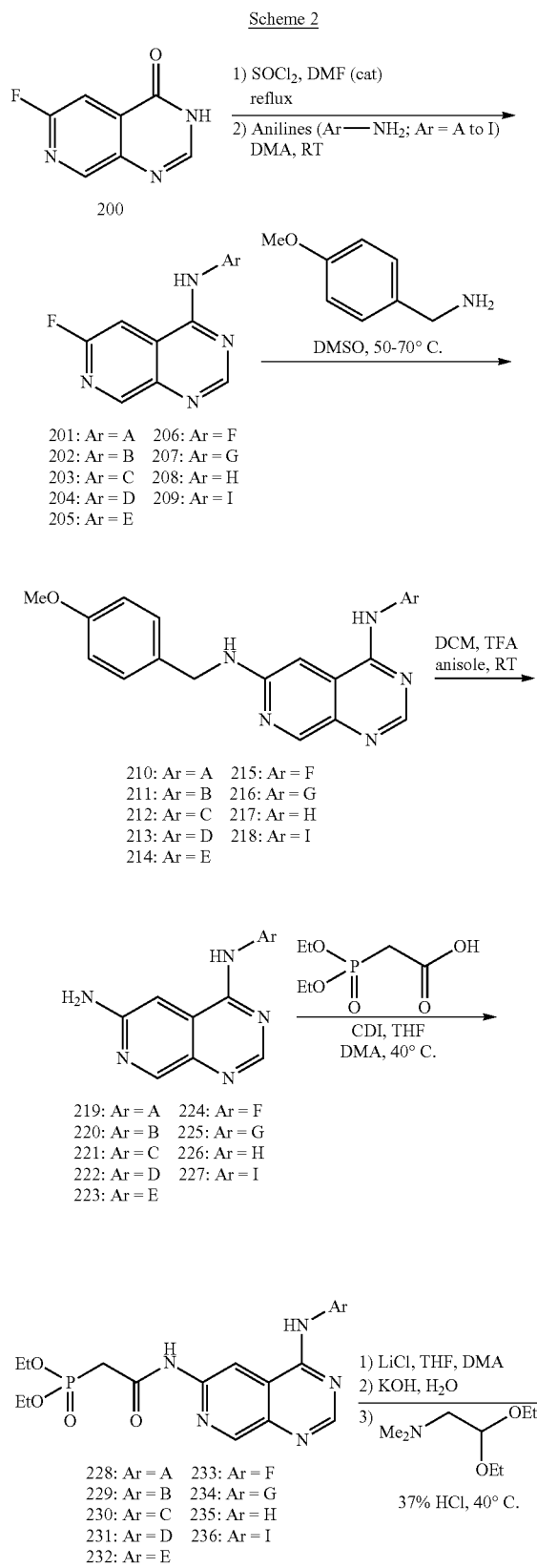

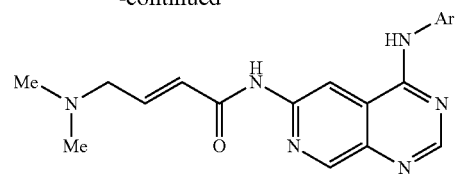

1: Ar = A  6: Ar = F
2: Ar = B  7: Ar = G
3: Ar = C  8: Ar = H
4: Ar = D  9: Ar = I
5: Ar = E

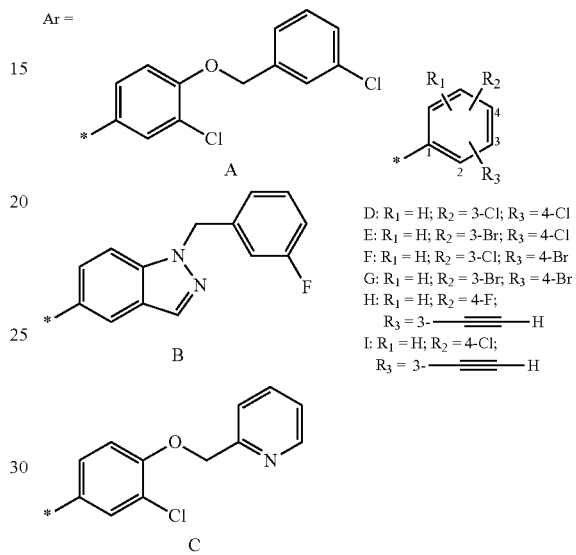

D: $R_1$ = H; $R_2$ = 3-Cl; $R_3$ = 4-Cl
E: $R_1$ = H; $R_2$ = 3-Br; $R_3$ = 4-Cl
F: $R_1$ = H; $R_2$ = 3-Cl; $R_3$ = 4-Br
G: $R_1$ = H; $R_2$ = 3-Br; $R_3$ = 4-Br
H: $R_1$ = H; $R_2$ = 4-F;
   $R_3$ = 3-—≡—H
I: $R_1$ = H; $R_2$ = 4-Cl;
   $R_3$ = 3-—≡—H

Preparation Prodrugs

The prodrug compounds of the invention may, in general terms, be prepared by reacting an aliphatic tertiary amine-bearing kinase inhibitor of Formula I with an appropriate nitroheterocyclic or nitrocarbocyclic α-methyl halide/mesylate/tosylate, in a suitable solvent and for a suitable length of time (for example in N-methyl-2-pyrrolidinone for about 15 hours), to produce a quaternary nitrogen salt comprising the nitroheterocyclic or nitrocarbocyclic reductive trigger moiety linked directly or indirectly to a nitrogen of the kinase inhibitor.

Preferred reductive trigger moieties suitable for use in the prodrugs of the invention are of Formula II shown below:

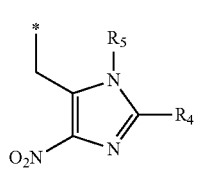

II where $R_4$ and $R_5$ are as defined above.

Particularly preferred reductive trigger moieties are of Formulae IIa-IIg, shown below:

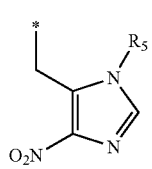

IIa

-continued

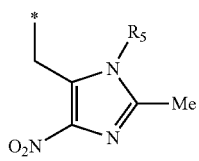

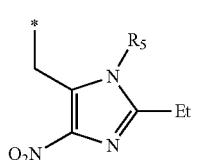

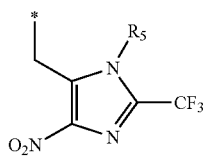

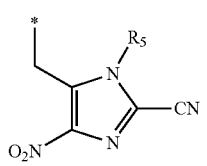

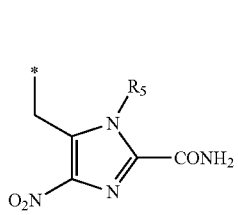

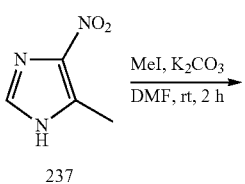

The α-methyl halides of Formula IIa may be prepared as described previously (bromide; Stribbling et al, PCT International patent publication WO 2008/039087) (chloride; Tercel et al, J Med Chem, 2001, 44, 3511-3522).

Scheme 3 below illustrates two alternate methods to the α-methyl bromide 239, from commercially available starting materials.

Scheme 3

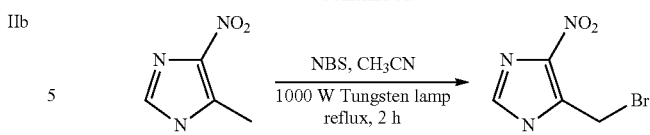

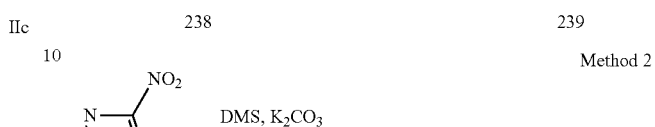

Method 2

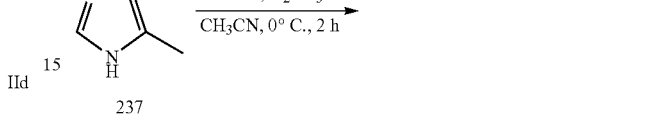

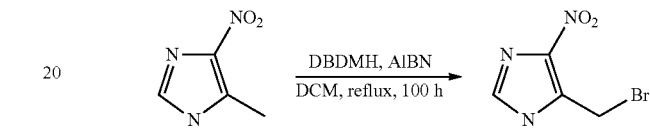

Scheme 4 below illustrates a route to the α-methyl bromide 244, from commercially available starting materials.

Scheme 4

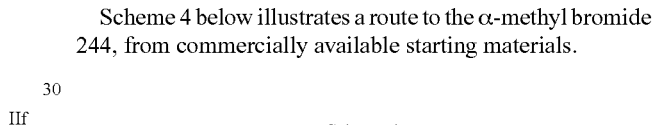

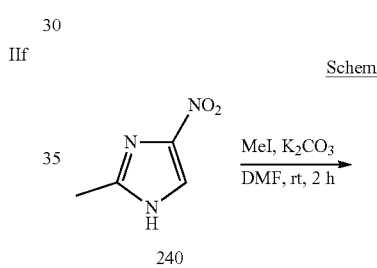

Scheme 5 below illustrates a route to the α-methyl bromide 250, from 1,5-dimethyl-4-nitro-1H-imidazole (238) (Scheme 3).

Scheme 5

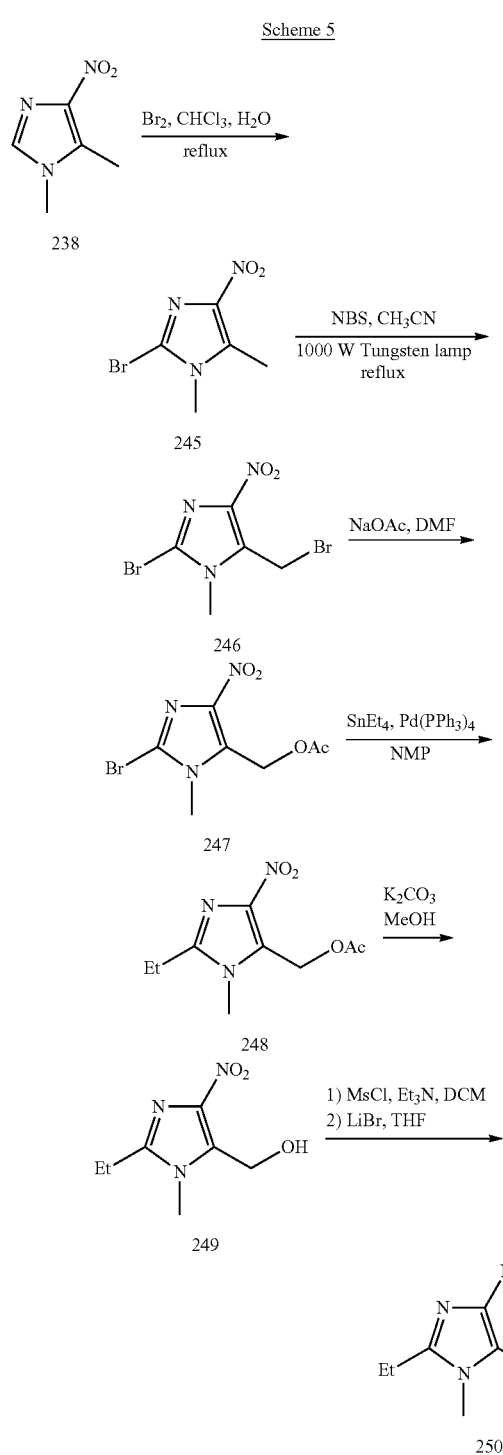

Scheme 6 below illustrates a route to the α-methyl bromide 261 from the commercially available oxazole (251).

Scheme 6

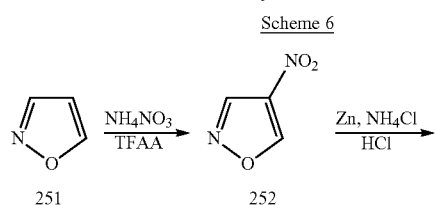

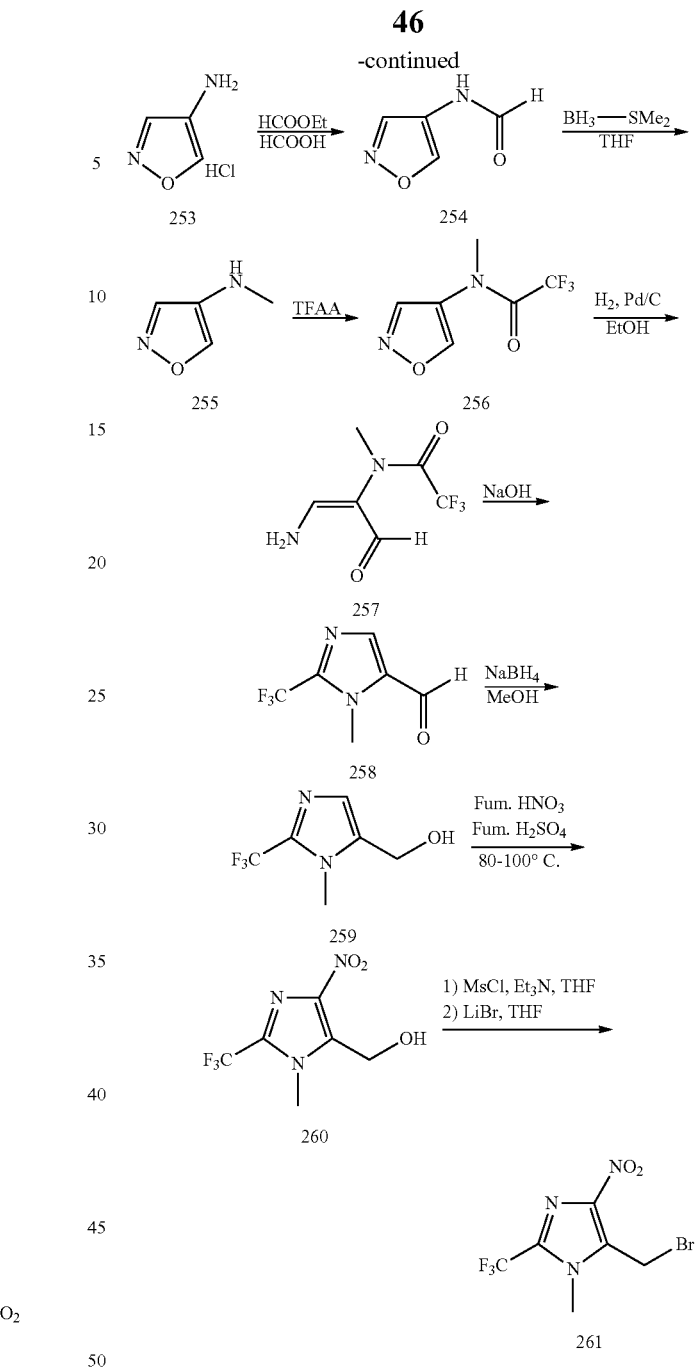

Scheme 7 below illustrates two alternate routes to the α-methyl bromide 264, from α-methyl bromide 246 (Scheme 5) and 2-bromo-1,5-dimethyl-4-nitro-1H-imidazole (245) (Scheme 5), respectively. Scheme 7 below also illustrates a route to the α-methyl bromide 266, from α-methyl bromide 264.

Scheme 7

Method 1

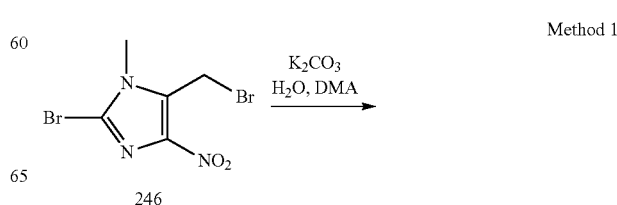

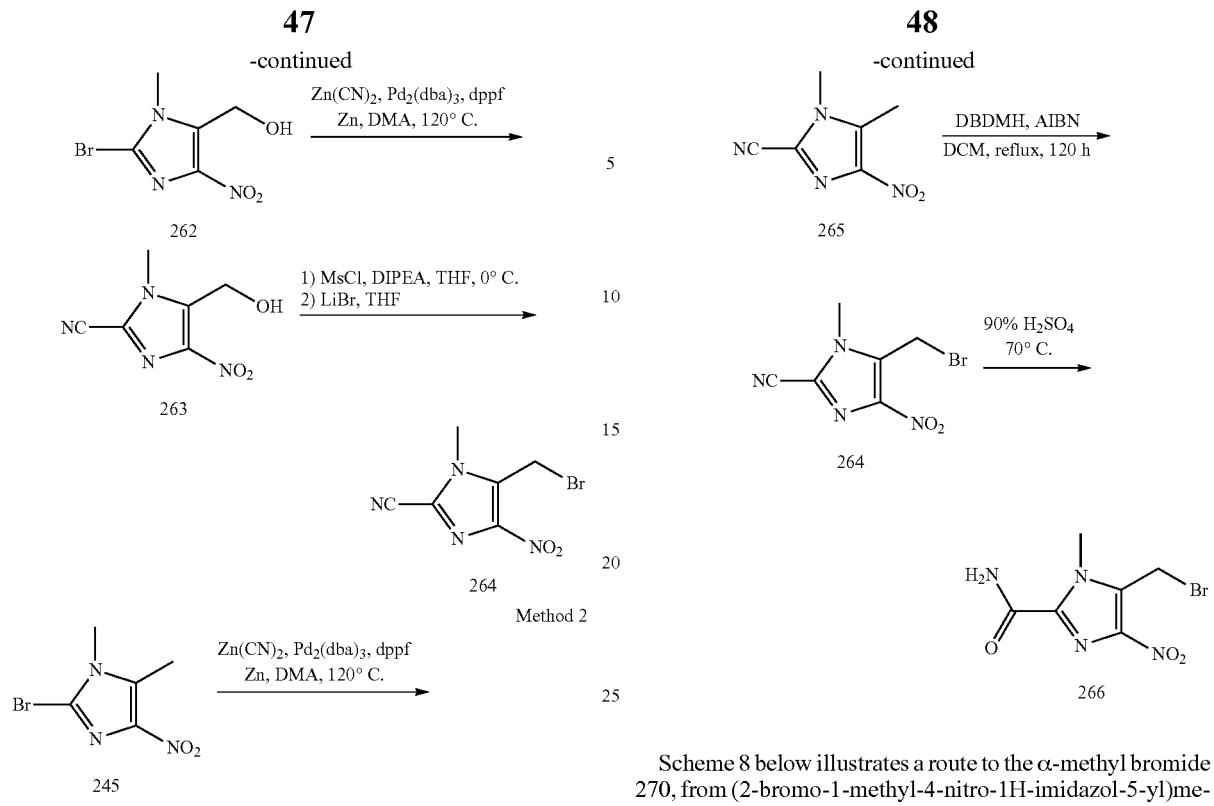

Scheme 8 below illustrates a route to the α-methyl bromide 270, from (2-bromo-1-methyl-4-nitro-1H-imidazol-5-yl)methyl acetate (247) (Scheme 5).

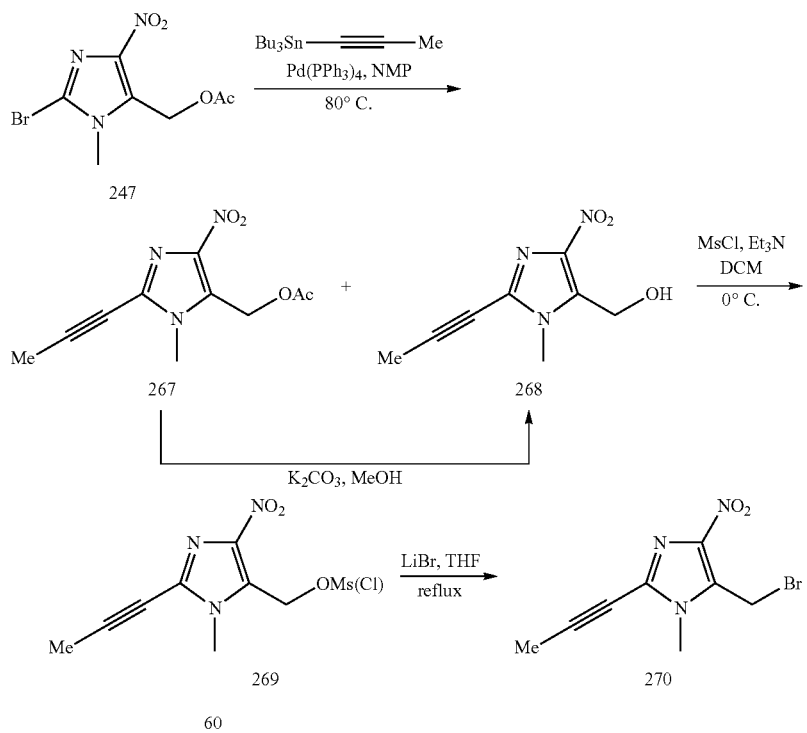

Scheme 9 below illustrates a route to quaternary nitrogen salt compounds of Formula III by reacting an aliphatic tertiary amine-bearing kinase inhibitor of Formula I with an appropriate nitroheterocyclic α-methyl halide/mesylate/tosylate (Formula VIII), in a suitable solvent and for a suitable length of time (for example in N-methyl-2-pyrrolidinone for about 15 hours).

Scheme 9

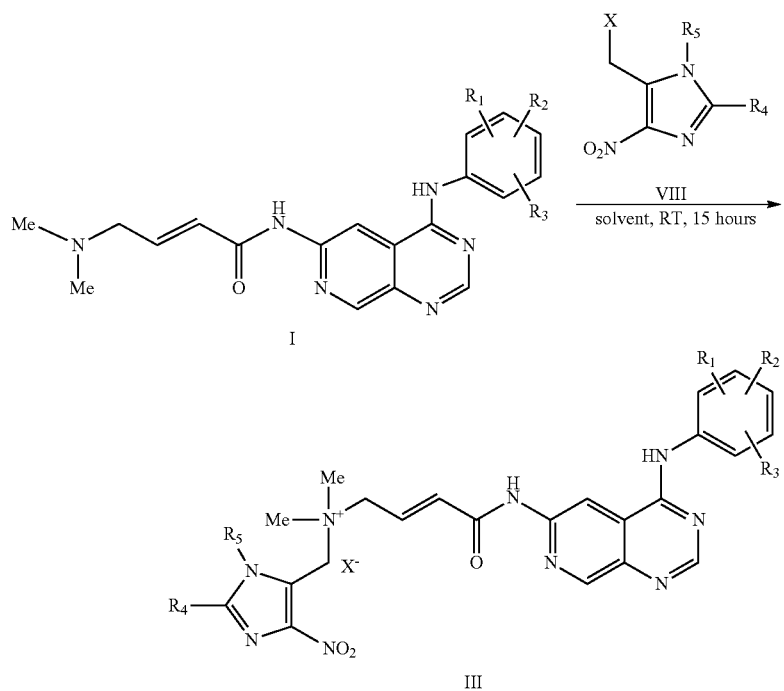

Scheme 10 below illustrates the preparation of a number of prodrug compounds of Formula III according to the invention. The 4-anilinopyrido[3,4-d]pyrimidine effector compounds 1-9 (Scheme 2) were reacted with the α-methyl bromide 239 (Scheme 3) in N-methyl-2-pyrrolidinone (NMP) at room temperature for approximately 15 hours, before the addition of acetonitrile, to provide the quaternary ammonium salts (12, 13, 15-21) as a fine precipitate that was collected by filtration and washed with acetonitrile, ethyl acetate and hexane.

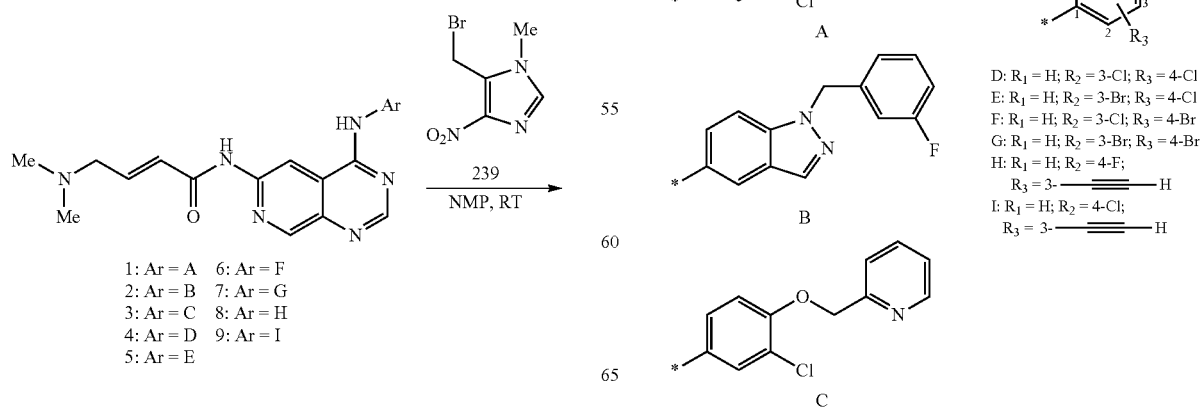

Scheme 11 below illustrates the preparation of a prodrug compound according to the invention.
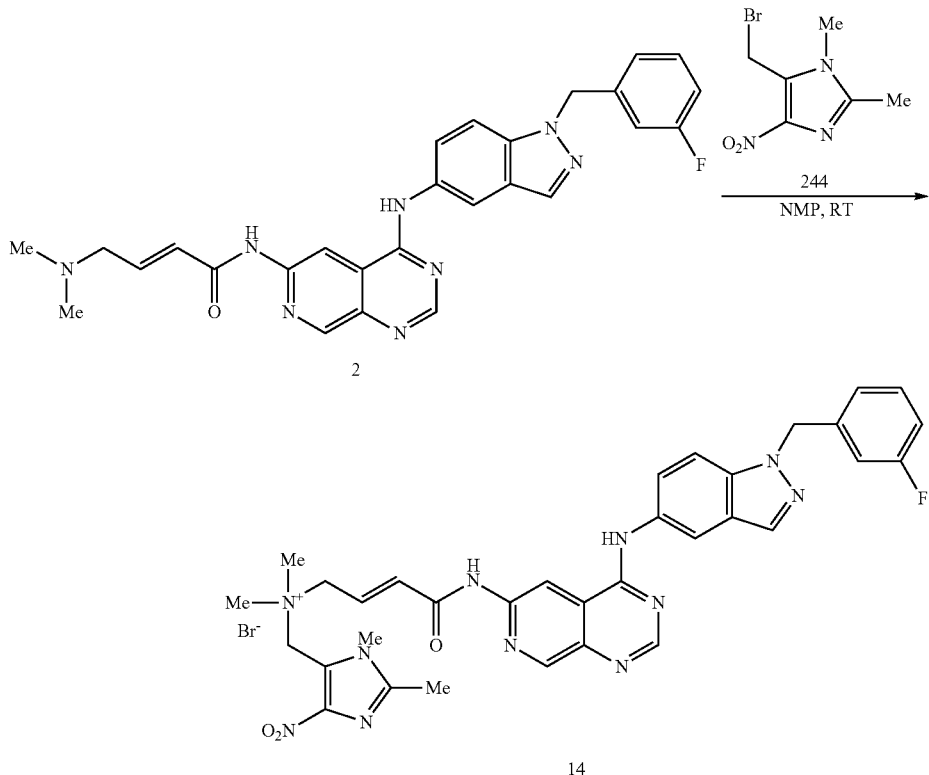
Schemes 12 to 14 below illustrate the preparation of alkyl trigger bromides in which $R_5$ is $C_1$ to $C_6$ alkyl.
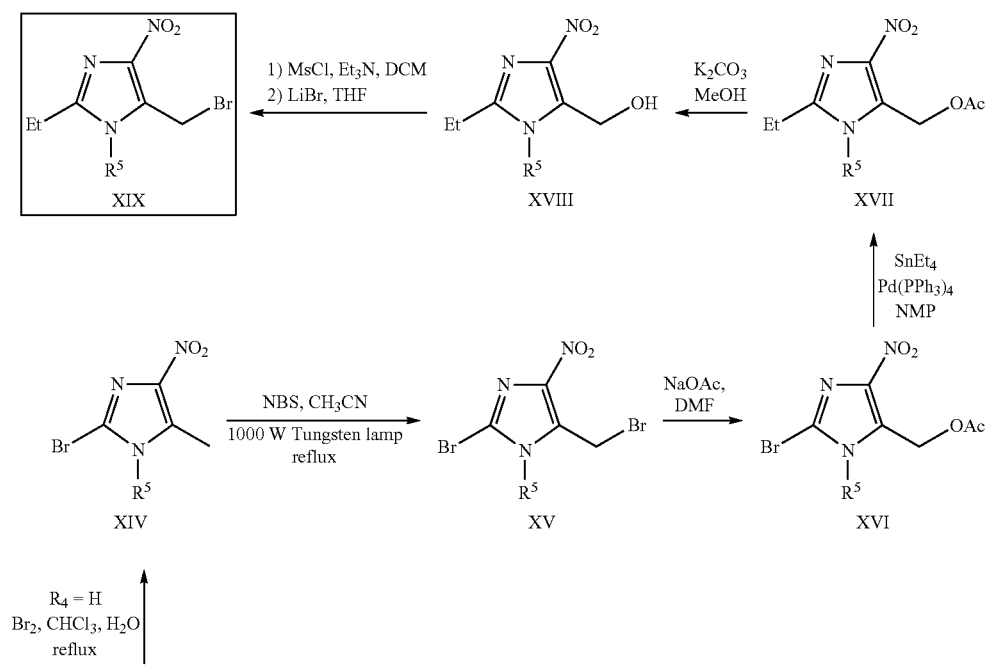

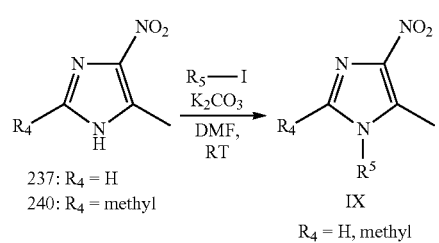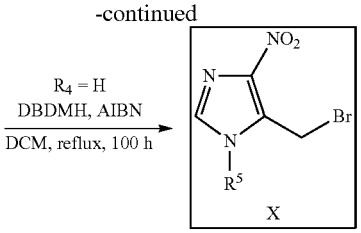
Scheme 13
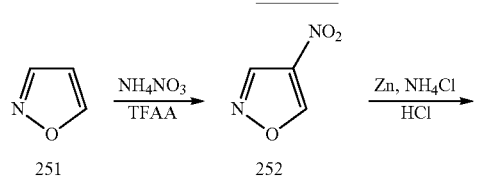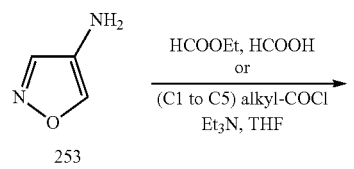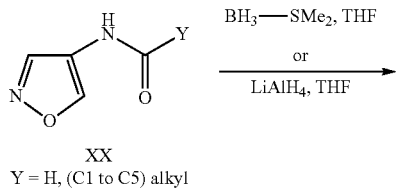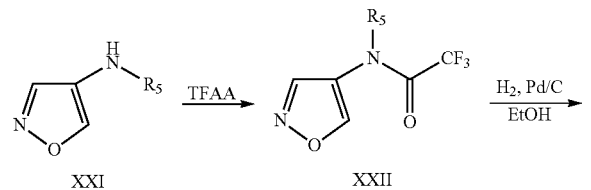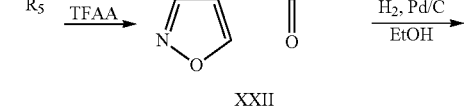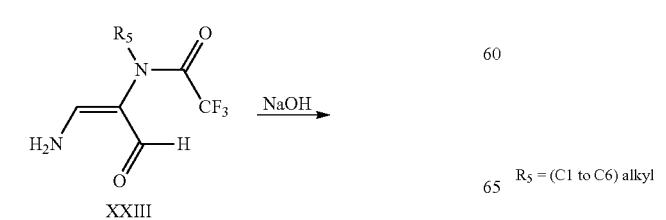
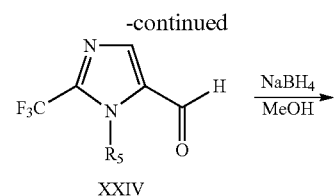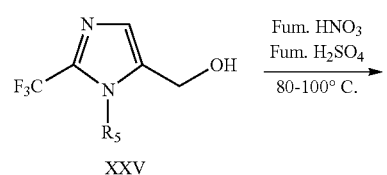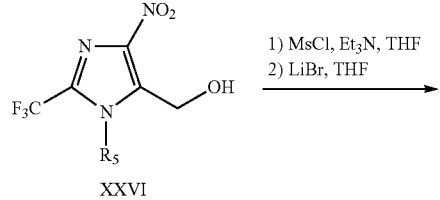
$R_5$ = (C1 to C6) alkyl

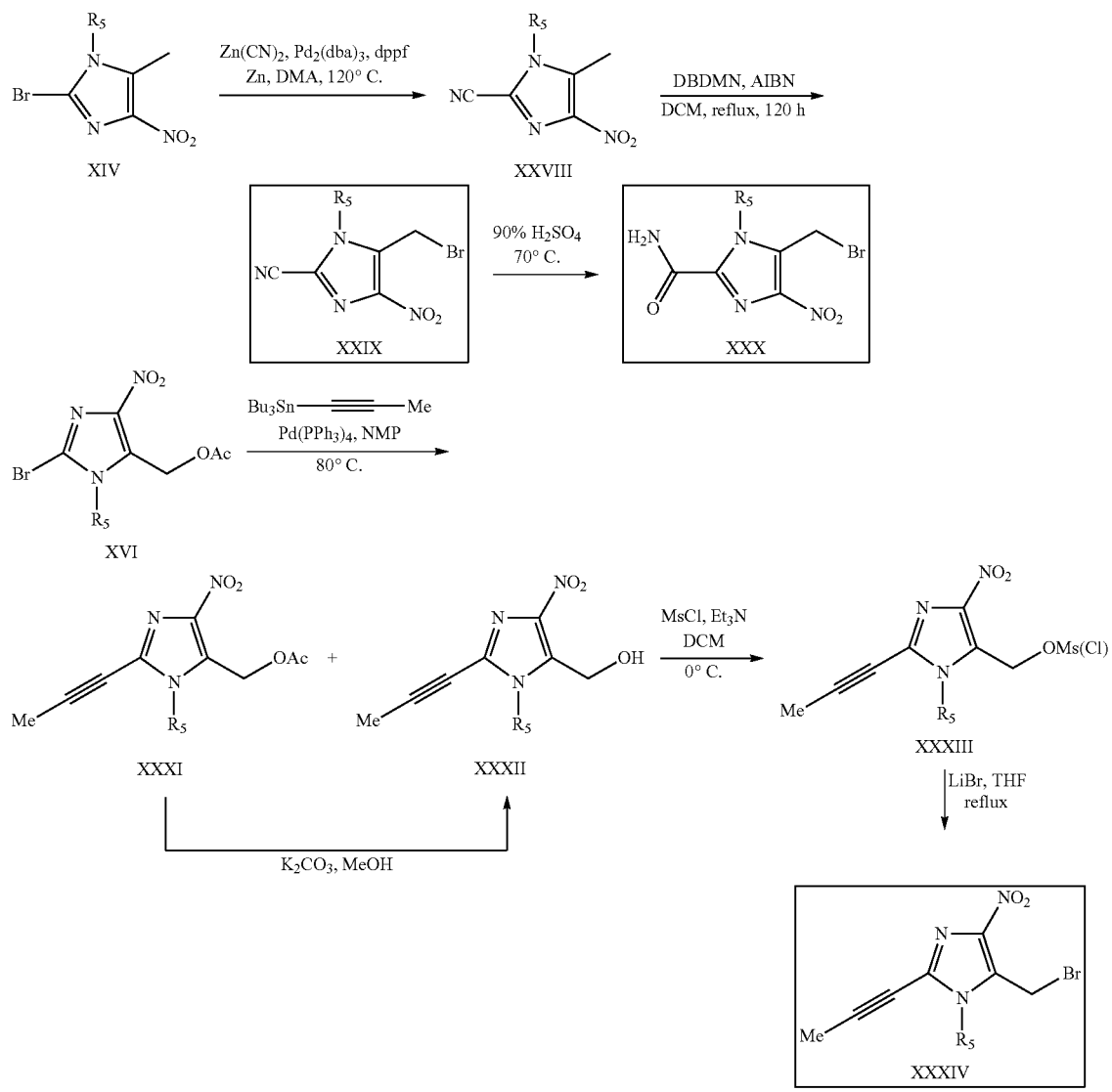

Scheme 14

$R_5$ = (C1 to C6) alkyl

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

EXPERIMENTAL

1. Synthesis 1.1 Chemical Synthesis

Combustion analyses were performed by the Microchemical Laboratory, University of Otago, Dunedin, NZ. Melting points were determined using either an Electrothermal Model 9200 and are as read. $^1$H NMR spectra were measured either on a Bruker Avance-400 spectrometer and are referenced to Me$_4$Si. High resolution mass spectra were recorded on a Varian VG-70SE spectrometer at nominal 5000 resolution. Mass spectrometry was performed on a ThermoFinnigan MSQ single quadrupole mass spectrometer. Mass detection was performed with an APO source, using simultaneous positive and negative ion acquisition. Unless otherwise indicated, compounds were purified by flash column chromatography on Silica gel 60 support (Scharlau, 230-400 mesh ASTM), using the indicated eluants.

1.1.1 The Synthesis of Kinase Inhibitor Effectors 1.1.1.1 Preparation of (2E)-N-(4-{3-chloro-4-[(3-chlorobenzyl)oxy]anilino}pyrido[3,4-d]pyrimidin-6-yl)-4-(dimethylamino)-2-butenamide (1) (Scheme 2)

A heterogeneous mixture of 6-fluoropyrido[3,4-d]pyrimidin-4(3H)-one (200) (1.0 g, 6.06 mmol), thionyl chloride (20 mL) and a catalytic amount of DMF (2 drops) was stirred under reflux for 40 min to give a homogeneous mixture. It was evaporated under reduced pressure at 40° C. (bath temperature) to give a light brown solid. To this solid was added a mixture of 3-chloro-4-(3-chlorobenzyloxy)aniline (1.79 g, 6.67 mmol) and dry DMA (10 mL). The residue of 3-chloro-4-(3-chlorobenzyloxy)aniline was washed down with more DMA (2×2 mL). The reaction mixture was stirred at room temperature for 1 h 30 min. It was partitioned in between ethyl acetate (400 mL) and water (400 mL). The ethyl acetate layer was separated and washed further with water (2×200 mL), dried (MgSO$_4$) and evaporated to give a crude product of N-(3-chloro-4-(3-chlorobenzyloxy)phenyl)-6-fluoropyrido[3,4-d]pyrimidin-4-amine (201). Chromatography on silica gel (dichloromethane/MeOH=25:1) gave pure 201 (2.52 g, 100%) as a yellow/orange solid, mp 196-198° C.; $^1$H NMR δ [(CD$_3$)$_2$SO] 10.03 (s, 1H), 8.94 (s, 1H), 8.69 (s, 1H), 8.21 (s, 1H), 8.07 (d, J=2.5 Hz, 1H), 7.75 (dd, J=9.0, 2.5 Hz, 1H), 7.57-7.54 (m, 1H), 7.49-7.39 (m, 3H), 7.31 (d, J=9.0 Hz, 1H). Anal. Calcd for C$_{20}$H$_{13}$Cl$_2$FN$_4$O: C, 57.85; H, 3.16; N, 13.49. Found C, 57.60; H, 3.45; N, 13.32.

A mixture of compound 201 (2.60 g, 6.27 mmol) and 4-methoxybenzylamine (8.24 mL, 62.7 mmol) in dry DMSO (15 mL) was stirred under a nitrogen atmosphere at 71-72° C. (bath temperature) for 91 h. It was partitioned in between ethyl acetate (500 mL) and water (300 mL). The ethyl acetate layer was separated and washed further with water (3×300 mL); dried (MgSO$_4$) and evaporated to give a crude product of N$^4$-(3-chloro-4-(3-chlorobenzyloxy)phenyl)-N$^6$-(4-methoxybenzyl)prido[3,4-d]pyrimidine-4,6-diamine (210). Chromatography on silica gel (ethyl acetate/petroleum ether=1:1) gave pure 210 (2.02 g, 61%) as a yellow/orange solid, mp 120-122° C.; $^1$H NMR δ [(CD$_3$)$_2$SO] 9.59 (s, 1H), 8.72 (s, 1H), 8.33 (s, 1H), 7.99 (d, J=2.4 Hz, 1H), 7.57-7.53 (m, 1H), 7.48-7.38 (m, 3H), 7.36-7.19 (m, 4H), 7.15 (br s, 1H), 6.91-6.85 (m, 2H), 5.25 (s, 1H), 4.48 (d, J=6.3 Hz, 2H, 3.71 (s, 3H). Anal. Calcd for C$_{28}$H$_{23}$Cl$_2$N$_5$O$_2$: C, 63.16; H, 4.35; N, 13.15. Found C, 62.96; H, 4.63; N, 13.12.

To a stirred heterogeneous mixture of compound 210 (1.46 g, 2.74 mmol) and dry DCM (27 mL) was added trifluoroacetic acid (2.1 mL, 27.4 mmol), followed by anisole (0.60 mL, 5.48 mmol), and the mixture was stirred further at room temperature for 91 h. It was poured into petroleum ether (300 mL) and stirred at room temperature for ca. 30 min. Petroleum ether layer was decanted and discarded. The process was repeated with more petroleum ether (300 mL). The residue left behind was dissolved in mixed solvents of acetone-water=1:1 (ca. 100 mL) and stirred with 5M NH$_3$ (100 mL) at room temperature for 1 h. The solid was filtered and washed successively with acetone-water=1:4 (5×20 mL), petroleum ether-ethyl acetate=3:1 (5×20 mL), and dried to give N$^4$-(3-chloro-4-(3-chlorobenzyloxy)phenyl)pyrido[3,4-d]pyrimidine-4,6-diamine (219) (1.10 g, 97%), mp 251-254° C. (decomp); $^1$H NMR δ [(CD$_3$)$_2$SO] 9.70 (s, 1H), 8.68 (s, 1H), 8.34 (s, 1H), 8.04 (br s, 1H), 7.73 (br d, J=8.0 Hz, 1H), 7.57-7.53 (m, 1H), 7.48-7.39 (m, 3H), 7.26 (d, J=9.0 Hz, 1H), 7.12 (br s, 1H), 7.65 (br s, 2H), 5.24 (s, 2H). Anal. Calcd for C$_{20}$H$_{13}$Cl$_2$N$_5$O: C, 58.27; H, 3.67; N, 16.99. Found C, 58.33; H, 3.57; N, 17.2.

To a stirred mixture of CDI (0.53 g, 3.25 mmol) and dry THF (2 mL), at room temperature and under a nitrogen atmosphere, was added a solution of 2-(diethoxyphosphoryl)acetic acid (0.64 g, 3.25 mmol) in THF (1 mL). After addition the reaction mixture was stirred further at 40° C. (bath) for 15 min (whence evolution of gases ceased). A solution of compound 219 (1.03 g, 2.50 mmol) in a mixed solvents of dry THF (2.5 mL) and DMA (2.5 mL) was added and stirred further at 40° C. The reaction was monitored by TLC (dichloromethane-MeOH=20:1) and found only ca. 60% reaction occurred after 50 min. Thus, another batch of reagent was prepared from CDI [0.53 g, 3.25 mmol; dry THF (2 mL)] and 2-(diethoxyphosphoryl)acetic acid [0.64 g, 3.25 mmol); THF (1 mL)] and added to the reaction. It was stirred further for 3 h at 40° C. The reaction mixture was poured into water (300 mL) and stirred with petroleum ether (400 mL) at room temperature for 12 h. Petroleum ether layer was decanted. More petroleum ether (200 mL) was added and stirred for 15 min. The solid was collected by suction filtration; washed with water (5×20 mL) and dried to give diethyl 2-(4-(3-chloro-4-(3-chlorobenzyloxy)phenylamino)pyrido[3,4-d]pyrimidin-6-ylamino)-2-oxoethylphosphonate (228) (1.37 g, 93%); mp 106-109° C.; $^1$H NMR δ (CDCl$_3$) 9.41 (s, 1H), 9.02 (s, 1H), 8.70 (s, 1H), 8.54 (s, 1 H), 7.91 (d, J=2.6 Hz, 1H), 7.66 (s, 1H), 7.54 (dd, J=8.8, 2.6 Hz, 1H), 7.48 (s, 1H), 7.40-7.29 (m, 3H), 6.99 (d, J=8.9 Hz, 1H), 5.15 (s, 2H), 4.30-4.18 (m, 4H), 3.15 (d, J=21.1 Hz, 2H), 1.39 (t, J=7.0 Hz, 6H). δ [(CD$_3$)$_2$SO]: 10.82 (s, 1H), 10.25 (s, 1H), 8.99 (poorly resolved d, J=0.6 Hz, 1H), 8.41 (s, 1H), 8.58 (s, 1 H), 7.95 (d, J=2.6 Hz, 1H), 7.71 (dd, J=9.0, 2.6 Hz, 1H), 7.56 (br s, 1H), 7.50-7.38 (m, 3H), 7.27 (d, J=9.0 Hz, 1H), 5.26 (s, 2H), 4.15-4.04 (m, 4H), 3.34 (d, partially obscured by water peak, 2H), 1.26 (t, J=7.0 Hz, 6H). Anal. Calcd for C$_{26}$H$_{26}$Cl$_2$N$_5$O$_3$P.0.5H$_2$O: C, 52.10; H, 4.54; N, 11.68%. Found C, 52.09; H, 4.60; N, 11.70%.

To a stirred mixture of 2,2-diethoxy-N,N-dimethylethanamine (1.16 g, 7.20 mmol) and water (1.2 mL) at room temperature and under a nitrogen atmosphere was added an aq. 37% HCl (1.21 mL, 14.4 mmol). After addition the mixture was stirred at 40° C. (bath) for 24 h. It was cooled to 0° C. (bath). This is called solution A. KOH (1.03 g, 18.4 mmol) was dissolved in water (5.5 mL) at room temperature under a nitrogen atmosphere. It was cooled to 0° C. (bath). This is called solution B. To a stirred heterogeneous mixture of compound 228 (1.70 g, 2.88 mmol) and THF (5.5 mL) at room temperature and under a nitrogen atmosphere was added minimum amount of DMA (3 mL) to give a homogeneous solution. LiCl (122 mg, 2.88 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=20:1). After 25 min more KOH (s) (0.34 g, 6.13 mmol) was added and stirred further at 0° C. for another 35 min. It was poured into water (200 mL). Petroleum ether (200 mL) was added and stirred at room temperature for 15 min. Petroleum ether layer was decanted. More petroleum ether (200 mL) was added and stirred for 15 min. The solid was collected by suction filtration; washed with water (4×20 mL); dried under reduced pressure over silica gel/KOH to give (2E)-N-(4-{3-chloro-4-[(3-chlorobenzyl)oxy]anilino}pyrido[3,4-d]pyrimidin-6-yl)-4-(dimethylamino)-2-butenamide (1) (1.28 g, 85%) as a pale yellow solid, mp 195-198; HPLC: 96.8% pure; $^1$H NMR δ [(CD$_3$)$_2$SO] 10.88 (s, 1H), 10.19 (s, 1H), 8.99 (s, 1H), 8.97 (s, 1 H), 8.58 (s, 1H), 7.99 (d, J=2.6 Hz, 1H), 7.73 (dd, J=9.0, 2.6 Hz, 1H), 7.56 (br s, 1H), 7.49-7.38 (m, 3H), 7.27 (d, J=9.0 Hz, 1H), 6.87 (dt, J=15.4, 6.0 Hz, 1H), 6.51 (br d, J=15.4 Hz, 1H), 5.26 (s, 2H), 3.09 (br d, J=6.0 Hz, 2H), 2.19 (s, 6H). Anal. Calcd for C$_{26}$H$_{24}$Cl$_2$N$_6$O$_2$.0.3H$_2$O: C, 59.05; H, 4.69; N, 15.89. Found C, 58.96; H, 4.62; N, 15.73.

1.1.1.2 Preparation of (2E)-4-(dimethylamino)-N-(4-{[1-(3-fluorobenzyl)-1H-indazol-5-yl]amino}pyrido[3,4-d]pyrimidin-6-yl)-2-butenamide (2) (Scheme 2)

A heterogeneous mixture of 6-fluoropyrido[3,4-d]pyrimidin-4(3H)-one (200) (1.65 g, 10.0 mmol), thionyl chloride (30 mL) and a catalytic amount of DMF (2 drops) was stirred under reflux for 5 h to give a homogeneous mixture. It was evaporated under reduced pressure at 45° C. (bath temperature) to give a light brown solid. To this solid was added a solution of 1-(3-fluorobenzyl)-1H-indazol-5-amine (PCT Int. Appl., 2005058245, 30 Jun. 2005) (2.65 g, 11.0 mmol) in dry DMA (15 mL). The residue of 1-(3-fluorobenzyl)-1H-indazol-5-amine was washed down with more DMA (2×2 mL). The reaction mixture was stirred at room temperature for 65 h. It was poured into water (200 mL). The pH was adjusted to ca. 9 using an aqueous solution of $Na_2CO_3$ at room temperature. Petroleum ether (200 mL) was added and stirred at room temperature for 2 h. The petroleum ether layer was decanted. It was repeated once more with petroleum ether (200 mL). The solid was collected by filtration and washed with water (5×25 mL). It was suspended in acetone (80 mL) and stirred at room temperature for 20 min. Water (160 mL) was added and stirred further for 1.5 h. The solid was filtered, dried and finally purified by a silica column (MeOH/dichloromethane: gradient from 0-10%) to give 6-fluoro-N-(1-(3-fluorobenzyl)-1H-indazol-5-yl)pyrido[3,4-d]-pyrimidin-4-amine (202) (3.11 g, 80%) as a pale brown solid, mp 218-221° C.; $^1$H NMR δ [$(CD_3)_2SO$] 10.15 (s, 1H), 8.92 (s, 1H), 8.64 (s, 1H), 8.30 (d, J=1.3 Hz, 1H), 8.28 (br s, 14, 8.19 (poorly resolved d, J=0.7 Hz, 1H), 7.77 (d, J=9.0 Hz, 1H), 7.72 (dd, J=9.0, 1.8 Hz, 1H), 7.42-7.32 (m, 1H), 7.15-7.01 (m, 3H), 5.71 (s, 2H). Anal, Calcd for $C_{21}H_{14}F_2N_6$: C, 64.94; H, 3.63; N, 21.64. Found C, 65.21; H, 3.71; N, 21.63.

A mixture of compound 202 (3.00 g, 7.73 mmol) and 4-methoxybenzylamine (10.2 mL, 77.3 mmol) in dry DMSO (18 mL) was stirred under a nitrogen atmosphere at 68-70° C. (bath temperature) for 165 h. The solution was then cooled and petroleum ether (200 mL) was added. It was stirred at room temperature for 15 min. The layers were allowed to separate and the petroleum ether layer was decanted. This procedure was repeated with more petroleum ether (200 ml). Water (200 mL) was added and the mixture was stirred at room temperature for 45 min. The oil was deposited. Thus, the product was extracted into ethyl acetate; dried ($MgSO_4$) and solvent removed to give a brown oil. It was purified by a silica column (EtOAc/petroleum ether: gradient from 30% to pure EtOAc) to give pure $N^4$-(1-(3-fluorobenzyl)-1H-indazol-5-yl)-$N^6$-(4-methoxybenzyl)pyrido[3,4-d]pyrimidine-4,6-diamine (211) (2.38 g, 61%) as a yellow/orange solid, mp 196-198° C.; $^1$H NMR δ [$(CD_3)_2SO$] 9.75 (s, 1H), 8.72 (s, 1H), 8.29 (s, 1H), 8.22 (poorly resolved d, J=1.3 Hz, 1H), 8.15 (d, J=0.7 Hz, 1H), 7.73 (br d, J=9.0 Hz, 1H), 7.68 (dd, J=9.0, 1.8 Hz, 1H), 7.40-7.31 (m, 3H), 7.24-7.17 (m, 2H), 7.13-7.01 (m, 3H), 6.92-6.84 (m, 2H), 5.70 (s, 2H) 4.49 (d, J=6.3 Hz, 2H), 3.71 (s, 3H). Anal. Calcd for $C_{29}H_{24}FN_7O.1.5H_2O$: C, 65.40; H, 5.11; N, 18.41%. Found C, 65.45; H, 5.07; N, 18.58%.

To a stirred heterogeneous mixture of compound 211 (2.27 g, 4.48 mmol) and DCM (45 ml) was added trifluoroacetic acid (3.45 ml, 44.8 mmol), followed by anisole (0.99 ml, 8.96 mmol), and the mixture was stirred further at room temperature for 5 days. It was poured into petroleum ether (500 ml) and stirred at room temperature for ca. 20 min. Petroleum ether layer was decanted and discarded. The process was repeated with more petroleum ether (300 ml). To the solid left behind was added 5M $NH_3$ (80 ml) at 0° C. and stirred at room temperature for 15 min. The solid was collected and washed successively with water (6×10 ml), petroleum ether-ethyl acetate=3:1 (3×20 ml), and dried to give $N^4$-(1-(3-fluorobenzyl)-1H-indazol-5-yl)pyrido[3,4-d]pyrimidine-4,6-diamine (220) (1.68 g, 97%), mp 241-244° C.; $^1$H NMR δ [$(CD_3)_2SO$] 9.72 (s, 1H), 8.67 (s, 1H), 8.30 (s, 8.27 (br s, 1H), 8.15 (s, 1H), 7.75-7.68 (m, 2H), 7.41-7.33 (m, 14, 7.18 (s, 1H), 7.14-7.01 (m, 3H), 6.20 (s, 2H), 5.69 (s, 2H). Anal. Calcd for $C_{21}H_{16}FN_7.1.5H_2O$: C, 61.16; H, 4.64; N, 23.77. Found C, 61.23; H, 4.71; N, 23.87.

To a stirred mixture of CDI (1.41 g, 8.73 mmol) and dry THF (6 mL), at room temperature and under a nitrogen atmosphere, was added a solution of 2-(diethoxyphosphoryl)acetic acid (1.56 g, 7.94 mmol) in THF (4 mL). After addition the reaction mixture was stirred further at 40° C. (bath) for 15 min (whence evolution of gases ceased). A solution of compound 220 (1.53 g, 3.97 mmol) in a mixed solvents of dry THF (4 mL) and DMA (5 mL) was added and stirred further at 40° C. The reaction was monitored by TLC (dichloromethane-MeOH=15:1). After stirred overnight (16 h), it was found only ca. 70% reaction occurred. Thus, another batch of reagent was prepared from CDI [0.42 g, 2.62 mmol; DCM (3 ml)] and 2-(diethoxyphosphoryl)acetic acid [0.47 g, 2.38 mmol); DCM (2 mL)] and added to the reaction. It was stirred further for 4 h at 40° C. The reaction mixture was poured into water (200 mL) and stirred with petroleum ether (400 mL) at room temperature for 20 min. Petroleum ether layer was decanted. It was repeated once more with petroleum ether (200 mL). The sticky solid was collected by suction filtration; washed with water (5×30 mL). It was dissolved in acetone (50 mL) and stirred with water (100 mL) and petroleum ether (200 mL) at room temperature for 68 h. The solid was collected, washed with acetone/water=1:10 (5×30 mL) and dried to give diethyl 2-(4-(1-(3-fluorobenzyl)-1H-indazol-5-ylamino)pyrido[3,4-d]pyrimidin-6-ylamino)-2-oxoethylphosphonate (229) (1.95 g, 87%); mp 111-114° C.; $^1$H NMR δ [$(CD)_2SO$]: 10.81 (s, 1H), 10.36 (s, 1H), 8.98 (s, 1H), 8.88 (s, 1H), 8.52 (s, 1 H), 8.16 (d, J=0.7 Hz, 1H), 8.13 (d, J=1.3 Hz, 1H), 7.73 (d, J=9.0 Hz, 1H), 7.68 (dd, J=9.0, 1.8 Hz, 1H), 7.42-7.32 (m, 1H), 7.15-7.00 (m, 3H), 5.70 (s, 2 H), 4.17-4.03 (m, 4H), 3.32 (d, partially obscured by water peak, 2H), 1.26 (t, J=7.0 Hz, 6H). Anal. Calcd for $C_{27}H_{27}FN_7O_4P.1.6H_2O$: C, 54.75; H, 5.14; N, 16.55%. Found C, 54.60; H, 5.21; N, 16.60%.

To a stirred mixture of 2,2-diethoxy-N,N-dimethylethanamine (1.32 g, 8.20 mmol) and water (1.4 mL) at room temperature and under a nitrogen atmosphere was added an aq. 37% HCl (1.38 mL, 16.4 mmol). After addition the mixture was stirred at 45° C. (bath) for 25 h. It was cooled to 0° C. (bath). This is called solution A. KOH (2.36 g, 42.0 mmol) was dissolved in water (7 mL) at room temperature under a nitrogen atmosphere. It was cooled to 0° C. (bath). This is called solution B. To a stirred heterogeneous mixture of compound 229 (1.85 g, 3.28 mmol) and THF (7 mL) at room temperature and under a nitrogen atmosphere was added minimum amount of DMA (4 mL) to give a homogeneous solution. LiCl (139 mg, 3.28 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH-10:1). After stirred further for 30 min. it was poured into water (200 mL). Petroleum ether (200 mL) was added and stirred at room temperature for 15 min. Petroleum ether layer was decanted. More petroleum ether (200 mL) was added and stirred for 15 min. The solid was collected by suction filtration; washed with water (4×30 mL); dried under reduced pressure over silica gel/KOH to give (2E)-4-(dimethylamino)-N-(4-{[1-(3-fluorobenzyl)-1H-indazol-5-yl]amino}pyrido[3,4-d]pyrimidin-6-yl)-2-butenamide (2) (1.55 g, 95%) as a pale yellow solid, mp 240-243; HPLC: 96.7% pure; $^1$H NMR δ [$(CD_3)_2SO$] 10.87 (s, 1H), 10.29 (s, 1H), 9.01 (s, 1H), 8.98 (s, 1H), 8.53 (s, 1 H), 8.18 (d, J=0.7 Hz, 1H), 8.16 (d, J=0.4 Hz, 1H), 7.73 (br d, J=9.0 Hz, 1H), 7.70 (dd, J=9.0, 1.7 Hz, 1H), 7.41-7.33 (m, 1H), 7.14-7.02 (m, 3H), 6.87 (dt, J=15.4, 6.0 Hz, 1H), 6.52 (br d, J=15.4 Hz, 1H), 5.70 (s, 2 H), 3.09 (dd, J=6.0, 1.1 Hz, 2H), 2.19 (s, 6H). Anal. Calcd for $C_{27}H_{25}FN_8O.1.2H_2O$: C, 62.59; H, 5.33; N, 21.63%. Found C, 62.59; H, 5.25; N, 21.59%.

1.1.1.3 Preparation of (2E)-N-{4-[3-chloro-4-(2-pyridinylmethoxy)anilino]pyrido[3,4-d]pyrimidin-6-yl}-4-(dimethylamino)-2-butenamide (3) (Scheme 2)

A heterogeneous mixture of 6-fluoropyrido[3,4-d]pyrimidin-4(3H)-one (200) (1.65 g, 10.0 mmol), thionyl chloride (30 ml) and a catalytic amount of DMF (3 drops) was stirred under reflux for 2 h 30 min to give a homogeneous mixture. It was evaporated under reduced pressure at 40° C. (bath temperature) to give a light brown solid. To this solid was added a solution of 3-chloro-4-(pyridin-2-ylmethoxy)aniline (2.58 g, 11.0 mmol) in dry DMA (15 ml). The residue of 3-chloro-4-(pyridin-2-ylmethoxy)aniline was washed down with more DMA (2×5 ml). The reaction mixture was stirred at room temperature for 18 h. It was poured into water (300 ml). The pH was adjusted to ca. 9 using an aqueous solution of $Na_2CO_3$ at room temperature. Petroleum ether (300 mL) was added and stirred at room temperature for 30 min. The petroleum ether layer was decanted. It was repeated once more with petroleum ether (300 mL). The solid was collected by filtration and washed with water (4×50 mL). It was stirred with hot (ca. 50° C.) acetone (300 mL) for 15 min. The insoluble materials was filtered off and the filtrate was evaporated under reduced pressure to give N-(3-chloro-4-(pyridin-2-ylmethoxy)phenyl)-6-fluoropyrido[3,4-d]pyrimidin-4-amine (203) (3.18 g, 83%) as a yellow/orange solid, mp 216-219° C.; $^1$H NMR δ [$(CD_3)_2SO$] 10.04 (s, 1H), 8.94 (s, 1H), 8.69 (s, 1H), 8.63-8.57 (m, 1H), 8.22 (br s, 1H), 8.08 (d, J=2.6 Hz, 1H), 7.85 (td, J=7.7, 1.8 Hz, 1H), 7.75 (dd, J=9.0, 2.6 Hz, 1H), 7.59 (br d, J=7.8 Hz, 1H), 7.40-7.35 (m, 1H), 7.32 (d, J=9.0 Hz, 1H), 5.31 (s, 2H). Anal. Calcd for $C_{19}H_{13}ClFN_5O.0.9H_2O$: C, 57.34; H, 3.75; N, 17.60. Found C, 57.46; H, 3.82; N, 17.63.

A mixture of compound 203 (3.07 g, 8.04 mmol) and 4-methoxybenzylamine (10.6 mL, 80.4 mmol) in dry DMSO (20 mL) was stirred under a nitrogen atmosphere at 70° C. (bath temperature) for 118 h. The mixture was then cooled and petroleum ether (200 mL) was added. It was stirred at room temperature for 15 min. The layers were allowed to separate and the petroleum ether layer was decanted. This procedure was repeated with more petroleum ether (200 ml). Water (200 mL) was added and the mixture was stirred at room temperature overnight (22 h). It was filtered and washed solid with water (5×30 mL), then with petroleum ether (3×30 mL). The sticky yellow/orange solid was stirred with acetone (150 mL) at room temperature for 20 min. Water (150 mL) was added slowly and stirred further at room temperature for 45 min. The fine solid was collected by suction-filtration, washed with water/acetone (1:1) (4×20 mL), petroleum ether (3×20 mL) and dried in vacuum over silica-gel/KOH to give pure $N^4$-(3-chloro-4-(pyridin-2-ylmethoxy)phenyl)-$N^6$-(4-methoxybenzyl)pyrido[3,4-d]pyrimidine-4,6-diamine (212) (3.08 g, 77%) as a yellow/orange solid, mp 182-184° C.; $^1$HNMR δ [$(CD_3)_2SO$] 9.60 (s, 1H), 8.72 (s, 1H), 8.64-8.56 (m, 1H), 8.33 (s, 1H), 8.01 (d, J=2.6 Hz, 1H), 7.88 (td, J=7.7, 1.8 Hz, 1H), 7.71 (dd, J=9.0, 2.6 Hz, 1H), 7.58 (d, J=7.7 Hz), 7.42-7.19 (m, 5H), 7.15 (s, 1H), 6.93-6.84 (m, 2H), 5.25 (s, 2H), 4.48 (d, J=6.3 Hz, 2H), 3.71 (s, 3H). Anal. Calcd for $C_{27}H_{23}ClN_6O_2.0.6aCetO^1le$: C, 64.80; H, 5.02; N, 15.74%. Found C, 64.47; H, 5.00; N, 15.95%.

To a stirred heterogeneous mixture of compound 212 (2.88 g, 5.77 mmol) and DCVI (60 ml) was added trifluoroacetic acid (4.38 ml, 57.7 mmol), followed by anisole (1.27 ml, 11.5 mmol), and the mixture was stirred further at room temperature. After 72 h another batch of trifluoroacetic acid (4.38 ml, 57.7 mmol) was added and stirred further for 49 h. It was poured into petroleum ether (250 ml) and stirred at room temperature for ca. 20 min. Petroleum ether layer was decanted and discarded. The process was repeated with more petroleum ether (250 ml). The solid left behind was dissolved in acetone (150 mL) and 5M $NH_3$ (125 ml) added at 0° C. The mixture was stirred at room temperature for 30 min. The solid was collected and washed successively with acetone/water (1:4) (5×30 ml), petroleum ether/ethyl acetate=3:1 (5×30 ml), and dried to give $N^4$-(3-chloro-4-(pyridin-2-ylmethoxy)phenyl)pyrido[3,4-d]-pyrimidine-4,6-diamine (221) (1.94 g, 89%), mp 247-250° C.; $^1$H NMR. δ [$(CD_3)_2SO$] 9.64 (s, 1H), 8.68 (s, 1H), 8.62-8.56 (m, 1H), 8.33 (s, 1H), 8.06 (d, J=2.6 Hz, 1H), 7.88 (td, J=7.7, 1.8 Hz, 1H), 7.73 (dd, J=9.0, 2.6 Hz, 1H), 7.58 (br d, J=7.8 Hz, 1H), 7.40-7.34 (m, 1H), 7.26 (d, J=9.0 Hz, 1H), 7.12 (s, 1H), 6.23 (s, 2H), 5.29 (s, 2H). Anal. Calcd for $C_{19}H_{13}ClN_6O.1.5H_2O$: C, 56.23; H, 4.47; N, 20.71%. Found C, 56.55; H, 4.45; N, 20.42%.

To a stirred mixture of CDI (2.25 g, 13.9 mmol) and dry THF (9 mL), at room temperature and under a nitrogen atmosphere, was added a solution of 2-(diethoxyphosphoryl)acetic acid (2.43 g, 12.4 mmol) in THF (7 mL). After addition the reaction mixture was stirred further at 40° C. (bath) for 15 min (whence evolution of gases ceased). A mixture of compound 221 (1.88 g, 4.96 mmol) in a mixed solvents of dry THF (10 mL) and DMA (16 mL) was added and stirred further at 40° C. The reaction was monitored by TLC (dichloromethane-MeOH=15:1). After stirred for 17 h, it was poured into water (300 mL) and stirred with petroleum ether (300 mL) at room temperature for 30 min. Petroleum ether layer was decanted. It was repeated once more with petroleum ether (300 mL). The solid was collected by suction filtration; washed with water (5×20 mL) and dried to give diethyl 2-(4-(3-chloro-4-(pyridin-2-ylmethoxy)phenylamino)pyrido[3,4-d]pyrimidin-6-ylamino)-2-oxoethylphosphonate (230) (2.56 g, 93%); mp 113-116° C.; $^1$H NMR δ [$(CD_3)_2SO$]: 10.82 (s, 1H), 10.25 (s, 1H), 8.99 (s, 1H), 8.84 (s, 1H), 8.63-8.56 (m, 214), 7.96 (d, J=2.6 Hz, 1H), 7.88 (td, J=7.7, 1.8 Hz, 1H), 7.70 (dd, J=8.9, 2.6 Hz, 1H), 7.59 (br d, J=7.8 Hz, 1H), 7.41-7.34 (m, 1H), 7.28 (d, J=9.0 Hz, 1H), 4.16-4.03 (m, 4H), 3.31 (d, partially obscured by water peak, 211), 1.26 (t, J=7.0 Hz, 6H). Anal. Calcd for $C_{25}H_{26}ClN_6O_5P.1.2H_2O$: C, 51.90; H, 4.95; N, 14.53%. Found C, 51.85; H, 4.94; N, 14.52%.

To a stirred mixture of 2,2-diethoxy-N,N-dimethylethanamine (1.76 g, 11.0 mmol) and water (1.8 mL) at room temperature and under a nitrogen atmosphere was added an aq. 37% HCl (1.84 mL, 21.9 mmol). After addition the mixture was stirred at 50° C. (bath) for 22 h. It was cooled to 0° C. (bath). This is called solution A. KOH (3.14 g, 56.1 mmol) was dissolved in water (9 mL) at room temperature under a nitrogen atmosphere. It was cooled to 0° C. (bath). This is called solution B. To a stirred heterogeneous mixture of compound 230 (2.44 g, 4.38 mmol) and THE (9 mL) at room temperature and under a nitrogen atmosphere was added minimum amount of DMA (6 mL) to give a homogeneous solution. LiCl (186 mg, 4.38 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=10:1). After stirred for 30 min. it was poured into water (300 mL). Petroleum ether (400 mL) was added and stirred at room temperature for 15 min. Petroleum ether layer was decanted. More petroleum ether (300 mL) was added and stirred for 15 min. The solid was collected by suction filtration; washed with water (4×30 mL); dried under reduced pressure over silica gel/KOH to give compound 3 (1.79 g, 83%) which was found only 87% pure by HPLC. Thus, the sample was stirred with warm MeOH (200 mL) for 30 min and cooled to room temperature. The insoluble materials were filtered off and to the filtrates was added one volume of water to precipitate out the required product. The solid was collected, washed with water/MeOH=1:1 several times and dried to give (2E)-N-{4-[3-chloro-4-(2-pyridinylmethoxy)anilino]pyrido[3,4-d]pyrimidin-6-yl}-4-(dimethylamino)-2-butenamide (3) (1.54 g, 72%) as a pale yellow solid, mp 196-199; HPLC: 94.6% pure; $^1$H NMR δ [(CD$_3$)$_2$SO] 10.88 (s, 1H), 10.19 (s, 1H), 8.99 (s, m), 8.64-8.55 (m, 2H), 8.00 (d, J=2.5 Hz, 1H), 7.88 (td, J=7.7, 1.8 Hz, 1H), 7.73 (br dd, J=8.9, 2.5 Hz, 1H), 7.59 (br d, J=7.8 Hz, 1H), 7.41-7.34 (m, 1H), 7.28 (d, J=9.0 Hz, 1H), 6.87 (dt, J=15.4, 6.1 Hz, 1H), 6.51 (br d, J=15.4 Hz, 1H), 5.30 (s, 2 H), 3.09 (dd, J=6.1, 1.2 Hz, 2H), 2.19 (s, 6H). Anal. Calcd for C$_{25}$H$_{24}$ClN$_7$O$_2$.1.5H$_2$O: C, 58.08; H, 5.26; N, 18.97%. Found C, 58.17; H, 5.36; N, 19.00%.

1.1.1.4 Preparation of (2E)-N-[4-(3,4-dichloroanilino)pyrido[3,4-d]pyrimidin-6-yl]-4-(dimethylamino)-2-butenamide (4) (Scheme 2)

A heterogeneous mixture of 6-fluoropyrido[3,4-d]pyrimidin-4(3H)-one (200) (1.50 g, 9.09 mmol), thionyl chloride (20 ml) and a catalytic amount of DMF (2 drops) was stirred under reflux for 1.5 h to give a homogeneous mixture. It was evaporated under reduced pressure at 50° C. (bath temperature) to give a light brown solid. To this solid was added a solution of 3,4-dichloroaniline (1.62 g, 10.0 mmol) in dry DMA (15 mL). The residue of 3,4-dichloroaniline was washed down with more DMA (2×2 ml). The reaction mixture was stirred at room temperature for 20 h. It was poured into water (200 mL). The pH was adjusted to ca. 8 using an aqueous solution of Na$_2$CO$_3$ at room temperature. Petroleum ether (300 mL) was added and stirred at room temperature for 30 min. The petroleum ether layer was decanted. It was repeated once more with petroleum ether. The solid was collected by filtration and washed with water (5×25 mL). It was dried in vacuum over silica gel/KOH overnight to give N-(3,4-dichlorophenyl)-6-fluoropyrido[3,4-d]pyrimidin-4-amine (204) (2.81 g, 100%) as a yellow/orange solid, mp 262-264° C.; $^1$H NMR δ [(CD$_3$)$_2$SO] 10.17 (s, 1H), 8.99 (s, 1H), 8.79 (s, 1H), 8.35 (d, J=2.5 Hz, 1H), 8.26 (poorly resolved d, J=0.7 Hz, 1H), 7.92 (dd, J=8.8, 2.5 Hz, 1H), 7.69 (d, J=8.8 Hz, 1H). Anal. Calcd for C$_{13}$H$_7$Cl$_2$FN$_4$: C, 50.51; H, 2.28; N, 18.12. Found C, 50.50; H, 2.27; N, 18.42.

A mixture of compound 204 (2.95 g, 9.55 mmol) and 4-methoxybenzylamine (12.6 mL, 95.5 mmol) in dry DMSO (20 mL) was stirred under a nitrogen atmosphere at 52° C. (bath temperature) for 10 days. The solution was then cooled and petroleum ether (200 mL) was added. It was stirred at room temperature for 10 min. The layers were allowed to separate and the petroleum ether layer was decanted. This procedure was repeated with more petroleum ether (2×200 ml). Water (200 mL) was added and the mixture was stirred at room temperature for 15 min. It was filtered and washed solid with water (5×30 mL), then with petroleum ether (3×30 mL). The sticky yellow/orange solid was stirred with acetone (100 mL) at 35-45° C. (internal temperature) for 10 min. Water (100 mL) was added and stirred at room temperature for 20 min. The solid was collected by suction-filtration, washed with water/acetone (1:1) (5×20 mL), and dried in vacuum over silica-gel/KOH to give pure N$^4$-(3,4-dichlorophenyl)-N$^6$-(4-methoxybenzyl)pyrido[3,4-d]pyrimidine-4,6-diamine (213) (2.59 g, 64%) as a yellow/orange solid, mp 209-211° C.; $^1$H NMR δ [(CD$_3$)$_2$SO] 9.76 (s, 1H), 8.77 (s, 1H), 8.42 (s, 1H), 8.30 (poorly resolved d, J=2.1 Hz, 1H), 7.89 (dd, J=8.8, 2.1 Hz, 1H), 7.64 (d, J=8.8 Hz, 1H), 7.38-7.25 (m, 3H), 7.17 (s, 1H), 6.92-6.83 (m, 2H), 4.49 (d, J=6.3 Hz, 2H), 3.71 (s, 3H). Anal. Calcd for C$_{21}$H$_{17}$Cl$_2$N$_5$O: C, 59.17; H, 4.02; N, 16.43%. Found C, 58.93; H, 4.17; N, 16.12%.

To a stirred heterogeneous mixture of compound 213 (2.50 g, 5.86 mmol) and DCM (60 ml) was added trifluoroacetic acid (4.49 ml, 58.6 mmol), followed by anisole (1.28 mL, 11.7 mmol), and the mixture was stirred further at room temperature for 43 h. It was poured into petroleum ether (600 mL) and stirred at room temperature for ca. 20 min. Petroleum ether layer was decanted and discarded. The process was repeated with more petroleum ether (300 mL). To the solid left behind was added 5M NH$_3$ (80 mL) at 0° C. and stirred at room temperature for 15 min. The solid was collected and washed successively with water (6×10 mL), petroleum ether-ethyl acetate=3:1 (3×20 mL), and dried to give N$^4$-(3,4-dichlorophenyl)pyrido[3,4-d]pyrimidine-4,6-diamine (222) (1.76 g, 98%), mp 277-280° C.; $^1$H NMR δ [(CD$_3$)$_2$SO] 9.83 (s, 1H), 8.73 (s, 1H), 8.42 (s, 1H), 8.34 (d, J=2.5 Hz, 1H), 7.92 (dd, J=8.8, 2.5 Hz, 1H), 7.63 (d, J=8.8 Hz, 1H), 7.14 (s, 1H), 6.30 (s, 2H). Anal. Calcd for C$_{13}$H$_9$Cl$_2$N$_5$.0.5H$_2$O: C, 49.54; H, 3.20; N, 22.22. Found C, 49.70; H, 3.08; N, 22.28.

To a stirred mixture of CDI (1.98 g, 12.2 mmol) and dry THF (8 mL), at room temperature and under a nitrogen atmosphere, was added a solution of 2-(diethoxyphosphoryl)acetic acid (2.18 g, 11.1 mmol) in THF (6 mL). After addition the reaction mixture was stirred further at 40° C. (bath) for 15 min (whence evolution of gases ceased). A solution of compound 222 (1.70 g, 5.56 mmol) in a mixed solvents of dry THF (6 mL) and DMA (7 mL) was added and stirred further at 40° C. The reaction was monitored by TLC (dichloromethane-MeOH=15:1). After stirred overnight (17 h), the reaction mixture was poured into water (300 mL) and stirred with petroleum ether (400 mL) at room temperature for 20 min. Petroleum ether layer was decanted. It was repeated once more with petroleum ether (400 mL). The solid was collected by suction filtration; washed with water (5×30 mL) and dried to give diethyl 2-(4-(3,4-dichlorophenylamino)pyrido[3,4-d]pyrimidin-6-ylamino)-2-oxoethylphosphonate (231) (2.56 g, 95%); mp 121-124° C.; $^1$H NMR δ [(CD$_3$)$_2$SO]: 10.86 (s, 10.42 (s, 1H), 9.04 (s, 1H), 8.87 (s, 1H), 8.67 (s, 1 H), 8.24 (d, J=2.2 Hz, 1H), 7.89 (dd, J=8.8, 2.2 Hz, 1H), 7.65 (d, J=8.8 Hz, 1H), 4.16-4.04 (m, 4H), 3.32 (d, partially obscured by water peak, 2H), 1.26 (t, J=7.0 Hz, 6H). Anal. Calcd for C$_{19}$H$_{20}$Cl$_2$N$_5$O$_4$P.H$_2$O: C, 45.43; H, 4.42; N, 13.94%. Found C, 45.37; H, 4.20; N, 13.81%.

To a stirred mixture of 2,2-diethoxy-N,N-dimethylethanamine (2.08 g, 12.9 mmol) and water (2.2 mL) at room temperature and under a nitrogen atmosphere was added an aq. 37% HCl (2.16 mL, 25.7 mmol). After addition the mixture was stirred at 40° C. (bath) for 20 h. It was cooled to 0° C. (bath). This is called solution A. KOH (1.84 g, 32.9 mmol) was dissolved in water (10 mL) at room temperature under a nitrogen atmosphere. It was cooled to 0° C. (bath). This is called solution B. To a stirred heterogeneous mixture of compound 231 (2.49 g, 5.14 mmol) and THF (10 mL) at room temperature and under a nitrogen atmosphere was added minimum amount of DMA (5.5 mL) to give a homogeneous solution. LiCl (218 mg, 5.14 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=10:1). After 15 min it was found ca. 20% of compound 231 left. More KOH (0.40 g, 7.14 mmol) was added as a solid. After stirred further for 15 min. it was poured into water (300 mL). Petroleum ether (300 mL) was added and stirred at room temperature for 15 min. Petroleum ether layer was decanted. More petroleum ether (300 mL) was added and stirred for 15 min. The solid was collected by suction filtration; washed with water (4×30 mL); dried under reduced pressure over silica gel/KOH to give (2E)-N-[4-(3,4-dichloroanilino)pyrido[3,4-d]-pyrimidin-6-yl]-4-(dimethylamino)-2-butenamide (4) (2.03 g, 95%) as a beige solid, mp 161-164° C.; HPLC: 98.6% pure; $^1$N NMR δ [(CD$_3$)$_2$SO] 10.92 (s, 1H), 10.36 (s, 1H), 9.09-8.95 (m, 2H), 8.67 (br s, 1 H), 8.27 (br s, 1 H), 7.92 (br d, J=7.8 Hz, 1H), 7.65 (d, J=8.8, 1H), 6.88 (dt, J=15.4, 6.0 Hz, 1H), 6.52 (br d, J=15.4 Hz, 1H), 3.09 (dd, J=6.0, 1.2 Hz, 2H), 2.19 (s, 6H). Anal. Calcd for C$_{19}$H$_{18}$Cl$_2$N$_6$O.1.2H$_2$O: C, 51.99; H, 4.69; N, 19.15. Found C, 51.93; H, 4.59; N, 19.15.

1.1.1.5 Preparation of (2E)-N-[4-(3-bromo-4-chloroanilino)pyrido[3,4-d]pyrimidin-6-yl]-4-(dimethylamino)-2-butenamide (5) (Scheme 2)

A heterogeneous mixture of 6-fluoropyrido[3,4-d]pyrimidin-4(3H)-one (200) (1.50 g, 9.09 mmol), thionyl chloride (20 mL) and a catalytic amount of DMF (2 drops) was stirred under reflux for 3 h to give a homogeneous mixture. It was evaporated under reduced pressure at 40° C. (bath temperature) to give a light brown solid. To this solid was added a solution of 3-bromo-4-chloroaniline (2.07 g, 10.0 mmol) in dry DMA (15 mL). The residue of 3-bromo-4-chloroaniline was washed down with more DMA (2×2 mL). The reaction mixture was stirred at room temperature for 19 h. It was poured into water (200 mL). The pH was adjusted to ca. 8 using an aqueous solution of Na$_2$CO$_3$ at room temperature. Petroleum ether (300 mL) was added and stirred at room temperature for 30 min. The petroleum ether layer was decanted. It was repeated once more with petroleum ether. The solid was collected by filtration and washed with water (4×20 mL). It was dried in vacuum over silica gel/KOH overnight to give N-(3-bromo-4-chlorophenyl)-6-fluoropyrido[3,4-d]pyrimidin-4-amine (205) (3.20 g, 99%) as a yellow/orange solid, mp 271-275° C.; $^1$H NMR δ [(CD$_3$)$_2$SO] 10.15 (s, 1H), 8.99 (s, 1H), 8.79 (s, 1H), 8.45 (d, J=2.5 Hz, 1H), 8.26 (br s, 1H), 7.98 (dd, J=8.8, 2.5 Hz, 1H), 7.69 (d, J=8.8 Hz, 11-1). Anal. Calcd for C$_{13}$N$_7$BrClFN$_4$: C, 44.16; H, 2.00; N, 15.85. Found C, 44.21; H, 1.87; N, 15.98.

A mixture of compound 205 (3.09 g, 8.74 mmol) and 4-methoxybenzylamine (11.5 mL, 87.4 mmol) in dry DMSO (20 mL) was stirred under a nitrogen atmosphere at 58-60° C. (bath temperature) for a week. The solution was then cooled and petroleum ether (300 mL) was added. It was stirred at room temperature for 20 min. The layers were allowed to separate and the petroleum ether layer was decanted. This procedure was repeated once more with petroleum ether (300 mL). Water (250 mL) was added and the mixture was stirred at room temperature for 20 h. The yellow/orange solid was collected by filtration and washed with water (5×20 mL), then with petroleum ether (3×30 mL). The sticky yellow/orange solid was dissolved in acetone (150 mL) at 45° C. (bath temperature). It was filtered to remove insoluble impurities. To the filtrate was added water (400 mL) and stirred at room temperature for 1 h. The solid was collected by suction-filtration, washed with water (5×25 mL), petroleum ether (3×30 mL), and dried in vacuum over silica-gel/KOH to give pure N$^4$-(3-bromo-4-chlorophenyl)-N$^6$-(4-methoxybenzyl)pyrido[3,4-d]pyrimidine-4,6-diamine (214) (3.01 g, 73%) as a greenish yellow solid, mp 207-210° C.; $^1$H NMR δ [(CD)$_2$SO] 9.74 (s, 1H), 8.77 (s, 1H), 8.41 (s, 1H), 8.39 (d, J=2.4 Hz, 1H), 7.96 (dd, J=8.8, 2.4 Hz, 1H), 7.64 (d, J=8.8 Hz, 1H), 7.38-7.25 (m, 3H), 7.17 (s, 1H), 6.92-6.85 (m, 2H), 4.49 (d, J=6.3 Hz, 3.71 (s, 3H). Anal. Calcd for C$_{21}$H$_{17}$BrClN$_5$O: C, 53.58; H, 3.64; N, 14.88%. Found C, 53.84; H, 3.55; N, 14.63%.

To a stirred heterogeneous mixture of compound 214 (2.92 g, 6.20 mmol) and DCM (60 mL) was added trifluoroacetic acid (4.75 mL, 62.0 mmol), followed by anisole (1.36 mL, 12.4 mmol), and the mixture was stirred further at room temperature for 42 h. It was poured into petroleum ether (600 mL) and stirred at room temperature for ca. 20 min. Petroleum ether layer was decanted and discarded. The process was repeated with more petroleum ether (300 mL). To the solid left behind was added 5M NH$_3$ (80 mL) at 0° C. and stirred at room temperature for 15 min. The solid was collected and washed successively with water (6×10 mL), petroleum ether-ethyl acetate=3:1 (3×20 mL), and dried to give N$^4$-(3-bromo-4-chlorophenyl)pyrido[3,4-d]-pyrimidine-4,6-diamine (223) (2.17 g, 100%), mp 271-274° C.; $^1$H NMR δ [(CD$_3$)$_2$SO] 9.82 (s, 1H), 8.72 (s, 1H), 8.44 (d, J=2.3 Hz, 1H), 8.42 (s, 1H), 7.97 (dd, J=8.8, 2.3 Hz, 1H, 7.62 (d, J=8.8 Hz, 1H), 7.14 (s, 1H), 6.30 (s, 2H). Anal. Calcd for C$_{13}$H$_9$BrClN$_5$.0.6H$_2$O: C, 43.20; H, 2.85; N, 19.38. Found C, 43.00; H, 2.95; N, 19.12.

To a stirred mixture of CDI (1.20 g, 7.42 mmol) and dry THF (5 mL), at room temperature and under a nitrogen atmosphere, was added a solution of 2-(diethoxyphosphoryl)acetic acid (1.45 g, 7.42 mmol) in THF (4 mL). After addition the reaction mixture was stirred further at 40° C. (bath) for 15 min (whence evolution of gases ceased). A solution of compound 223 (2.00 g, 5.71 mmol) in a mixed solvents of dry THF (6 mL) and DMA (7 mL) was added and stirred further at 40° C. The reaction was monitored by TLC (dichloromethane-MeOH=10:1) and found only ca. 60% reaction occurred after 1 h. Thus, another batch of reagent was prepared from CDI [0.87 g, 5.37 mmol; dry THF (2.5 mL)] and 2-(diethoxyphosphoryl)acetic acid [0.72 g, 5.37 mmol); THF (3 mL)] and added to the reaction. It was stirred further for 3 h at 40° C. The reaction mixture was poured into water (300 mL) and stirred with petroleum ether (400 mL) at room temperature for 20 min. Petroleum ether layer was decanted. It was repeated once more with petroleum ether (400 mL). The solid was collected by suction filtration; washed with water (5×30 mL) and dried to give diethyl 2-(4-(3-bromo-4-chlorophenylamino)pyrido[3,4-d]pyrimidin-6-ylamino)-2-oxoethylphosphonate (232) (2.85 g, 94%); mp 113-116° C.; $^1$H NMR δ [(CD$_3$)$_2$SO]: 10.86 (s, 1H), 10.40 (s, 1H), 9.04 (s, 1H), 8.87 (s, 1H), 8.67 (s, 1 H), 8.34 (d, J=2.3 Hz, 1H), 7.94 (dd, J=8.8, 2.3 Hz, 1H), 7.65 (d, J=8.8 Hz, 1H), 4.16-4.03 (m, 4H), 3.32 (d, partially obscured by water peak, 2H), 1.26 (t, J=7.1 Hz, 6H). Anal. Calcd for C$_{19}$H$_{20}$BrClN$_5$O$_4$P.H$_2$O: C, 41.74; H, 4.06; N, 12.81%. Found C, 42.01; H, 3.90; N, 12.78%.

To a stirred mixture of 2,2-diethoxy-N,N-dimethylethanamine (2.11 g, 13.1 mmol) and water (2.2 mL) at room temperature and under a nitrogen atmosphere was added an aq. 37% HCl (2.19 mL, 26.1 mmol). After addition the mixture was stirred at 40° C. (bath) for 21 h. It was cooled to 0° C. (bath). This is called solution A. KOH (1.87 g, 33.4 mmol) was dissolved in water (10 mL) at room temperature under a nitrogen atmosphere. It was cooled to 0° C. (bath). This is called solution B. To a stirred heterogeneous mixture of compound 232 (2.76 g, 5.22 mmol) and THF (10 mL) at room temperature and under a nitrogen atmosphere was added minimum amount of DMA (5.5 mL) to give a homogeneous solution. LiCl (221 mg, 5.22 mmol) was added and stirred at 0° C. (bath) for 15 min, The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=10:1). After 35 min, it was poured into water (300 mL). Petroleum ether (300 mL) was added and stirred at room temperature for 15 min. Petroleum ether layer was decanted. More petroleum ether (300 mL) was added and stirred for 15 min. The solid was collected by suction filtration; washed with water (4×30 mL); dried under reduced pressure over silica gel/KOH to give (2E)-N-[4-(3-bromo-4-chloroanilino)pyrido[3,4-d]pyrimidin-6-yl]-4-(dimethylamino)-2-butenamide (5) (2.37 g, 98%) as a pale yellow solid, mp 168-171; HPLC: 96.8% pure; $^1$H NMR δ [(CD$_3$)$_2$SO] 10.92 (s, 1H), 10.34 (s, 1H), 9.10-8.95 (m, 2H), 8.67 (br s, 1 H), 8.38 (br s, 1 H), 7.97 (br d, J=8.3 Hz, 1H), 7.65 (d, J=8.8, 1H), 6.88 (dt, J=15.4, 6.0 Hz, 1H), 6.52 (br d, J=15.4 Hz, 1H), 3.09 (dd, J=6.0, 1.1 Hz, 2H), 2.19 (s, 6H). Anal. Calcd for C$_{19}$H$_{18}$BrClN$_6$O.H$_2$O: C, 47.57; H, 4.20; N, 17.52. Found C, 47.80; H, 4.25; N, 17.51.

1.1.1.6 Preparation of (2E)-N-[4-(4-bromo-3-chloroanilino)pyrido[3,4-d]pyrimidin-6-yl]-4-(dimethylamino)-2-butenamide (6) (Scheme 2)

A heterogeneous mixture of 6-fluoropyrido[3,4-d]pyrimidin-4(3H)-one (200) (1.65 g, 10.0 mmol), thionyl chloride (20 mL) and a catalytic amount of DMF (2 drops) was stirred under reflux for 3 h to give a homogeneous mixture. It was evaporated under reduced pressure at 50° C. (bath temperature) to give a light brown solid. To this solid was added a solution of 4-bromo-3-chloroaniline (2.27 g, 11.0 mmol) in dry DMA (15 mL). The residue of 4-bromo-3-chloroaniline was washed down with more DMA (2×2 mL). The reaction mixture was stirred at room temperature for 18 h. It was poured into water (250 ml). The pH was adjusted to ca. 8 using an aqueous solution of Na$_2$CO$_3$ at room temperature. Petroleum ether (300 mL) was added and stirred at room temperature for 1 h. The petroleum ether layer was decanted. It was repeated once more with petroleum ether, The solid was collected by filtration and washed with water (4×20 mL). It was dried in vacuum over silica gel/KOH overnight to give N-(4-bromo-3-chlorophenyl)-6-fluoropyrido[3,4-a]pyrimidin-4-amine (206) (3.31 g, 94%) as a beige solid, mp 258-261° C.; $^1$H NMR δ [(CD$_3$)$_2$SO] 10.17 (s, 1H), 8.99 (s, 1H), 8.79 (s, 1H), 8.35 (br s, 1H), 8.27 (s, 1H), 7.93-7.74 (m, 2H). Anal. Calcd for C$_{13}$H$_7$BrClFN$_4$: C, 44.16; H, 2.00; N, 15.85. Found C, 43.96; H, 1.96; N, 15.60.

A mixture of compound 206 (3.22 g, 9.11 mmol) and 4-methoxybenzylamine (11.95 mL, 91.1 mmol) in dry DMSO (24 mL) was stirred under a nitrogen atmosphere at 70° C. (bath temperature) for 113 h. The solution was then cooled and stirred with petroleum ether (300 mL) at room temperature for 20 min. The layers were allowed to separate and the petroleum ether layer was decanted. This procedure was repeated once more with petroleum ether (300 mL). Water (300 mL) was added and the mixture was stirred at room temperature for 4 h. The solid was collected by filtration and washed with water (4×20 mL). The sticky yellow/orange solid was dissolved in acetone (80 mL) at 40° C. (bath temperature). Water (80 mL) was added and stirred at room temperature for 10 min.

The solid was collected by suction-filtration, washed with acetone/water=1:1 (5×20 mL) and dried in vacuum over silica-gel/KOH to give pure N$^4$ (4-bromo-3-chlorophenyl)-N$^6$-(4-methoxybenzyl)pyrido[3,4-a]pyrimidine-4,6-diamine (215) (3.63 g, 85%) as a greenish yellow solid, mp 175-177° C.; $^1$H NMR δ [(CD$_3$)$_2$SO] 9.77 (s, 1H), 8.77 (s, 1H), 8.42 (s, 1H), 8.30 (br s, 1H), 7.83 (br d, J=8.2, 1H), 7.77 (d, J=8.7 Hz, 1H), 7.43-7.26 (m, 3H), 7.17 (s, 1H), 6.88 (br d, J=8.3 Hz, 2H), 4.49 (d, J=5.6 Hz, 2H), 3.71 (s, 3H). Anal. Calcd for C$_{21}$H$_{17}$BrClN$_5$O.acetone; C, 54.51; H, 4.38; N, 13.24%. Found C, 54.83; H, 4.31; N, 13.15%.

To a stirred heterogeneous mixture of compound 215 (3.55 g, 7.56 mmol) and DCIVI (75 mL) was added trifluoroacetic acid (5.82 mL, 75.6 mmol), followed by anisole (1.66 mL, 15.1 mmol), and the mixture was stirred further at room temperature for 46 h. It was poured into petroleum ether (400 mL) and residue washed down with MeOH. After stirred at room temperature for ca. 20 min. Petroleum ether layer was decanted and discarded. The process was repeated with more petroleum ether (400 mL). To the solid left behind was added 5M NH$_3$ (100 mL) at 0° C. and stirred at room temperature for 15 min. The solid was collected and washed with water (5×20 mL) and dried to give N$^4$-(4-bromo-3-chlorophenyl)pyrido [3,4-d]-pyrimidine-4,6-diamine (224) (2.41 g, 91%), mp 272-275° C.; $^1$H NMR δ [(CD$_3$)$_2$SO] 9.83 (s, 1H), 8.73 (s, 1H), 8.42 (s, 1H), 8.34 (d, J=2.0 Hz, 1H), 7.84 (dd, J=8.8, 2.0 Hz, 1H), 7.75 (d, J=8.8 Hz, 1H), 7.14 (s, 1H), 6.31 (s, 24. Anal, Calcd for C$_{13}$H$_9$BraN$_5$.0.2MeOH: C, 45.15; H, 2.73; N, 19.36. Found C, 44.84; H, 2.52; N, 19.29.

To a stirred mixture of CDI (2.97 g, 18.3 mmol) and dry THF (12 mL), at room temperature and under a nitrogen atmosphere, was added a solution of 2-(diethoxyphosphoryl) acetic acid (3.2 g, 16.3 mmol) in THF (10 mL). After addition the reaction mixture was stirred further at 40° C. (bath) for 15 min (whence evolution of gases ceased). A solution of compound 224 (2.29 g, 6.53 mmol) in a mixed solvents of dry THF (8 mL) and DMA (9 mL) was added and stirred further at 40° C. The reaction was monitored by TLC (dichloromethane-MeOH=10:1) and found ca. 80% reaction occurred after 3 h. Thus, another batch of reagent was prepared from EDI [0.59 g, 3.66 mmol; dry THF (2.5 mL)] and 2-(diethoxyphosphoryl)acetic acid [0.64 g, 3.26 mmol); THF (2 mL)] and added to the reaction mixture. It was stirred further for 1 h at 40° C. The reaction mixture was poured into water (500 mL) and stirred with petroleum ether (500 mL) at room temperature overnight. Petroleum ether layer was decanted. It was stirred with more petroleum ether (300 mL) for 10 min. The solid was collected by suction filtration; washed with water (5×30 mL) and dried to give diethyl 2-(4-(4-bromo-3-chlorophenylamino)pyrido[3,4-a]pyrimidin-6-ylamino)-2-oxoethylphosphonate (233) (3.26 g, 95%); mp 121-124° C.; $^1$H NMR δ [(CD$_3$)$_2$SO]: 10.89 (s, 1H), 10.43 (s, 1H), 9.04 (s, 1H), 8.88 (s, 1H, 8.68 (s, 1 H, 8.24 (d, J=2.1 Hz, 1H), 7.82 (dd, J=8.8, 2.1 Hz, 1H), 7.78 (d, J=8.8 Hz, 1H), 4.17-4.00 (m, 4H), 3.32 (d, J=21.5, 2H), 1.26 (t, J=7.0 Hz, 6H). Anal. Calcd for C$_{19}$H$_{20}$BrClN$_5$O$_4$P.0.5H$_2$O; C, 42.44; H, 3.94; N, 13.02%. Found C, 42.42; H, 3.99; N, 12.98%.

To a stirred mixture of 2,2-diethoxy-N,N-dimethylethanamine (2.42 g, 15.0 mmol) and water (2.5 mL) at room temperature and under a nitrogen atmosphere was added an aq. 37% HCl (2.52 mL, 30.0 mmol). After addition the mixture was stirred at 40° C. (bath) for 48 h. It was cooled to 0° C. (bath). This is called solution A. KOH (4.30 g, 76.8 mmol) was dissolved in water (13 mL) at room temperature under a nitrogen atmosphere. It was cooled to 0° C. (bath). This is called solution B. To a stirred heterogeneous mixture of compound 233 (3.17 g, 6.00 mmol) and THF (13 mL) at room temperature and under a nitrogen atmosphere was added minimum amount of DMA (6.5 mL) to give a homogeneous solution. LiCl (254 mg, 6.00 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=20:1). After 40 min. it was poured into water (300 mL). Petroleum ether (300 mL) was added and stirred at room temperature for 30 min. Petroleum ether layer was decanted. More petroleum ether (300 mL) was added and stirred for 15 min. The solid was collected by suction filtration; washed with water (5×30 mL); dried under reduced pressure over silica geVKOH to give (2E)-N-[4-(4-bromo-3-chloroanilino)pyrido[3,4-d]pyrimidin-6-yl]-4-(dimethylamino)-2-butenamide (6) (2.71 g, 98%) as beige solid, mp 176-179; HPLC: 97.8% pure; $^1$H NMR δ [(CD$_3$)$_2$SO] 10.95 (s, 1H), 10.37 (s, 1H), 9.04 (s, 1H), 9.00 (s, 1H, 8.68 (s, 1 H), 8.27 (br s, 1 H), 7.84 (br d, J=8.3 Hz, 1H), 7.78 (d, J=8.8, 1H), 6.87 (dt, J=15.5, 6.0 Hz, 1H), 6.52 (br d, J=15.5 Hz, 1H), 3.09 (br d, J=5.4 Hz, 2H), 2.18 (s, 6H). Anal. Calcd for C$_{19}$H$_{18}$BrClN$_6$O.H$_2$O; C, 47.57; H, 4.20; N, 17.52. Found C, 47.95; H, 4.16; N, 17.31.

1.1.1.7 Preparation of (2E)-N-[4-(3,4-dibromoanilino)pyrido[3,4-d]pyrimidin-6-yl]-4-(dimethylamino)-2-butenamide (7) (Scheme 2)

A heterogeneous mixture of 6-fluoropyrido[3,4-d]pyrimidin-4(3H)-one (200) (1.65 g, 10.0 mmol), thionyl chloride (20 mL) and a catalytic amount of DMF (2 drops) was stirred under reflux for 5 h to give a homogeneous mixture. It was evaporated under reduced pressure at 50° C. (bath temperature) to give a light brown solid. To this solid was added a solution of 3,4-dibromoaniline (2.76 g, 11.0 mmol) in dry DMA (15 mL). The residue of 3,4-dibromoaniline was washed down with more DMA (2×2 mL). The reaction mixture was stirred at room temperature for 19 h. It was poured into water (300 mL). The pH was adjusted to ca. 8 using an aqueous solution of Na$_2$CO$_3$ at room temperature. Petroleum ether (300 mL) was added and stirred at room temperature for 30 min. The petroleum ether layer was decanted. It was repeated once more with petroleum ether. The solid was collected by filtration and washed successively with water (5×25 mL) and petroleum ether/ethyl acetate (10:1) (4×25 mL). It was dried in vacuum over silica gel/KOH overnight to give N-(3,4-dibromophenyl)-6-fluoropyrido[3,4-d]pyrimidin-4-amine (207) (3.50 g, 88%) as a beige solid, mp 262-264° C.; $^1$H NMR δ [(CD$_3$)$_2$SO] 10.14 (br s, 1H), 8.98 (s, 1H), 8.78 (s, 1H, 8.45 (br s, 1H), 8.26 (s, 1H), 7.91 (br d, J=7.8, 2.5 Hz, 1H), 7.80 (d, J=8.7 Hz, 1H). Anal. Calcd for C$_{13}$H$_7$Br$_2$FN$_4$; C, 39.23; H, 1.77; N, 14.08. Found C, 39.23; H, 1.79; N, 13.86.

A mixture of compound 207 (3.40 g, 8.54 mmol) and 4-methoxybenzylamine (11.2 mL, 85.4 mmol) in dry DMSO (22 mL) was stirred under a nitrogen atmosphere at 70° C. (bath temperature) for 138 h. The mixture was then cooled and poured into water (400 mL). Petroleum ether (400 mL) was added and stirred at room temperature for 30 min. The layers were allowed to separate and the petroleum ether layer was decanted. This procedure was repeated with more petroleum ether (400 mL). It was filtered and washed solid with water (3×30 mL). The sticky yellow/orange solid was stirred with acetone (100 mL) at room temperature for ca. 30 min. to give a fine orange precipitate. Water (200 mL) was added and stirred further at room temperature for 2 h. The solid was collected by suction-filtration, washed with water/acetone (2:1) (5×30 mL), and dried in vacuum over silica-gel/KOH to give pure N$^4$-(3,4-dibromophenyl)-N$^6$-(4-methoxybenzyl)pyrido[3,4-d]pyrimidine-4,6-diamine (216) (4.16 g, 95%) as a greenish yellow solid, mp 166-169° C.; $^1$H NMR δ [(CD$_3$)$_2$SO] 9.72 (s, 1H), 8.77 (s, 1H, 8.42 (s, 1H), 8.40 (br s, 1H), 7.89 (br d, J=7.7 Hz, 1H), 7.76 (d, J=8.7, Hz, 1H), 7.40-7.25 (m, 3H), 7.17 (s, 1H), 6.88 (br d, J=8.3 Hz, 2H), 4.49 (d, J=5.9 Hz, 2H), 3.71 (s, 3H). Anal. Calcd for C$_{21}$H$_{17}$Br$_2$N$_5$O.0.25hexane: C, 50.35; H, 3.85; N, 13.05%. Found C, 50.56; H, 3.54; N, 12.87%.

To a stirred heterogeneous mixture of compound 216 (4.08 g, 7.92 mmol) and DCM (80 mL) was added trifluoroacetic acid (6.07 mL, 79.2 mmol), followed by anisole (1.73 mL, 15.8 mmol), and the mixture was stirred further at room temperature for 46 h. It was poured into petroleum ether (500 mL) and stirred at room temperature for ca. 15 min. Petroleum ether layer was decanted and discarded. The process was repeated with more petroleum ether (400 mL). The solid left behind was dissolved in minimum MeOH (120 mL) and 5M NH$_3$ (150 mL) was added at 0° C. and stirred at room temperature for 15 min. The solid was collected and washed successively with water (5×20 mL), petroleum ether-ethyl acetate=5:1 (5×20 mL), and dried to give N$^4$-(3,4-dibromophenyl)pyrido[3,4-d]pyrimidine-4,6-diamine (225) (2.47 g, 79%), mp 265-268° C.; $^1$H NMR δ [(CD$_3$)$_2$SO] 9.80 (s, 1H), 8.72 (s, 1H), 8.44 (d, J=2.2 Hz, 1H), 8.42 (s, 1H), 7.90 (dd, J=8.8, 2.2 Hz, 1H), 7.74 (d, J=8.8 Hz, 1H), 7.14 (s, 1H), 6.30 (s, 2H). Anal. Calcd for C$_{13}$H$_9$Br$_2$N$_5$.0.1hexane: C, 40.47; H, 2.60; N, 17.35. Found C, 40.16; H, 2.45; N, 17.20.

To a stirred mixture of CDI (2.74 g, 16.9 mmol) and dry THF (13 mL), at room temperature and under a nitrogen atmosphere, was added a solution of 2-(diethoxyphosphoryl)acetic acid (2.96 g, 15.1 mmol) in THF (10 mL). After addition the reaction mixture was stirred further at 40° C. (bath) for 15 min (whence evolution of gases ceased). A solution of compound 225 (2.38 g, 6.02 mmol) in a mixed solvents of dry THF (7 mL) and DMA (8 mL) was added and stirred further at 40° C. The reaction was monitored by TLC (dichloromethane-MeOH=15:1). After stirred for 4 h, the reaction mixture was poured into water (250 mL) and stirred with petroleum ether (350 mL) at room temperature for 20 min. Petroleum ether layer was decanted. It was repeated once more with petroleum ether (200 mL). The solid was collected by suction filtration; washed with water (5×30 mL) and dried to give diethyl 2-(4-(3,4-dibromophenylamino)pyrido[3,4-d] pyrimidin-6-ylamino)-2-oxoethylphosphonate (234) (3.28 g, 95%); mp 120-124° C.; $^1$H NMR δ [(CD$_3$)$_2$SO]: 10.89 (s, 1H), 10.41 (s, 1H), 9.04 (s, 1H), 8.88 (s, 1H), 8.67 (s, 1 H), 8.34 (d, J=2.5 Hz, 1H), 7.87 (dd, J=8.8, 2.5 Hz, 1H), 7.77 (d, J=8.8 Hz, 1H), 4.17-4.03 (m, 4H), 3.32 (d, J=21.6 Hz, 2H), 1.26 (t, J=7.0 Hz, 6H). Anal. Calcd for C$_{19}$H$_{20}$Br$_2$N$_5$O$_4$P: C, 39.81; H, 3.52; N, 12.22%. Found C, 39.48; H, 3.78; N, 11.79%.

To a stirred mixture of 2,2-diethoxy-N,N-dimethylethanamine (2.25 g, 14.0 mmol) and water (2.4 mL) at room temperature and under a nitrogen atmosphere was added an aq. 37% HCl (2.35 mL, 28.0 mmol). After addition the mixture was stirred at 45° C. (bath) for 23 h. It was cooled to 0° C. (bath). This is called solution A. KOH (4.02 g, 71.7 mmol) was dissolved in water (12 mL) at room temperature under a nitrogen atmosphere. It was cooled to 0° C. (bath). This is called solution B. To a stirred heterogeneous mixture of compound 234 (3.21 g, 5.60 mmol) and THF (12 mL) at room temperature and under a nitrogen atmosphere was added minimum amount of DMA (6 mL) to give a homogeneous solution. LiCl (237 mg, 5.60 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC(DCM-MeOH=25:1). After 1 h it was poured into water (200 mL). Petroleum ether (200 mL) was added and stirred at room temperature for 30 min. Petroleum ether layer was decanted. More petroleum ether (200 mL) was added and stirred for 15 min. The solid was collected by suction filtration; washed with water (5×20 mL); dried under reduced pressure over silica gel/KOH to give (2E)-N-[4-(3,4-dibromoanilino)pyrido[3,4-d]pyrimidin-6-yl]-4-(dimethylamino)-2-butenamide (7) (2.76 g, 98%) as a beige solid, mp 176-179° C.; HPLC: 97.2% pure; $^1$H NMR δ [(CD$_3$)$_2$SO] 10.95 (s, 1H), 10.35 (s, 1H), 9.03 (s, 1H), 9.00 (s, 1H), 8.67 (br s, 1H), 8.37 (br s, 1H), 7.89 (br d, J=7.8 Hz, 1H), 7.77 (d, J=8.8, 1H), 6.87 (dt, J=15.4, 6.0 Hz, 1H), 6.52 (br d, J=15.4 Hz, 1H), 3.08 (br d, J=5.3 Hz, 2H), 2.19 (s, 6H). Anal. Calcd for C$_{19}$H$_8$Br$_2$N$_6$O.0.5H$_2$O: C, 44.30; H, 3.72; N, 16.31. Found C, 44.24; H, 3.81; N, 15.98.

1.1.1.8 Preparation of (2E)-4-(dimethylamino)-N-[4-(3-ethynyl-4-fluoroanilino)pyrido[3,4-d]pyrimidin-6-yl]-2-butenamide (8) (Scheme 2)

A heterogeneous mixture of 6-fluoropyrido[3,4-d]pyrimidin-4(3H)-one (200) (1.65 g, 10.0 mmol), thionyl chloride (20 mL) and a catalytic amount of DMF (2 drops) was stirred under reflux for 1 h to give a homogeneous mixture. It was evaporated under reduced pressure at 45° C. (bath temperature) to give a light brown solid. To this solid was added a solution of 3-ethynyl-4-fluoroaniline (*J. Org. Chem.*, 1981, 46, 2280-2286) (1.49 g, 11.0 mmol) and dry DMA (15 mL). The residue of 3-ethynyl-4-fluoroaniline was washed down with more DMA (2×2 mL). The reaction mixture was stirred at room temperature for 45 h. It was poured into water (300 mL). The pH was adjusted to ca. 9 using an aqueous solution of Na$_2$CO$_3$ at room temperature. Petroleum ether (300 mL) was added and stirred at room temperature for 30 min. The petroleum ether layer was decanted. It was repeated once more with petroleum ether (300 mL). The solid was collected by filtration and washed with water (5×50 mL); ethyl acetate/petroleum ether (1:10) (4×50 mL) and dried to give N-(3-ethynyl-4-fluorophenyl)-6-fluoropyrido[3,4-d]pyrimidin-4-amine (208) (2.39 g, 85%) as a pale brown solid, mp 223-226° C.; $^1$H NMR δ [(CD$_3$)$_2$SO] 10.10 (s, 1H), 8.96 (s, 1H), 8.73 (s, 1H), 8.24 (br s, 1H),), 8.12 (dd, J=6.4, 2.8 Hz, 1H), 7.96-7.88 (m, 1H), 7.39 (t, J=9.1 Hz, 1H), 4.54 (s, 1H). Anal. Calcd for C$_{15}$H$_8$F$_2$N$_4$.1.8H$_2$O: C, 57.25; H, 3.72; N, 17.80. Found C, 57.27; H, 3.49; N, 17.90.

A mixture of compound 208 (2.31 g, 8.19 mmol) and 4-methoxybenzylamine (10.7 mL, 81.9 mmol) in dry DMSO (20 mL) was stirred under a nitrogen atmosphere at 70° C. (bath temperature) for 118 h. The mixture was cooled and petroleum ether (300 mL) was added. It was stirred at room temperature for 15 min. The layers were allowed to separate and the petroleum ether layer was decanted. This procedure was repeated with more petroleum ether (300 mL). Water (300 mL) was added and the mixture was stirred at room temperature for 20 min. It was filtered and washed sticky solid with water (5×30 mL). The sticky solid was stirred with warm MeOH (70 mL) for 30 min. After cooled to room temperature, the solid was collected; washed with cold MeOH (3×10 mL) and dried in vacuum over silica-gel/KOH to give pure N$^4$-(3-ethynyl-4-fluorophenyl)-N$^6$-(4-methoxybenzyl)pyrido[3,4-d]pyrimidine-4,6-diamine (217) (0.92 g, 28%) as a yellow/orange solid, mp 197-199° C. The filtrate was evaporated to dry to give an orange/amber gum was which applied to a silica column [ethyl acetate/petroleum ether (2:1)] to afford more compound 217 (0.96 g, 29%). $^1$H NMR δ [(CD$_3$)$_2$SO] 9.66 (s, 1H), 8.74 (s, 1H), 8.36 (s, 1H), 8.08-8.02 (m, 1H), 7.93-7.85 (m, 1H), 7.39-7.13 (m, 5H), 6.88 (br d, J=8.7 Hz, 2H), 4.54-4.44 (m, 3H), 3.71 (s, 3H). Anal. Calcd for C$_{23}$H$_{18}$FN$_5$O.0.15MeOH: C, 68.79; H, 4.64; N, 17.33%. Found C, 69.09; H, 4.62; N, 16.97%.

To a stirred heterogeneous mixture of compound 217 (2.12 g, 5.32 mmol) and DCM (55 mL) was added trifluoroacetic acid (3.70 mL, 48.3 mmol), followed by anisole (1.17 mL, 10.6 mmol), and the mixture was stirred further at room temperature for 78 h. It was poured into petroleum ether (300 mL) and stirred at room temperature for ca. 20 min. Petroleum ether layer was decanted and discarded. The process was repeated with more petroleum ether (300 mL). The solid left behind was dissolved in acetone (25 mL) and 5M NH$_3$ (100 mL) added at 0° C. and stirred at room temperature for 40 min. The solid was collected and washed successively with acetone/water (1:5) (5×20 mL), petroleum ether/ethyl acetate=3:1 (5×20 mL), and dried to give N$^4$-(3-ethynyl-4-fluorophenyl)pyrido[3,4-d]-pyrimidine-4,6-diamine (226) (1.31 g, 89%), mp 218-222° C.; $^1$H NMR δ [(CD$_3$)$_2$SO] 9.72 (s, 1H), 8.70 (s, 1H), 8.36 (s, 1H), 8.10 (dd, J=6.4, 2.7 Hz, 1H), 7.96-7.87 (m, 1H), 7.33 (t, J=9.1 Hz, 1H), 7.13 (s, 1H), 6.26 (s, 2H), 4.50 (s, 1H). Anal. Calcd for C$_{15}$H$_{10}$FN$_3$.0.8H$_2$O.0.25-ethyl acetate: C, 60.87; H, 4.34; N, 22.18%. Found C, 60.67; H, 4.15; N, 22.11%.

To a stirred mixture of CDI (2.01 g, 12.4 mmol) and dry THF (9 mL), at room temperature and under a nitrogen atmosphere, was added a solution of 2-(diethoxyphosphoryl)acetic acid (2.18 g, 11.1 mmol) in THF (7 mL). After addition the reaction mixture was stirred further at 40° C. (bath) for 15 min (whence evolution of gases ceased). A mixture of compound 226 (1.24 g, 4.44 mmol) in a mixed solvents of dry THF (5 mL) and DMA (6 mL) was added and stirred further at 40° C. The reaction was monitored by TLC (dichloromethane-MeOH=30:1). After stirred for 22 h, it was poured into water (200 mL) and the residue washed down with MeOH. Petroleum ether (300 mL) was added and stirred at room temperature for 1 h. Petroleum ether layer was decanted. It was repeated once more with petroleum ether (150 mL). The solid was collected by suction filtration; washed with water (5×20 mL) and dried to give diethyl 2-(4-(3-ethynyl-4-fluorophenylamino)pyrido[3,4-d]-pyrimidin-6-ylamino)-2-oxoethylphosphonate (235) (1.85 g, 91%); mp 103-106° C.; $^1$H NMR δ [(CD$_3$)$_2$SO]: 10.84 (s, 1H), 10.33 (s, 1H), 9.01 (s, 1H), 8.86 (s, 1H), 8.61 (s, 1H), 8.01 (dd, J=6.4, 2.7 Hz, 1H), 7.92-7.83 (m, 1H), 7.35 (t, J=9.1 Hz, 1H), 4.51 (s, 1H), 4.17-4.03 (m, 4H), 3.32 (d, partially obscured by water peak, 2H), 1.26 (t, J=7.0 Hz, 6H). Anal. Calcd for C$_{21}$H$_{21}$FN$_3$O$_4$P.MeOH: C, 53.99; H, 5.15; N, 14.31%. Found C, 54.21; H, 4.94; N, 14.43%.

To a stirred mixture of 2,2-diethoxy-N,N-dimethylethanamine (1.56 g, 9.70 mmol) and water (1.6 mL) at room temperature and under a nitrogen atmosphere was added an aq. 37% HCl (1.62 mL, 19.3 mmol). After addition the mixture was stirred at 45° C. (bath) for 25 h. It was cooled to 0° C. (bath). This is called solution A. KOH (2.76 g, 49.3 mmol) was dissolved in water (8 mL) at room temperature under a nitrogen atmosphere. It was cooled to 0° C. (bath). This is called solution B. To a stirred heterogeneous mixture of compound 235 (1.76 g, 3.85 mmol) and THF (8 mL) at room temperature and under a nitrogen atmosphere was added minimum amount of DMA (4 mL) to give a homogeneous solution. LiCl (163 mg, 3.85 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=10:1). After stirred for 30 min. it was poured into water (300 mL). Petroleum ether (300 mL) was added and stirred at room temperature for 10 min. Petroleum ether layer was decanted. More petroleum ether (300 mL) was added and stirred for 10 min. The solid was collected by suction filtration; washed with water (4×20 mL); dried under reduced pressure over silica gel/KOH to give compound 8 (1.38 g, 92%) which was found only 89.7% pure by HPLC. Thus, the sample was stirred with MeOH (ca. 40 mL) for 30 min. The insoluble material was filtered off and to the filtrates was added one volume of water to precipitate out the required product. The solid was collected, washed with water/MeOH=3:1 (3×15 mL) and dried to give (2E)-4-(dimethylamino)-N-[4-(3-ethynyl-4-fluoroanilino)pyrido[3,4-d]pyrimidin-6-yl]-2-butenamide (8) (1.28 g, 85%) as a yellow/brown solid, mp 152-155° C.; $^1$H NMR δ [(CD$_3$)$_2$SO] 10.93 (s, 1H), 10.29 (s, 1H), 9.02 (s, 1H), 8.99 (s, 1H), 8.61 (s, 1H), 8.04 (dd, J=6.4, 2.7 Hz, 1H), 7.94-7.85 (m, 1H), 7.35 (t, J=9.1 Hz, 1H), 6.87 (dt, J=15.4, 6.0 Hz, 1H), 6.52 (br d, J=15.4 Hz, 1H), 4.53 (s, 1H), 3.09 (br d, J=6.0 Hz, 2H), 2.19 (s, 6H). Anal. Calcd for $C_{21}H_{19}FN_6O.0.8H_2O.0.7MeOH$: C, 61.00; H, 5.52; N, 19.67%. Found C, 61.26; H, 5.25; N, 19.47%.

1.1.1.9 Preparation of (2E)-N-[4-(4-chloro-3-ethynylanilino) pyrido[3,4-d]pyrimidin-6-yl]-4-(dimethylamino)-2-butenamide (9) (Scheme 2)

A heterogeneous mixture of 6-fluoropyrido[3,4-d]pyrimidin-4(3H)-one (200) (1.65 g, 10.0 mmol), thionyl chloride (20 mL) and a catalytic amount of DMF (2 drops) was stirred under reflux for 24 h to give a homogeneous mixture. It was evaporated under reduced pressure at 45° C. (bath temperature) to give a light brown solid. To this solid was added a solution of 3-ethynyl-4-chloroaniline (*J. Org. Chem.*, 1981, 46, 2280-2286) (1.67 g, 11.0 mmol) and dry DMA (15 mL). The residue of 3-ethynyl-4-chloroaniline was washed down with more DMA (2×2 mL). The reaction mixture was stirred at room temperature for 24 h. It was poured into water (300 mL) and the residue washed down with MeOH. The pH was adjusted to ca. 9 using an aqueous solution of Na$_2$CO$_3$ at room temperature. Petroleum ether (300 mL) was added and stirred at room temperature for 30 min. The petroleum ether layer was decanted. It was repeated once more with petroleum ether (300 mL). The solid was collected by filtration and washed with water (5×25 mL); ethyl acetate/petroleum ether (1:10) (4×25 mL) and dried to give N-(3-ethynyl-4-chlorophenyl)-6-fluoropyrido[3,4-d]pyrimidin-4-amine (209) (3.0 g, 100%) as a pale brown solid, mp 218-222° C.; $^1$H NMR δ [(CD$_3$)$_2$SO] 10.13 (s, 1H), 8.98 (s, 1H), 8.77 (s, 1H), 8.32-8.22 (m, 2H), 7.95 (dd, J=8.8, 2.6 Hz, 1H), 7.61 (d, J=8.8 Hz, 1H), 4.60 (s, 1H). Anal. Calcd for $C_{15}H_8ClFN_4.0.5H_2O.0.5MeOH$: C, 57.51; H, 3.43; N, 17.31. Found C, 57.33; H, 3.13; N, 17.10.

A mixture of compound 209 (3.07 g, 10.3 mmol) and 4-methoxybenzylamine (13.5 mL, 103 mmol) in dry DMSO (27 mL) was stirred under a nitrogen atmosphere at 70° C. (bath temperature) for 141 h. The mixture was cooled and petroleum ether (300 mL) was added. It was stirred at room temperature for 30 min. The layers were allowed to separate and the petroleum ether layer was decanted. This procedure was repeated with more petroleum ether (300 mL). Water (300 mL) was added and the mixture was stirred at room temperature for 30 min. It was filtered and washed sticky solid with water (4×20 mL). The sticky solid was dissolved in minimum acetone (50 mL) and water (200 mL) added. The mixture was stirred at room temperature overnight (22 h). Sticky solid generated again. Thus, the product was extracted into ethyl acetate, which after washed with water several times, was dried (MgSO) and evaporated. The crude product was applied to a silica column (dichloromethane/MeOH=50:1) to give $N^4$-(4-chloro-3-ethynylphenyl)-$N^6$-(4-methoxybenzyl)pyrido[3,4-d]pyrimidine-4,6-diamine (218) (2.30 g, 54%) as a greenish yellow solid, mp 201-203° C.; $^1$H NMR δ [(CD$_3$)$_2$SO] 9.72 (s, 1H), 8.76 (s, 1H), 8.40 (s, 1H), 8.19 (d, J=2.5 Hz, 1H), 7.96 (dd, J=8.9, 2.5 Hz, 14, 7.56 (d, J=8.9 Hz, 14, 7.39-7.28 (m, 3H), 7.17 (s, 1H), 6.93-6.82 (m, 2H), 4.59 (s, 1H), 4.49 (d, J=6.3 Hz, 2H), 3.71 (s, 34. Anal. Calcd for $C_{23}H_{18}ClN_5O.0.18hexane$: C, 67.04; H, 4.80; N, 16.23%. Found C, 66.76; H, 4.79; N, 15.96%.

To a stirred heterogeneous mixture of compound 218 (2.27 g, 5.46 mmol) and DCM (55 mL) was added trifluoroacetic acid (4.2 mL, 54.6 mmol), followed by anisole (1.2 mL, 10.9 mmol), and the mixture was stirred further at room temperature for 50 h. It was poured into petroleum ether (400 mL) and stirred at room temperature for ca. 30 min. Petroleum ether layer was decanted and discarded. The process was repeated with more petroleum ether (400 mL). The solid left behind was dissolved in acetone (30 mL) and 5M NH, (150 mL) added at 0° C. and stirred at room temperature for 20 min. The solid was collected and washed successively with acetone/water (1:5) (5×20 mL), petroleum ether/ethyl acetate=10:1 (5×20 mL), and dried to give $N^4$-(4-chloro-3-ethynylphenyl)pyrido[3,4-a]pyrimidine-4,6-diamine (227) (1.54 g, 95%), mp 210-213° C.; $^1$H NMR δ [(CD$_3$)$_2$SO] 9.77 (s, 1H), 8.71 (s, 1H), 8.40 (s, 1H), 8.24 (d, J=2.6 Hz, 1H), 7.97 (dd, J=8.8, 2.6 Hz, 1H), 7.55 (d, J=8.8 Hz, 1H), 7.14 (s, 1H), 629 (s, 2H), 4.56 (s, 1H). Anal. Calcd for $C_{15}H_{10}ClN_5.1.3H_2O.0.5$ acetone: C, 56.92; H, 4.52; N, 20.11%. Found C, 56.81; H, 4.22; N, 19.82%.

To a stirred mixture of CDI (2.14 g, 13.2 mmol) and dry THF (10 mL), at room temperature and under a nitrogen atmosphere, was added a solution of 2-(diethoxyphosphoryl) acetic acid (2.31 g, 11.8 mmol) in THF (8 mL). After addition the reaction mixture was stirred further at 40° C. (bath) for 15 min (whence evolution of gases ceased). A mixture of compound 227 (1.39 g, 4.70 mmol) in a mixed solvents of dry THF (6 mL) and DMA (7 mL) was added and stirred further at 40° C. The reaction was monitored by TLC (dichloromethane-MeOH=15:1). After stirred for 3 h, it was poured into water (300 mL) and the residue washed down with MeOH. Petroleum ether (300 mL) was added and stirred at room temperature for min. Petroleum ether layer was decanted. It was repeated once more with petroleum ether (200 mL). The solid was collected by suction filtration; washed with water (5×30 mL) and dried to give diethyl 2-(4-(4-chloro-3-ethynylphenylamino)pyrido[3,4-d]pyrimidin-6-ylamino)-2-oxoethylphosphonate (236) (2.03 g, 91%); mp 124-127° C.; $^1$H NMR δ [(CD$_3$)$_2$SO]: 10.86 (s, 1H), 10.37 (s, 1H), 9.03 (s, 1H), 8.87 (s, 1H), 8.65 (s, 1H), 8.14 (br s, 1H), 7.93 (br d, J=8.8 Hz, 1H), 7.35 (d, J=8.8 Hz, 1H), 4.58 (s, 1H), 4.20-4.00 (m, 4H), 3.30 (d, partially obscured by water peak, 2) -1), 1.26 (t, J=7.0 Hz, 6H). Anal. Calcd for $C_{21}H_{21}ClN_5O_4P.H_2O.0.2THF$: C, 51.72; H, 4.90; N, 13.83%. Found C, 52.06; H, 4.82; N, 13.70%.

To a stirred mixture of 2,2-diethoxy-N,N-dimethylethanamine (1.67 g, 10.4 mmol) and water (1.8 mL) at room temperature and under a nitrogen atmosphere was added an aq. 37% HCl (1.75 mL, 20.8 mmol). After addition the mixture was stirred at 45° C. (bath) for 27 h. It was cooled to 0° C. (bath). This is called solution A. KOH (2.98 g, 53.2 mmol) was dissolved in water (9 mL) at room temperature under a nitrogen atmosphere. It was cooled to 0° C. (bath). This is called solution B. To a stirred heterogeneous mixture of compound 236 (1.97 g, 4.16 mmol) and THF (9 mL) at room temperature and under a nitrogen atmosphere was added minimum amount of DMA (4.5 mL) to give a homogeneous solution. LiCl (176 mg, 4.16 mmol) was added and stirred at 0° C. (bath) for 15 min. The cold solution B was added and stirred at 0° C. for 2 min. Then the cold solution A was added and the final reaction mixture was continued to stir at 0° C. under a nitrogen atmosphere. The reaction was monitored by TLC (DCM-MeOH=10:1). After stirred for 35 min. it was poured into water (300 mL). Petroleum ether (300 mL) was added and stirred at room temperature for 15 min. Petroleum ether layer was decanted. More petroleum ether (300 mL) was added and stirred for 10 min. The solid was collected by suction filtration; washed with water (5×20 mL); petroleum ether/ethyl acetate=10:1×30 mL); dried under reduced pressure over silica gel/KOH to give compound 9 (1.61 g, 95%) which was found only 85.2% pure by HPLC. Thus, the sample was purified by a silica column (ethyl acetate/MeOH=10:1). The fractions containing the required product were combined and evaporated to give a yellow/orange solid. The solid was dissolved in warm ethyl acetate (30 mL) and precipitated with petroleum ether (90 mL). Solid was collected; washed with petroleum ether/ethyl acetate=3:1 (3×20 mL) and dried to give (2E)-N-[4-(4-chloro-3-ethynylanilino)pyrido[3,4-d]pyrimidin-6-yl]-4-(dimethylamino)-2-butenamide (9) (1.1 g, 65%) as a yellow/orange solid, mp 173-176° C.; $^1$H NMR δ [(CD$_3$)$_2$SO] 10.92 (s, 1H), 10.31 (s, 1H), 9.03 (s, 1H), 9.00 (s, 1H), 8.66 (s, 1H), 8.18 (d, J=2.2 Hz, 1H), 7.96 (dd, J=8.9, 2.2 Hz, 1H), 7.57 (d, J=8.9 Hz, 1H), 6.88 (dt, J=15.4, 6.0 Hz, 1H), 6.52 (br d, J=15.4 Hz, 1H), 4.58 (s, 1 H), 3.09 (br d, J=5.8 Hz, 2H), 2.19 (s, 6H). Anal. Calcd for $C_{21}H_{19}ClN_6O.0.8MeOH.0.1$-ethyl acetate: C, 60.42; H, 5.25; N, 19.04%. Found C, 60.15; H, 4.90; N, 18.76%.

1.1.2 The synthesis of α-methyl bromide triggers 1.1.2.1 Preparation of 5-(bromo methyl)-1-methyl-4-nitro-1H-imidazole (239) (Scheme 3)

Method 1

To a suspension of compound 237 (20.0 g, 157.36 mmol) (prepared according to the method of Chauviére et al, J. Med. Chem. 2003, 46, 427-440) and K$_2$CO$_3$ (32.62 g, 236.04 mmol) in DMF (200 mL) at 0° C. was added methyl iodide (14.70 mL, 236.04 mmol) dropwise. The resulting mixture was allowed to warm to room temperature and then stirred for 2 hours before the excess methyl iodide was evaporated at room temperature. The precipitate was removed by filtration and the DMF filtrate was concentrated under reduced pressure at 45-50° C. The residue obtained was extracted thoroughly with MeCN/DCMI (1:9) and the combined extracts were filtered through a short column of silica gel. After solvents were removed the crude was recrystallised from MeCN and toluene to give compound 238 as an off-white crystalline solid (15.74 g, 71%), m.p. 161-163° C. $^1$H NMR (CDCl$_3$) δ 7.33 (s, 1H), 3.65 (s, 3H), 2.63 (s, 3H). Identical to that previously reported (Hosmane et al, J. Org. Chem., 1985, 50(26), 5892-5).

A solution compound 238 (4.00 g, 28.34 mmol) and NBS (5.30 g, 29.78 mmol) in MIEN (200 mL) was irradiated at reflux for 2 hours with a 1000 W tungsten halide lamp. Approximately half of the solvent was removed in vacuo before water (100 mL) was added. Further concentration under reduced pressure afforded a white precipitate, which was collected by filtration, washed with water and dried under vacuum to give 5-(bromomethyl)-1-methyl-4-nitro-1H-imidazole (239) (4.69 g, 75%) as a white solid, m.p. 130-132° C. $^1$H NMR (CDCl$_3$, 400 MHz) δ 7.74 (s, 1H), 4.50 (s, 2H), 3.83 (s, 3H). Identical to that previously reported (Stribbling et al, PCI International patent publication WO 2008/039087). Analysis found: C, 27.81; H, 3.27; N, 19.05. $C_5H_6BrN_3O_2$.0.04 hexane requires: C, 28.16; H, 2.96; N, 18.80. HRMS (FAB+) found: 219.97220, 221.97018 (M+1), calcd. for $C_5H_7^{79/81}BrN_3O_2$: 219.97216, 221.97012.

Method 2

Compound 237 (120 g, 0.94 mol), K$_2$CO$_3$ (259.8 g, 1.88 mol), and acetonitrile (2 L) were charged to a 5-L 3-neck flask and the mixture was cooled to 0° C. with stirring at 200 rpm. Dimethyl sulphate (DMS) (97.8 mL, 1.03 mol) was slowly added by syringe pump over 2 hours. After 2 hours, the reaction was allowed to warm to room temperature and held overnight. The solids were filtered over celite (120 g) and the 5-L flask was washed with acetonitrile (200 mL). The solids were washed with acetonitrile (2×500 mL) until all product was removed. The solution was diluted with 75% brine (1 L) and the acetonitrile was removed by rotary evaporation. The resulting slurry was extracted with dichloromethane (4×1 L). The combined organic layers were filtered, before toluene (1 L) was added and the dichloromethane was removed by rotary evaporation. The resulting slurry was filtered and the cake washed with toluene (2×1 L). The wet solid was recovered as an off-white solid (121 g). The wet solid was recrystallized from water (1 L) and the solids washed with heptane (1 L). The solid was dried in a 40° C. vacuum oven overnight. Compound 238 was recovered as a white solid (86.6 g, 67%). $^1$H NMR identical to that described above.

A 20-L reactor was fitted with N$_2$, condenser, temperature probe, and air stirring. The reactor was charged with compound 238 (100 g, 0.71 mol), 1,3-dibromo-5,5-dimethylhydantoin (DBDMH) (203.0 g, 0.71 mol), 2,2'-azobisisobutyronitrile (AIBN) (45.97 g, 0.28 mol), and dichloromethane (6 L). The reaction was heated at reflux, stirring the homogenous solution at 150 rpm. After 100 hours, the reaction was held at 20° C. for 36 hours before quenching the reaction with 10% NaHCO$_3$ (1.5 L) and 10% Na$_2$S$_2$O$_5$ (1 L) to pH 7 and negative to KI-starch paper (Note: some gas evolution and a small exotherm [6° C.] was observed during the addition of Na$_2$S$_2$O$_5$). The organic layer was separated and filtered before water (1 L) was added and the dichloromethane was removed by rotary evaporation. The resulting slurry was filtered to give a light yellow solid which was re-suspended in toluene (500 mL) at 50° C. for 2.5 hours before cooling to room temperature. Filtration then gave a solid that was dried at 40° C. in a vacuum oven overnight, before being slurried in toluene (500 mL) at 100° C. for 1 hour. After cooling to room temperature the suspension was filtered to give a solid that was dried in a 40° C. vacuum oven overnight to give 5-(bromomethyl)-1-methyl-4-nitro-1H-imidazole (239) (63.3 g, 38%) as a light yellow solid. $^1$H NMR identical to that described above.

1.1.2.2 Preparation of 5-(bromomethyl)-1,2-dimethyl-4-nitro-1H-imidazole (244) (Scheme 4)

To a suspension of compound 240 (50.0 g, 393.39 mmol) and K$_2$CO$_3$ (81.55 g, 590.08 mmol) in DMF (300 mL) at 0° C. was added methyl iodide (36.74 mL, 590.08 mmol) dropwise. The resulting mixture was allowed to warm to room temperature and then stirred for 2 hours before the excess methyl iodide was evaporated at room temperature. The precipitate was removed by filtration and the DMF filtrate was concentrated under reduced pressure at 45-50° C. The residue obtained was extracted thoroughly with MeCN/DCM (1:9)

and filtered through a short column of silica gel. After solvents were removed the crude was recrystallised from MeCN (containing a small amount of MeOH) and toluene to give compound 241 (52.22 g, 94.0%) as a white crystalline solid. $^1$H NMR (CDCl$_3$) δ 7.66 (s, 1H), 3.67 (s, 34, 2.43 (s, 34. LR-MS (APCI+ve): m/e 142.5 (M+1). Identical to that previously reported (Rav-Acha and Cohen, J. Org. Chem. 1981, 46(23), 4717-4720).

A solution of compound 241 (33.0 g, 233.83 mmol) and t-butyl dichloroacetate (64.90 g, 350.74 mmol) (prepared from dichloroacetyl chloride, t-butanol and triethyl amine in DCM) in DMF (400 mL) was added dropwise to a suspension of potassium t-butoxide (91.83 g, 818.40 mmol) in DMF (400 mL) at −35 to −25° C. (dry-ice/MeCN bath). The resulting mixture was stirred at −25° C. for an additional 20 minutes before being poured into 0.5N HCl (approximately 1000 mL). A standard ethyl acetate/aqueous workup and column chromatography on silica gel eluting with ethyl acetate/hexane (3:2) then gave crude compound 242 as a dark solid (23.83 g, 35%), which was used without further purification. LR-MS (APCI+ve) m/e 290.5/292.5 (3:1, M+1).

Compound 242 as prepared above (23.83 g, 82.25 mmol) was treated with refluxing acetic acid (120 mL) for 45 minutes before being concentrated to dryness under reduced pressure. A standard NaHCO$_3$/DCM workup of the residue followed by column chromatography on silica gel eluting with ethyl acetate then gave compound 243 (10.00 g, 64%) as white solid. $^1$H NMR (CDCl$_3$) δ 5.03 (s, 2H), 3.67 (s, 3H), 2.46 (s, 3H). LR-MS (APCI+ve): m/e 190.4/192.4 (3:1, M+1).

A suspension of compound 243 (10.00 g, 52.74 mmol) and LiBr (4.80 g, 55.20 mmol) in ethyl acetate (500 mL) was heated at reflux for 4 hours before being subjected to a standard ethyl acetate/aqueous workup. The solid thus obtained was treated once again with LiBr/ethyl acetate as above. The crude product was then precipitated from DCM/i-Pr$_2$O by the addition of hexane, to give 5-(bromomethyl)-1,2-dimethyl-4-nitro-1H-imidazole (244) (11.46 g, 93%) as an off-white solid. $^1$H NMR (CDCl$_3$) δ 4.88 (s, 2H), 3.64 (s, 3H), 2.46 (s, 3H). Anal. Calcd for C$_5$H$_6$BrN$_3$O$_2$.0.04hexane: C, 28.16; H, 2.96; N, 18.80%. Found: C, 27.81; H, 3.27; N, 19.05%. LR-MS (APCI+ve): m/e 234.4/236.4 (1:1, M+1).

1.1.2.3 Preparation of 5-(bromomethyl)-2-ethyl-1-methyl-4-nitro-1H-imidazole (250) (Scheme 5)

To a suspension of compound 238 (12.65 g, 90.00 mmol) in chloroform (100 mL), was added bromine (5.53 mL, 108.00 mmol), slowly. The resulting mixture was then stirred for 2 hours before water (130 mL) was added. The chloroform was then removed by distillation and the resulting precipitate was collected by filtration, washed with water and dried under vacuum to give compound 245 (15.50 g, 79%) as a white solid, m.p. 180-181° C., identical to the reported value (Pyrnan and Timmis, J. Chem. Soc., Trans., 1923, 123, 494-503). NMR (CDCl$_3$) δ 3.63 (s, 3H), 2.69 (s, 3H). Anal. Calcd for C$_5$H$_6$BrN$_3$O$_2$: C, 27.29; H, 2.75; N, 19.10%. Found: C, 27.56; H, 2.83; N, 19.10%. LR-MS (APCI+ve): m/e 220.3/222.3 (1:1, M+1).

A solution of compound 245 (2.20 g, 10.0 mmol) and N-bromosuccinimide (NBS) (1.96 g, 11.0 mmol) in acetonitrile (100 mL) was radiated at reflux for 2 hours by a 1000 W tungsten halide lamp. Approximately half of the solvent was then removed by rotary evaporator before the same volume of water was added. Further evaporation afforded a white precipitate, which was collected by filtration, washed with water and dried under vacuum to give compound 246 (2.84 g, 95%) as white solid. $^1$H NMR (CDCl$_3$, 400 MHz) δ 4.88 (s, 2H), 3.74 (s, 3H). Analysis found: C, 20.36; H, 1.74; N, 13.98. C$_5$H$_5$Br$_2$N$_3$O$_2$ requires: C, 20.09; H, 1.69; N, 14.06. LR-MS (+): m/e 234.4/236.4 (1:1, M+1). 298.3/300.3/302.3 (1:2:1, M+1).

To a solution of compound 246 (2.80 g, 9.36 mmol) in DMF (30 mL) was added anhydrous sodium acetate (1.92 g, 23.4 mmol). The mixture was stirred for 2 hours at room temperature then given a standard aqueous ethyl acetate workup, to give compound 247 (2.54 g, 98%) as white solid, m.p. 110-112° C. $^1$H NMR (CDCl$_3$, 400 MHz) d 5.50 (s, 2H), 3.74 (s, 2.11 (s, 3H). Analysis found: C, 30.48; H, 2.82; N, 15.13. C$_7$H$_8$BrN$_3$O$_4$ requires: C, 30.24; H, 2.90; N, 15.11. LR-MS (+): m/e 278.4/280.4 (1:1, M+1).

A mixture of compound 247 (1.90 g, 6.83 mmol), tetraethyltin (5.42 mL, 27.34 mmol) and tetrakis(triphenylphosphine)palladium (790 mg, 0.68 mmol) in NMP (20 mL) was heated at 110-120° C. for 5 hours before undergoing a standard aqueous ethyl acetate workup. The crude product obtained was purified by flash column chromatography eluting with MeCN/DCM (1:5) before being precipitated from DCM by the addition of hexane, to give compound 248 (1.04 g, 67%) as a white solid, m.p. 71-73° C. $^1$H NMR (CDCl$_3$, 400 MHz) δ 5.48 (s, 2H), 3.64 (s, 3H), 2.76 (q, J=7.43 Hz, 2H), 2.10 (s, 3H), 1.37 (t, J=7.43 Hz, 3H). Analysis found: C, 48.11; H, 5.90; N, 18.23%. C$_9$H$_{13}$N$_3$O$_4$.0.04hexane requires: C, 48.11; H, 5.92; N, 18.22%. LR-MS (+): m/e 228.5 (M+1).

To the solution of compound 248 (1.25 g, 5.50 mmol) in MeOH (10 mL) was added d K$_2$CO$_3$ (1.52 g, 11.0 mmol). After stirring for 20 minutes the solvent was removed at reduced pressure and the residue was dissolved in DCM, filtered through a layer of silica gel and washed with ethyl acetate. The filtrate was concentrated to give white crystals, which were collected by filtration and washed with a mixture of ethyl acetate/hexane (1:1) to give compound 249 (949 mg, 93%) as white crystalline solid, m.p. 153-155° C. $^1$H NMR (CDCl$_3$, 400 MHz) δ 4.96 (d, J=6.80 Hz, 2H), 3.67 (s, 3H), 2.79 (t, J=6.80 Hz, 1H), 2.74 (q, J=7.50 Hz, 2H), 1.36 (t, J=7.50 Hz, 3H). Analysis found: C, 45.71; H, 6.07; N, 22.87%. C$_2$H$_{11}$N$_3$O$_3$ requires: C, 45.40; H, 5.99; N, 22.68%. LR-MS (+): m/e 186.5 (M+1).

To the solution of compound 249 (685 mg, 3.70 mmol) in DCM (30 mL) at 0° C. was added triethylamine (0.773 mL, 5.55 mmol), followed by MsCl (0.344 mL, 4.44 mmol) dropwise. After stirring for 45 minutes, the mixture was washed twice with saturated aqueous ammonium chloride and once with brine before being dried over anhydrous sodium sulphate and filtered through celite. Concentration of the filtrate in vacuo gave a white solid (971 mg) which was found by $^1$H NMR to be a mixture of mesylate and a-methyl chloride (3:1) and used directly in the next step. A solution of this solid (968 mg) in THF (50 mL) was treated LiBr (6.39 g, 86.85 mmol) at reflux for 0.5 hour. The solvent was then removed under reduced pressure and the resulting residue was distributed between water and ethyl acetate. The organic phase was washed with water twice and brine once before being dried over anhydrous sodium sulphate and filtered through celite). The solvent was removed in vacuo to give 5-(bromomethyl)-2-ethyl-1-methyl-4-nitro-1H-imidazole (250) (851 mg, 93%) as white solid, m.p. 91-93° C. $^1$H NMR (CDCl$_3$, 400 MHz) δ 4.88 (s, 2H), 3.65 (s, 3H), 2.76 (q, J=7.60 Hz, 2H), 1.37 (t, J=7.60 Hz, 3H). Analysis found: C, 34.41; H, 4.07; N, 16.96%. C$_7$H$_{10}$BrN$_3$O$_2$.0.04EtOAc requires: C, 34.18; H, 4.13; N, 16.70%. LR-MS (+): m/e 248.4/250.4 (1:1, M+1).

1.1.2.4 Preparation of 5-(bromomethyl)-1-methyl-4-nitro-1H-imidazole-2-carbonitrile (264) (Scheme 7)

Method 1

To a solution of compound 246 (1.40 g, 4.68 mmol) in DMA (14 mL) containing several drops of water, was added $K_2CO_3$ (647 mg, 4.68 mmol). The resulting solution was stirred over night before a standard ethyl acetate workup, followed by silica gel column chromatography eluting with MeCN/DCM (5:95-15:85), gave compound 262 (330 mg, 30%) as an off-white solid. $^1$H NMR ($^6$d-DMSO, 400 MHz) δ 5.56 (t, J=5.8 Hz, 1H), 4.86 (d, J=5.8 Hz, 2H), 3.70 (s, 3H). LR-MS (+): m/e 236.5/238.5 (1:1, M+1).

A mixture of compound 262 (300 mg, 1.27 mmol), $Zn(CN)_2$ (90 mg, 0.76 mmol), Zinc powder (10 mg, 0.15 mmol), $Pd_2(dba)_3$ (23 mg, 0.025 mmol) and dppf (28 mg, 0.051 mmol) in DMA (3 mL) was stirred under nitrogen at 120° C. for 3.5 hours. A standard aqueous $NH_4Cl$/ethyl acetate workup followed by silica gel column chromatography eluting with ethyl acetate/hexanes (1:1 to 2:1) then gave compound 263 (180 mg) as an off-white solid, which was found by $^1$H NMR to contain a small amount of unreacted starting material 262 and was used directly in the next step. $^1$H NMR ($CDCl_3$, 400 MHz) δ 5.09 (d, J=6.7 Hz, 2H), 4.00 (s, 3H), 2.49 (t, J=6.7 Hz, 1H).

To the solution of compound 263 (173 mg, ca. 0.93 mmol) in THF (10 mL) at 0° C. was added MsCl (0.088 mL, 1.14 mmol), followed by DIPEA (0.182 mL, 1.04 mmol) dropwise. After stirring for 1 hour, the reaction mixture was subjected to a standard aqueous $NH_4Cl$/ethyl acetate workup to give a yellow oil (237 mg; mixture of mesylate and a-methyl chloride by $^1$H NMR) that was used directly. To a solution of this oil (235 mg, ca. 0.90 mmol) in THF (10 mL) was added LiBr (1.57 g, 18.06 mmol). After 0.5 hr heating at reflux the solvent was removed in vacuo and the residue was subjected to a standard aqueous $NH_4Cl$/ethyl acetate workup. The crude product was further purified by silica gel column chromatography eluting with ethyl acetate/hexanes (1:4 to 1:2) to give 5-(bromomethyl)-1-methyl-4-nitro-1H-imidazole-2-carbonitrile (264) (65 mg, 21% over three steps) as a pink oil. $^1$H NMR ($CDCl_3$, 400 MHz) δ 4.86 (s, 2H), 3.95 (s, 3H). LR-MS (+): m/e 277.6/279.6 (1:1, M+1+MeOH).
Method 2

A mixture of compound 245 (1.10 g, 5.00 mmol), $Zn(CN)_2$ (352 mg, 3.00 mmol), zinc powder (39 mg, 0.60 mmol), $Pd_2(dba)_3$ (92 mg, 0.10 mmol) and dppf (111 mg, 0.20 mmol) in DMA (10 mL) was stirred under nitrogen at 120° C. for 3 hours, The reaction was then diluted with water and given a standard ethyl acetate workup, followed by silica gel column chromatography eluting with ethyl acetate/hexanes (3:4 then 1:1) to give compound 265 (657 mg, 79%) as an off-white solid, m.p. 99-101° C. $^1$H NMR ($CDCl_3$) δ 3.84 (s, 3H), 2.72 (s, 3H). Analysis found: C, 43.64; H, 3.58; N, 33.86. $C_6H_6N_4O_2$ requires: C, 43.38; H, 3.64; N, 33.72.

A mixture of compound 265 (166 mg, 1.00 mmol), 1,3-dibromo-5,5-dimethylhydantoin (DBDMH) (286 mg, 1.00 mmol), 2,2'-azobisisobutyronitrile (AIBN) (66 mg, 0.40 mmol) in dichloromethane (10 mL) was heated at reflux for 5 days before being concentrated at reduced pressure. The resulting residue was purified by silica gel column chromatography eluting with ethyl acetate/hexanes (1:2 then 1:1) to give 5-(bromomethyl)-1-methyl-4-nitro-1H-imidazole-2-carbonitrile (264) (137 mg, 56%) as colourless oil. $^1$H NMR ($CDCl_3$, 400 MHz) δ 4.86 (s, 2H), 3.95 (s, 3H). Analysis found; C, 30.17; H, 1.99; N, 22.25. $C_6H_5BrN_4O_2$.0.07EtOAc requires: C, 30.03; H, 2.23; N, 22.30. HRMS (ESI+, $^{79/81}$Br) found: m/z 266.9490/268.9475 (M+Na), calcd. for $C_6H_5^{79/81}BrN_4NaO_2^+$: 266.9488/268.9468.

1.1.2.5 Preparation of 5-(bromomethyl)-1-methyl-4-nitro-1H-imidazole-2-carboxamide (266) (Scheme 7)

A solution of 5-(bromomethyl)-1-methyl-4-nitro-1H-imidazole-2-carbonitrile (264) (70 mg, 0.29 mmol) in 90% $H_2SO_4$ (1 mL) was heated at 65-70° C. for 1 hour, before being diluted with water and given a standard ethyl acetate workup to give 5-(bromomethyl)-1-methyl-4-nitro-1H-imidazole-2-carboxamide (266) (67 mg, 84%), as white solid, m.p. 220-222° C. $^1$H NMR [$(CD_3)_2SO$] δ 8.18 (s, 1H), 7.87 (s, 1H), 5.05 (s, 2H), 4.02 (s, 3H). HR-MS (APC+, $^{79/81}$Br) found: m/z 262.9770/264.9752 (M+1), calcd. for $C_6H_8^{79/81}BrN_4O_3^+$: 262.9774/264.9754.

1.1.2.6 Preparation of 5-(bromomethyl)-1-methyl-4-nitro-2-(1-propynyl)-1H-imidazole (270) (Scheme 8)

A mixture of compound 247 (500 mg, 1.80 mmol), tributyl (1-propynyl)tin (1.64 mL, 5.39 mmol) and tetrakis(triphenylphosphine)palladium (416 mg, 0.36 mmol) in NMP (15 mL) was heated at 80° C. overnight (14 hours) before undergoing a standard aqueous-ethyl acetate workup. The crude product obtained was further purified by flash column chromatography eluting with MeCN/DCM (gradient from 1:20 to 1:5) to give compound 267 (147 mg, 34%) as white solid, $^1$H NMR ($CDCl_3$, 400 MHz) δ 5.47 (s, 2H), 3.77 (s, 34, 2.14 (s, 34, 2.10 (s, 3H). LR-MS (+): m/e 238.5 (M+1); followed by compound 268 (105 mg, 30%) also as white solid, $^1$H NMR ($CDCl_3$, 400 MHz) δ 4.96 (d, J=7.0 Hz, 24, 3.79 (s, 3H), 2.60 (t, J=7.0 Hz, 14, 2.14 (s, 3H). LR-MS (+): m/e 196.5 (M+1). Compound 268 was obtained quantitatively by treating compound 267 with $K_2CO_3$ in MeOH.

To a solution of compound 268 (110 mg, 0.56 mmol) in DCM (10 mL) at 0° C. was added triethylamine (0.118 mL, 0.84 mmol) followed by MsCl (0.052 mL, 0.68 mmol) dropwise. After 30 minutes at 0° C. and 30 minutes at room temperature, the mixture was washed twice with saturated aqueous ammonium chloride and brine, before being dried over anhydrous sodium sulphate and filtered through celite. Concentration under reduced pressure gave compound(s) 269 (145 mg, ~94%) as an off-white solid, which was found by $^1$H NMR to be a mixture of mesylate and chloride (3.6:1) and was used without further purification. $^1$H NMR ($CDCl_3$, 400 MHz) for the mesylate: δ 5.62 (s, 2H), 3.81 (s, 3H, 3.13 (s, 3H), 2.15 (s, 3H); for the chloride: δ 5.02 (s, 2H), 3.79 (s, 3H), 2.14 (s, LR-MS (+): 274.5 (M+1 of the mesylate); 214.4/216.4 (3:1, M+1 of the chloride).

Mixture 269 (145 mg, ~0.53 mmol) was treated with LiBr (922 mg, 10.61 mmol) in refluxing THF (10 mL) for 30 minutes. The THF was then removed in vacuo and the resulting residue was distributed between water and ethyl acetate. The organic phase was washed with water and brine, dried over anhydrous sodium sulphate and filtered through celite, before being concentrated in vacuo. The crude product thus obtained was purified by flash column chromatography eluting with ethyl acetate/hexane (1:1) to give 5-(bromomethyl)-1-methyl-4-nitro-2-(1-propynyl)-1H-imidazole (270) (95 mg, 69%) as white solid. $^1$H NMR ($CDCl_3$, 400 MHz) δ 4.86 (s, 2H), 3.76 (s, 3H), 2.14 (s, 3H). LR-MS (+): m/e 258.5/260.5 (1:1, M+1).

1.1.3 The synthesis of Quaternary Ammonium Salt Prodrugs

Method A: Preparation of Quaternary Ammonium Salt Prodrugs in N-methyl-2-pyrrolidinone (NMP) Followed by Acetonitrile Precipitation To a solution of the dimethylamine-bearing kinase inhibitor of Formula I in NMP at room temperature was added the α-methyl bromide trigger (1.0-1.2 eq.). The resulting mixture was stirred overnight (~15 hours). Acetonitrile was then added to the reaction mixture dropwise with continued stirring until a precipitate started to form. The resulting mixture was then stirred for a further 2 hours before the precipitate was collected by filtration or by centrifugation, washed with acetonitrile, ethyl acetate and hexane. Drying under vacuum then gave the quaternary ammonium salt prodrug as a white or off-white solid. If neccessary, the product was further purified by recrystallisation from NMP and MeCN.

1.1.3.1 Preparation of (2E)-4-[(4-{3-chloro-4-[(3-chlorobenzyl)oxy]anilino}pyrido[3,4-d]pyrimidin-6-yl)amino]-N,N-dimethyl-N-[(1-methyl-4-nitro-1H-imidazol-5-yl)methyl]-4-oxo-2-buten-1-ammonium bromide (12) (Scheme 10)

Reaction of compound 1 (500 mg, 0.96 mmol) in NMP (1.2 mL) with α-methyl bromide 239 (231 mg, 1.05 mmol) according to Method A gave (2E)-4-[(4-{3-chloro-4-[(3-chlorobenzyl) oxy]anilino}pyrido[3,4-d]pyrimidin-6-yl)amino]N,N-dimethyl-N-[(1-methyl-4-nitro-1H-imidazol-5-yl)methyl]-4-oxo-2-buten-1-ammonium bromide (12) (517 mg, 73%), m.p. 182-186° C. (dec). $^1$H NMR [(CD$_3$)$_2$SO] δ 11.28 (s, 1H), 10.25 (s, 1 H), 9.04 (s, 1 H), 8.98 (s, 1 H), 8.61 (s, 1 H), 8.14 (s, 1 H), 7.98 (d, J=2.5 Hz, 1 H), 7.74-7.72 (dd, J=8.9, 2.5 Hz, 1 H), 7.56 (s, 1H), 7.47-7.40 (m, 3 H), 7.28 (d, J=9.1 Hz, 1 H), 7.06-6.98 (m, 1H), 6.80 (d, J=15.2 Hz, 1 H), 5.26 (s, 2H), 5.05 (br, 2 H), 4.44 (d, J=7.1 Hz, 2 H), 3.88 (s, 3 H), 3.13 (s, 6 H). Analysis found: C, 48.93; H, 3.92; N, 16.27. $C_{31}H_{30}BrCl_2N_9O_4.H_2O.0.1EtOAc$ requires: C, 48.96; H, 4.29; N, 16.37.

1.1.3.2 Preparation of (2E)-4-[(4-{[1-(3-fluorobenzyl)-1H-indazol-5-yl]amino}pyrido[3,4-a]pyrimidin-6-yl)amino]-N,N-dimethyl-N-[(1-methyl-4-nitro-1H-imidazol-5-yl)methyl]-4-oxo-2-buten-1-ammonium bromide (13) (Scheme 10)

Reaction of compound 2 (500 mg, 1.01 mmol) in NMP (1.8 mL) with a-methyl bromide 239 (244 mg, 1.11 mmol) according to Method A gave (2E)-4-[(4-{[1-(3-fluorobenzyl)-1H-indazol-5-yl]amino}pyrido[3,4-d]pyrimidin-6-yl)amino]N,N-dimethyl-N-[(1-methyl-4-nitro-1H-imidazol-5-yl)methyl]-4-oxo-2-buten-1-ammonium bromide (13) (538 mg, 74%), m.p. 183-187° C. (dec). $^1$H NMR [(CD$_3$)$_2$SO] δ 11.27 (s, 1H), 10.35 (s, 1 H), 9.02 (s, 2 H), 8.56 (s, 1 H), 8.17-8.14 (m, 3 H), 7.75-7.69 (m, 2H), 7.40-7.35 (m, 1H), 7.12-6.99 (m, 4H), 6.80 (d, J=15.2 Hz, 1 H), 5.71 (s, 2H), 5.05 (br, 2 H), 4.44 (d, J=7.0 Hz, 2 H), 3.87 (s, 3 H), 3.13 (s, 6 H). Analysis found: C, 51.71; H, 4.53; N, 20.33. $C_{32}H_{31}BrFN_{11}O_3.1.5H_2O.0.1EtOAc$ requires: C, 51.72; H, 4.66; N, 20.48.

1.1.3.3 Preparation of (2E)-N-[(1,2-dimethyl-4-nitro-1H-imidazol-5-yl)methyl]-4-[(4-{[1-(3-fluorobenzyl)-1H-indazol-5-yl]amino}pyrido[3,4-d]-pyrimidin-6-yl)amino]-N,N-dimethyl-4-oxo-2-buten-1-ammonium bromide (14) (Scheme 11)

Reaction of compound 2 (100 mg, 0.20 mmol) in NMP (0.5 mL) with a-methyl bromide 244 (52 mg, 0.22 mmol) according to Method A gave (2E)-N-[(1,2-dimethyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (14) (93 mg, 63%), m.p. 188-192° C. (dec). $^1$H NMR [(CD$_3$)$_2$SO] δ 11.27 (s, 1H), 10.38 (s, 1 H), 9.03 (s, 2 H), 8.56 (s, 1 H), 8.17 (s, 2H), 7.76-7.68 (m, 2H), 7.40-7.35 (m, 1H), 7.12-6.99 (m, 4H), 6.80 (d, J=15.2 Hz, 1 H), 5.71 (s, 2H), 5.05 (br, 2 H), 4.43 (d, J=6.8 Hz, 2 H), 3.75 (s, 3 H), 3.11 (s, 6 H), 2.44 (s, 3H). Analysis found: C, 50.81; H, 4.76; N, 19.42. $C_{33}H_{33}BrFN_{11}O_3.2.9H_2O$ requires: C, 50.63; H, 5.00; N, 19.64.

1.1.3.4 Preparation of (2E)-4-({4-[3-chloro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (15) (Scheme 10)

Reaction of compound 3 (500 mg, 1.02 mmol) in NMP (1 mL) with a-methyl bromide 239 (225 mg, 1.02 mmol) according to Method A gave (2E)-4-({4-[3-chloro-4-(2-pyridinylmethoxy)anilino]pyrido[3,4-d]-pyrimidin-6-yl}amino)-N,N-dimethyl-N-[(1-methyl-4-nitro-1H-imidazol-5-yl)methyl]-4-oxo-2-buten-1-ammonium bromide (15) (610 mg, 84%), m.p. 189-191° C. (dec). $^1$H NMR [(CD$_3$)$_2$SO] δ 11.28 (s, 1H), 10.25 (s, 1 H), 9.04 (s, 2 H), 8.98 (s, 1 H), 8.61-8.60 (m, 2H), 8.14 (s, 1H), 7.99 (d, J=2.5 Hz, 1H), 7.91-7.87 (dt, J=1.6, 7.7 Hz, 1H), 7.74-7.71 (dd, J=2.5, 8.94 Hz, 1H), 7.59 (d, J=7.8 Hz, 1H), 7.39-7.36 (dd, J=5.3, 7.0 Hz, 1H), 7.29 (d, J=9.0 Hz, 1H), 7.06-6.98 (m, 1H), 6.80 (d, J=15.2 Hz, 1 H), 5.31 (s, 2H), 5.05 (br, 2 H), 4.44 (d, J=7.1 Hz, 2 H), 3.88 (s, 3 H), 3.11 (s, 6 H). Analysis found: C, 48.65; H, 4.34; N, 18.58. $C_{30}H_{30}BrClN_{10}O_4.1.8H_2O$ requires: C, 48.54; H, 4.56:, N, 18.87.

1.1.3.5 Preparation of (2E)-4-{[4-(3,4-dichloroanilino)pyrido[3,4-d]pyrimidin-6-yl]amino}N,N-dimethyl-N-[(1-methyl-4-nitro-1H-imidazol-5-yl)methyl]-4-oxo-2-buten-1-ammonium bromide (16) (Scheme 10)

Reaction of compound 4 (500 mg, 1.20 mmol) in NMP (1.2 mL) with α-methyl bromide 239 (290 mg, 1.32 mmol) according to Method A gave (2E)-4-{[4-(3,4-dichloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (16) (648 mg, 85%), m.p. 191-195° C. (dec). $^1$H NMR [(CD$_3$)$_2$SO] δ 11.32 (s, 1H), 10.41 (s, 1 H), 9.09 (s, 1 H), 9.02 (s, 1 H), 8.71 (s, 1 H), 8.27 (d, J=2.4 Hz, 1 H), 8.14 (s, 1H), 7.93-7.90 (dd, J=8.8, 2.4 Hz, 1 H), 7.67 (d, J=8.8 Hz, 1 H), 7.07-6.99 (m, 1 H), 6.80 (d, J=15.2 Hz, 1 H), 5.06 (br, 2 H), 4.45 (d, J=7.2 Hz, 2 H), 3.88 (s, 3 H), 3.13 (s, 6 H). Analysis found: C, 43.86; H, 3.82; N, 18.79. $C_{24}H_{24}BrCl_2N_9O_3.H_2O.0.1EtOAc$ requires: C, 44.13; H, 4.07; N, 18.98.

1.1.3.6 Preparation of (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (17) (Scheme 10)

Reaction of compound 5 (500 mg, 1.08 mmol) in NMP (1.2 mL) with α-methyl bromide 239 (262 mg, 1.19 mmol) according to Method A gave (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (17) (650 mg, 88%), m.p. 200-204° C. (dec). $^1$H NMR [(CD$_3$)$_2$SO] δ 11.32 (s, 1H), 10.40 (s, 1 H), 9.08 (s, 1 H), 9.02 (s, 1 H), 8.70 (s, 1 H), 8.37 (d, J=2.5 Hz, 1 H), 8.14 (s, 1H), 7.98-7.95 (dd, J=8.8, 2.5 Hz, 1 H), 7.66 (d, =8.8 Hz, 1 H), 7.06-6.99 (m, 1 H), 6.80 (d, J=15.3 Hz, 1 H), 5.05 (br, 2 H), 4.44 (d, J=7.2 Hz, 2 H), 3.88 (s, 3 H), 3.13 (s, 6 H). Analysis found: C, 41.16; H, 3.67; N, 17.55. $C_{24}H_{24}Br_2ClN_9O_3.H_2O.0.1EtOAc$ requires: C, 41.36; H, 3.81; N, 17.79.

1.1.3.7 Preparation of (2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (18) (Scheme 10).

Reaction of compound 6 (700 mg, 1.52 mmol) in NMP (1.5 mL) with α-methyl bromide 239 (367 mg, 1.67 mmol) according to Method A gave (2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (18) (875 mg, 85%), m.p. 209-213° C. (dec). $^1$H NMR [(CD$_3$)$_2$SO] δ 11.35 (s, 1H), 10.43 (s, 1 H), 9.09 (s, 1 H), 9.03 (s, 1 H), 8.71 (s, 1 H), 8.27 (d, J=2.1 Hz, 1 H), 8.15 (s, 1H), 7.86-7.78 (m, 2 H), 7.07-6.99 (m, 1 H), 6.80 (d, J=15.3 Hz, 1 H), 5.05 (br, 2 H), 4.44 (d, 6.8 Hz, 2 H), 3.87 (s, 3 H), 3.12 (s, 6 H). Analysis found: C, 40.97; H, 3.68; N, 18.03. C$_{24}$H$_{24}$Br$_2$ClN$_9$O$_3$.1.2H$_2$O requires: C, 40.98; H, 3.78; N, 17.92.

1.1.3.8 Preparation of (2E)-4-{[4-(3,4-dibromoanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (19) (Scheme 10)

Reaction of compound 7 (700 mg, 1.38 mmol) in NMP (1.5 mL) with α-methyl bromide 239 (335 mg, 1.52 mmol) according to Method A gave (2E)-4-{[4-(3,4-dibromoanilino)pyrido[3,4-a]pyrimidin-6-yl]amino}-N,N-dimethyl-N-[(1-methyl-4-nitro-1H-imidazol-5-yl)methyl]-4-oxo-2-buten-1-ammonium bromide (19) (840 mg, 84%), m.p. 215-219° C. (dec). $^1$H NMR [(CD$_3$)$_2$SO] δ 11.35 (s, 1H), 10.41 (s, 1 H), 9.09 (s, 1 H), 9.02 (s, 1 H), 8.71 (s, 1H), 8.37 (d, J=2.1 Hz, 1 H), 8.14 (s, 1H), 7.91-7.88 (dd, =8.8, 2.2 Hz, 1 H), 7.79 (d, J=8.8 Hz, 1 H), 7.07-7.01 (m, 1 H), 6.80 (d, =15.2 Hz, 1 H), 5.04 (br, 2 H), 4.44 (d, J=7.1 Hz, 2 H), 3.87 (s, 3 H), 3.12 (s, 6 H). Analysis found: C, 38.79; H, 3.34; N, 16.70. C$_{24}$H$_{24}$Br$_3$N$_9$O$_3$.H$_2$O requires: C, 38.73; H, 3.52; N, 16.94.

1.1.3.9 Preparation of (2E)-4-{[4-(3-ethynyl-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (20) (Scheme 10)

Reaction of compound 8 (586 mg, 1.50 mmol) in NMP (1 mL) with a-methyl bromide 239 (363 mg, 1.65 mmol) according to Method A gave (2E)-4-{[4-(3-ethynyl-4-fluoroanilino)pyrido[3,4-a]pyrimidin-6-yl]amino}-N,N-dimethyl-N-[(1-methyl-4-nitro-1H-imidazol-5-yl)methyl]-4-oxo-2-buten-1-ammonium bromide (20) (645 mg, 70%), m.p. 198° C. (dec). $^1$H NMR [(CD$_3$)$_2$SO] δ 11.31 (s, 1H), 10.36 (s, 1 H), 9.06 (s, 1 H), 9.00 (s, 1 H), 8.65 (s, 1H), 8.14 (s, 1H), 8.03 (br, 1H), 7.88 (br, 1H), 7.36 (t, J=9.1 Hz, 1 H), 7.06-6.99 (m, 1 H), 6.80 (d, J=15.2 Hz, 1 H), 5.06 (br, 2 H), 4.53 (s, 1H), 4.45 (d, J=7.0 Hz, 2 H), 3.88 (s, 3 H), 3.13 (s, 6 H). Analysis found: C, 48.61; H, 4.37; N, 18.78. C$_{24}$H$_{24}$Br$_3$N$_9$O$_3$.2H$_2$O.0.2EtOAc requires: C, 48.47; H, 4.64; N, 18.98.

1.1.3.10 Preparation of (2E)-4-{[4-(4-chloro-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (21) (Scheme 10)

Reaction of compound 9 (500 mg, 1.23 mmol) in NMP (1.2 mL) with α-methyl bromide 239 (297 mg, 1.35 mmol) according to Method A gave (2E)-4-{[4-(4-chloro-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (21) (630 mg, 82%), m.p. 199-202° C. (dec). $^1$H NMR [(CD$_3$)$_2$SO] δ 11.34 (s, 1H), 10.39 (s, 1 H), 9.08 (s, 1 H), 9.02 (s, 1 H), 8.69 (s, 1 H), 8.17 (d, J=2.5 Hz, 1 H), 8.14 (s, 1H), 7.96-7.93 (dd, J=8.9, 2.5 Hz, 1 H), 7.59 (d, J=8.9 Hz, 1 H), 7.06-6.99 (m, 1 H), 6.80 (d, J=15.2 Hz, 1 H), 5.05 (br, 2 H), 4.60 (s, 1H), 4.44 (d, =7.0 Hz, 2 H), 3.87 (s, 3 H), 3.12 (s, 6 H). Analysis found: C, 48.16; H, 4.22; N, 19.19. C$_{26}$H$_{25}$BrClN$_9$O$_3$.1.2H$_2$O.0.1EtOAc requires: C, 48.24; H, 4.32; N, 19.18.

2. Efficacy of the Compounds

2.1 Cell Growth Inhibitory Activity

2.1.1. Pan-erbB Kinase Inhibitors

Kinase inhibitors of Formula I (compounds 1-9) were tested for their ability to inhibit the proliferation of three human carcinoma cell lines, selected to provide a comparison with literature precedent: A431 (epidermoid), which overexpresses erbB1 (EGFR); H1975 (non-small-cell lung), which overexpresses erbB1 L858R/T790M a double mutant form of erbB1 that is known to confer resistance to the approved reversible erbB1 inhibitor erlotinib and SKOV3 (ovarian), which over express erbB2 (HER2). The cells were exposed to test compounds for either 24 hours under oxic conditions or for 4 hours under anoxia followed by 20 hours under oxic conditions. They were then washed free of drug and incubated for a further 4 days, before being stained for cellular growth with sulforhodamine B. The concentration of compound required to inhibit cellular growth by 50% relative to untreated control wells, termed the IC50 value, was calculated.

Results are summarised in Table 1.

TABLE 1

Inhibition of cellular proliferation in A431, H1975 and SKOV3 cells

Cellular Growth Inhibition IC$_{50}$ (μM)[a]

| Compound Number | A431 | | | H1975 | | | SKOV3 | | |
|---|---|---|---|---|---|---|---|---|---|
| | Oxic[b] | Anoxic[c] | HCR[d] | Oxic[b] | Anoxic[c] | HCR[d] | Oxic[b] | Anoxic[c] | HCR[d] |
| 1 | 0.28 | 0.221 | 1.2 | 1.2 | 0.88 | 2.5 | 1.8 | 0.69 | 1.8 |
| 2 | 0.13 | 0.09 | 1.0 | 0.9 | 1.0 | 1.4 | 0.78 | 0.9 | 3.3 |
| 3 | 0.12 | 0.14 | 1.4 | 0.51 | 0.73 | 0.8 | 0.71 | 1.13 | 1.7 |

TABLE 1-continued

Inhibition of cellular proliferation in A431, H1975 and SKOV3 cells

| Compound | Cellular Growth Inhibition IC$_{50}$ (μM)$^a$ | | | | | | | | |
|---|---|---|---|---|---|---|---|---|---|
| | A431 | | | H1975 | | | SKOV3 | | |
| Number | Oxic$^b$ | Anoxic$^c$ | HCR$^d$ | Oxic$^b$ | Anoxic$^c$ | HCR$^d$ | Oxic$^b$ | Anoxic$^c$ | HCR$^d$ |
| 4 | 0.009 | 0.015 | 0.9 | 0.42 | 0.56 | 1.1 | 0.36 | 0.55 | 0.9 |
| 5 | 0.009 | 0.010 | 1.0 | 0.29 | 0.50 | 0.9 | 0.30 | 0.45 | 0.9 |
| 6 | 0.005 | 0.005 | 2.0 | 0.15 | 0.22 | 0.7 | 0.20 | 0.55 | 0.7 |
| 7 | 0.005 | 0.008 | 0.8 | 0.18 | 0.27 | 1.0 | 0.37 | 0.60 | 1.2 |
| 8 | 0.07 | 0.12 | 1.8 | 1.3 | 1.4 | 1.4 | 1.8 | 1.8 | 1.7 |
| 9 | 0.02 | 0.016 | 2.2 | 0.40 | 0.56 | 0.5 | 0.50 | 0.96 | 1.7 |

Footnotes for Table 1
$^a$compound dose-response curves were determined at 10 concentrations. Cells received a 24 hour exposure to test compounds before being washed (x3) with drug-free media. The IC50 (umol/L) values are the concentrations required to inhibit cell growth by 50% relative to untreated controls. Values are the average of 2-8 independent determinations (% CV < 20 in all cases).
$^b$Experiment performed entirely under oxic conditions.
$^c$The initial 4 hours of the 24 hour drug exposure was performed under anoxic conditions.
$^d$Hypoxic Cytotoxicity Ratio = fold change in intra-experimental IC50 for cells receiving 4 hours of anoxia relative to cells that received only oxic conditions.

Irreversible erbB1, 2, 4 inhibitors 1, 2, 3, 4, 5, 6, 7, 8 and 9 more potently inhibited proliferation of aerobic A431 cells (IC50s=0.28 to 0.005 umol/L) than H1975 (IC50s=1.3 to 0.15 umol/L) and SKOV3 (IC50s=1.8 to 0.2 umol/L) cells and did not show any significant change in potency when the cells received 4 hours of anoxia with intraexperimental HCR ranging from 0.5 to 3.3 for all compounds across the three cell lines.

2.1.2 Prodrugs of pan-erbB Inhibitors

Selected prodrug compounds of Formula III (compounds 12-21) were tested for their ability to inhibit the proliferation of three human carcinoma cell lines, selected to provide a comparison with literature precedent: A431 (epidermoid), which overexpresses erbB1 (EGFR); H1975 (non-small-cell lung), which overexpresses erbB1 L858R/T790M a double mutant form of erbB1 that is known to confer resistance to the approved reversible erbB1 inhibitor erlotinib and SKOV3 (ovarian), which over express erbB2 (HER2). The cells were exposed to test compounds for either 24 hours under oxic conditions or for 4 hours under anoxia followed by 20 hours under oxic conditions. They were then washed free of drug and incubated for a further 4 days, before being stained for cellular growth with sulforhodamine B. The concentration of compound required to inhibit cellular growth by 50% relative to untreated control wells, termed the IC50 value, was calculated.

Results are summarised in Table 2.

TABLE 2

Inhibition of cellular proliferation in A431, H1975 and SKOV3 cells

| Compound | Cellular Growth Inhibition IC$_{50}$ (μM)$^a$ | | | | | | | | |
|---|---|---|---|---|---|---|---|---|---|
| | A431 | | | H1975 | | | SKOV3 | | |
| Number | Oxic$^b$ | Anoxic$^c$ | HCR$^d$ | Oxic$^b$ | Anoxic$^c$ | HCR$^d$ | Oxic$^b$ | Anoxic$^c$ | HCR$^d$ |
| 12 | 2.9 | 0.37 | 34 | 36 | 2.4 | 14 | 47 | 8.1 | 26 |
| 13 | 6.2 | 0.24 | 52 | 92 | 3.3 | 42 | 315 | 1.6 | 528 |
| 14 | 5.7 | 0.063 | 96 | 20 | 1.2 | 26 | 32 | 1.10 | 42 |
| 15 | 10 | 0.30 | 47 | 26 | 0.43 | 69 | 159 | 0.60 | 295 |
| 16 | 0.33 | 0.015 | 24 | 32 | 0.40 | 89 | 40 | 0.53 | 170 |
| 17 | 0.15 | 0.019 | 8 | 11 | 0.48 | 22 | 19 | 1.1 | 38 |
| 18 | 0.50 | 0.012 | 50 | 13.3 | 0.20 | 66 | 13 | 0.60 | 24 |
| 19 | 0.42 | 0.025 | 23 | 15 | 0.23 | 75 | 29 | 0.42 | 91 |
| 20 | 3.9 | 0.13 | 56 | 118 | 3.3 | 41 | 194 | 4.4 | 15 |
| 21 | 0.85 | <0.01 | >85 | 18 | 0.60 | 18 | 47 | 1.13 | 73 |

Footnotes for Table 2
$^a$compound dose-response curves were determined at 10 concentrations. Cells received a 24 hour exposure to test compounds before being washed (x3) with drug-free media. The IC50 (umol/L) values are the concentrations required to inhibit cell growth by 50% relative to untreated controls. Values are the average of 2-8 independent determinations (% CV < 20 in all cases).
$^b$Experiment performed entirely under oxic conditions.
$^c$The initial 4 hours of the 24 hour drug exposure was performed under anoxic conditions.
$^d$Hypoxic Cytotoxicity Ratio = fold change in intra-experimental IC50 for cells receiving 4 hours of anoxia relative to cells that received only oxic conditions.

All of the prodrugs (12, 13, 14, 15, 16, 17, 18, 19, 20 and 21) of Table 2 were significantly more potent at inhibiting the growth of all three cell lines after the cells received 4 hours of anoxia. The hypoxic cytotoxicity ratios (HCR) ranged from 8 to 96 in A431 cells, 14 to 89 in H1975 cells and 15 to 528 in SKOV3 cells, consistent with hypoxia-selective reduction of the 4-nitroimidazole reductive trigger, followed by trigger fragmentation to release an irreversible erbB1, 2, 4 inhibitor.

2.2. Cellular Enzyme Inhibitory Activities

The compounds 3, 5 and 6 were tested for their ability to inhibit the autophosphorylation of erbB1 (EGFR), and p44/42 MAPK (Erk1/2) in EGF-stimulated A431 cells by Western immunoblotting measurement of phospho-erbB1 and phospho-Erk1/2 status.

A431 cells were seeded into 6 well plates (with αMEM+5% FCS). The following day, plates were washed once with serum-free medium and grown for 18 hours in serum-free medium (αMEM) before being exposed to a range of inhibitor or prodrug concentrations for 1 hour and then stimulated for 15 minutes with 100 ng/ml epidermal growth factor (EGF receptor ligand). Next cells were washed with ice cold PBS and lysed in modified RIPA buffer on ice (30 min). Lysates were vortexed and clarify by spinning before protein concentrations of samples was determined by BCA assay. For western blot analysis 5 µg of total protein/well was loaded on a NuPAGE 4-12% gel and run at 150V (1 h) before transfer to 0.45 µm nitrocellulose membrane followed by blocking for 1 hr with 2% BSA in TBS-Tween 0.1%. All antibodies were diluted in 2% BSA TBS-Tween 0.1%. To detect phospho-EGFR (Tyr 1068) the monoclonal antibody (1:500; Cell Signalling #2234) was incubated overnight at 4° C. and binding was detected with goat-anti-Rabbit-IgG-HRP conjugated secondary antibody (1:5000; Santa Cruz #SC2054; 3 h RT). To detect downstream phospho-p44/42 MAPK(Erk 1/2) (Thr202/Tyr 204) the monoclonal antibody (Cell Signalling #4370) was used at a 1:500 dilution. The blot was then treated with Goat anti-rabbit IgG-HRP conjugated secondary antibody (Santa Cruz Biotechnology, Inc. sc-2054) for three hours at a ratio of 1:5000. To normalise for any inaccuracy in gel loading, each blot was probed with anti-β-actin antibody (Abacus ALS #MAB-1501R, 1:2000 dilution). The following day, the blot was treated with Goat anti-mouse IgG-HRP conjugated secondary antibody (Santa Cruz Biotechnology, Inc. sc-2055) for one hour at a 1:5000 ratio. Protein bands were visualized using Amersham ECL Plus Western Blotting Detection Reagent (GE Healthcare RPN2132). Densitometry was determined using Image J software. Values normalized to β-actin were plotted on SigmaPlot 11.0.

Figure 12:
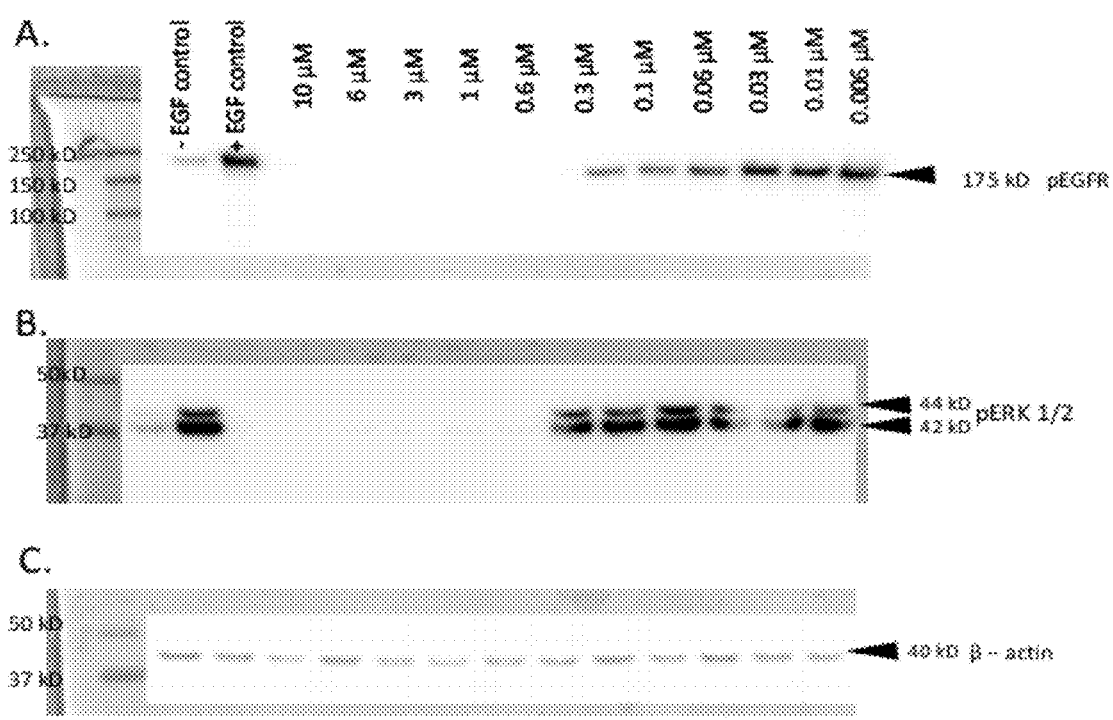
FIG. 12 shows inhibition of erbB1 (EGFR) autophosphorylation and p44/42 MAPK(Erk 1/2) phosphorylation in intact A431 cells following 1 hour treatment with a range of concentrations of compound 3.
Figure 13:
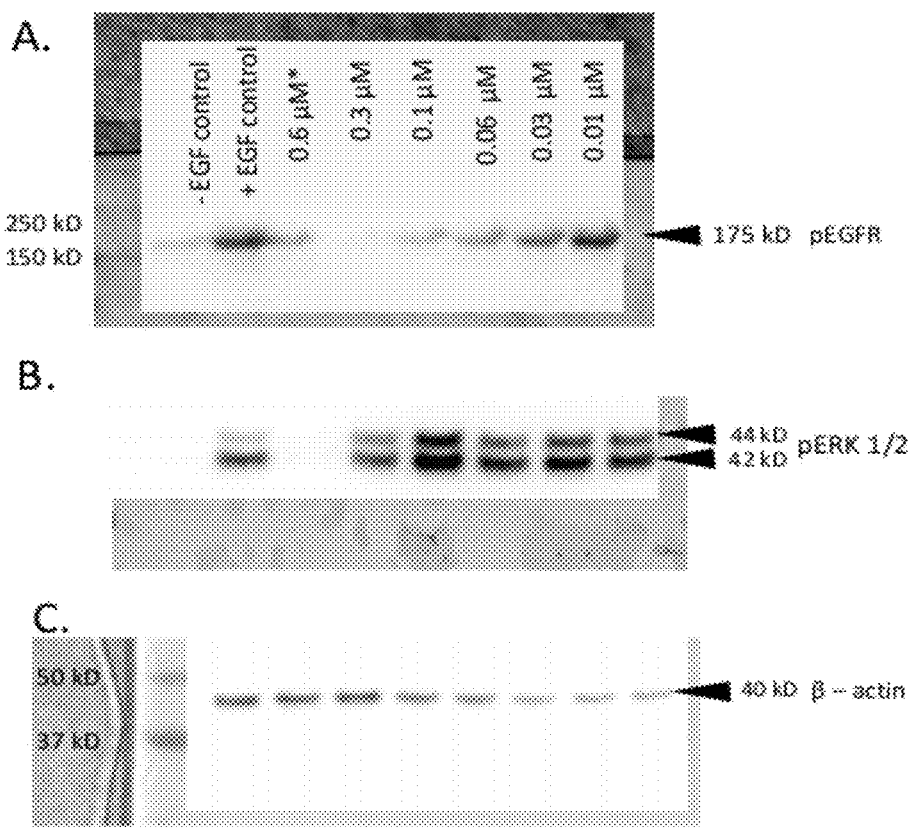
FIG. 13 shows inhibition of erbB1 (EGFR) autophosphorylation and p44/42 MAPK(Erk 1/2) phosphorylation in intact A431 cells following 1 hour treatment with a range of concentrations of compound 5.
Figure 14:
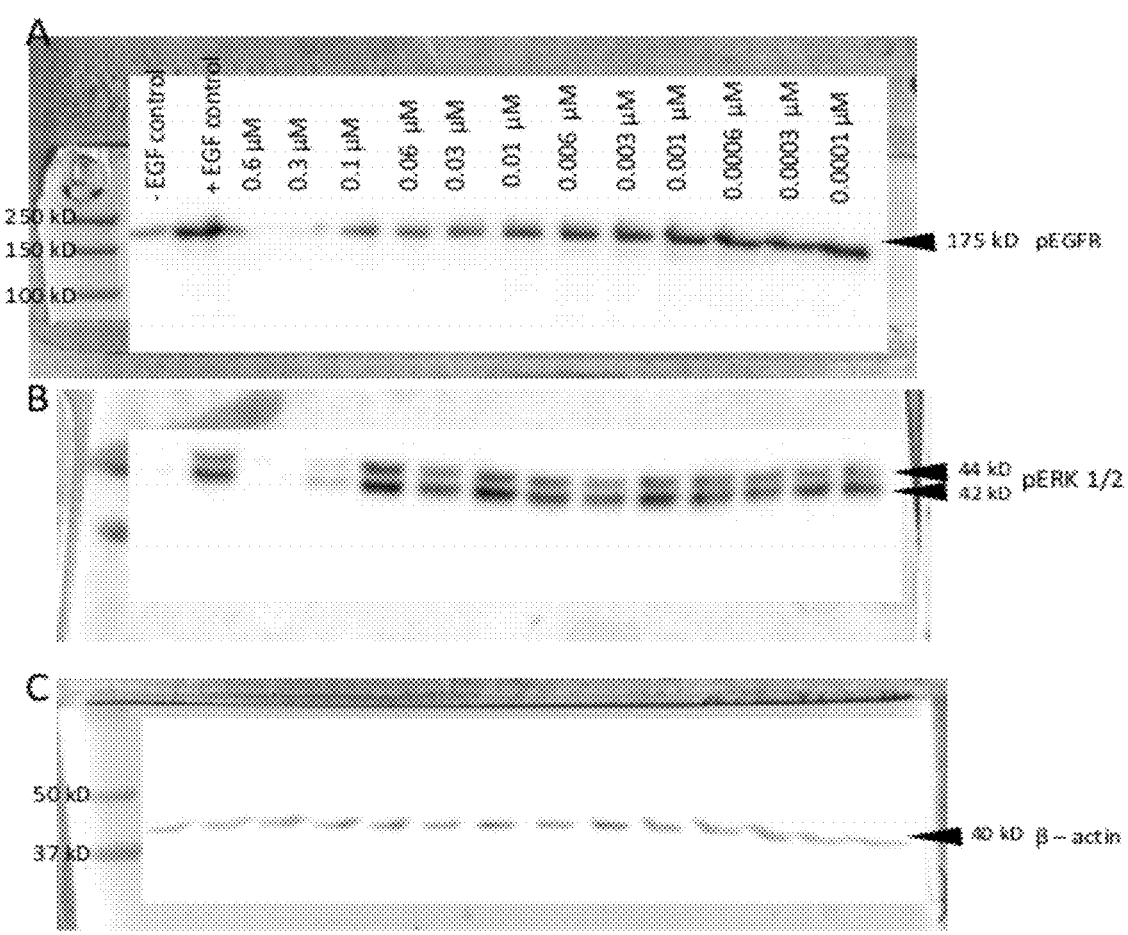
FIG. 14 shows inhibition of erbB1 (EGFR) autophosphorylation and p44/42 MAPK(Erk 1/2) phosphorylation in intact A431 cells following 1 hour treatment with a range of concentrations of compound 6.
Figure 15:
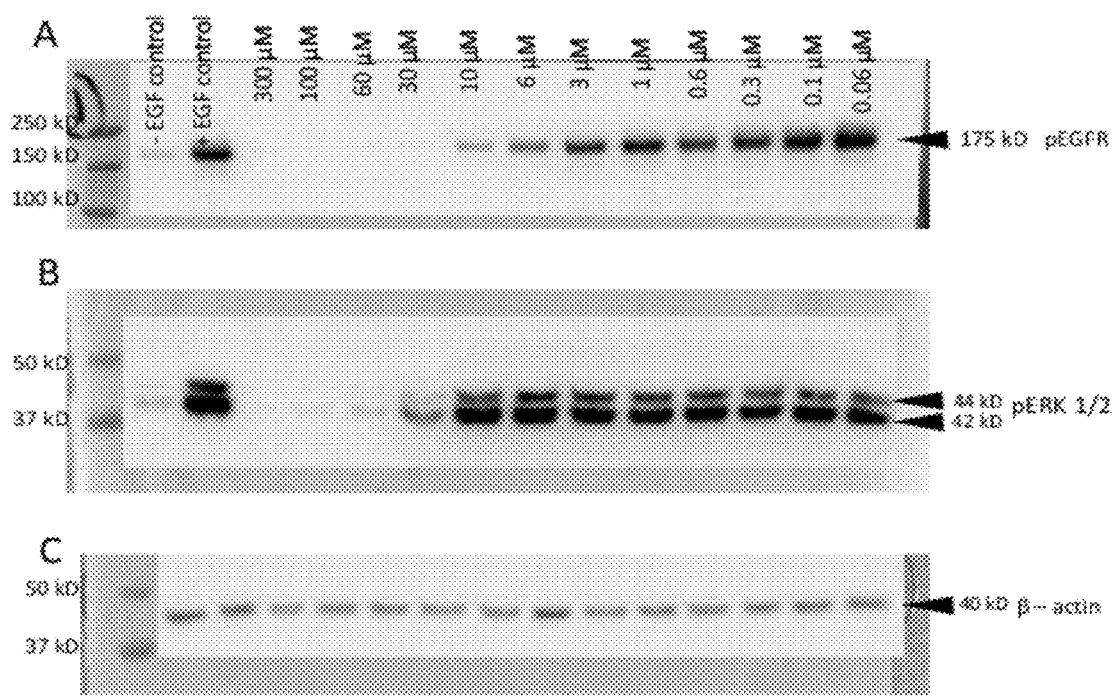
FIG. 15 shows inhibition of erbB1 (EGFR) autophosphorylation and p44/42 MAPK(Erk 1/2) phosphorylation in intact A431 cells following 1 hour treatment with a range of concentrations of prodrug 15.
Figure 16:
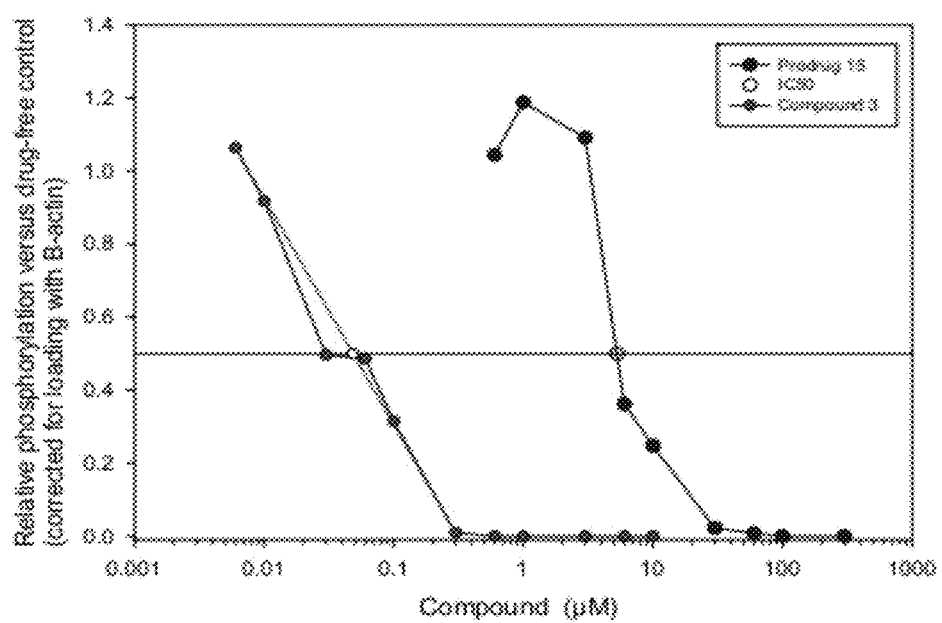
FIG. 16 is a graphical plot of band desitometry analysis of relative (β-actin corrected) inhibition of erbB1 (EGFR) autophosphorylation in intact A431 cells following 1 hour treatment with a range of concentrations of prodrug 15 and compound 3.

Compounds 3, 5 and 6 were shown to be potent inhibitors of cellular erbB1 (FIGS. 12A, 13A and 14A, respectively) with IC50s of 0.0483, 0.0395 and 0.0250 µM, respectively. In addition, suppression of EGFR phosphorylation in A431 cells was accompanied by coordinate loss of downstream p44/42 MAPK(Erk 1/2) phosphorylation (Thr202/Tyr 204) indicating modulation of the signalling network governed by EGFR activity (FIGS. 12B, 13B and 14B, respectively). In contrast the quaternary ammonium salt derivative prodrug 15 was 110-fold less effective (IC50 of 5.29 µM; FIG. 15A and FIG. 16) at inhibiting erbB1 autophosphorylation in intact A431 cells than its respective inhibitor, compound 3 (FIG. 12A). A similar loss of potency was observed for p44/42 MAPK(Erk 1/2) phosphorylation (Thr202/Tyr 204) (IC50 of 0.179 µM and 8.9 µM for compound 3 and prodrug 15, respectively (compare FIG. 12B and FIG. 15B) indicating less effective modulation of the downstream signalling network governed by EGFR activity. When the respective band densitometry values were plotted for the dose-dependent inhibition of phospho-EGFR (corrected for β-actin), it is evident that prodrug 15 is deactivated 110-fold relative to compound 3. This loss of cellular erbB1 inhibitory potency for the prodrugs is attributed primarily to cellular exclusion of the prodrugs due to the presence of a positively charged quaternary ammonium salt.

2.3 Radiolytic Reduction

Electron-affinic prodrugs can be selectively reduced by 1-electron processes in the hypoxic regions of solid tumours, in contrast to under normoxic conditions in normal tissues, to form or release a cytotoxic effector (Brown and Wilson, Nature Rev. Cancer, 2004, 4, 437-447). The prodrug should contain a trigger moiety possessing a 1-electron reduction potential, E(1), of between −0.6V to −0.2 V and preferably between −0.5 V to −0.3V vs. NHE. The E(1) values of many compounds can be obtained from the literature, (for example, Wardman, P. J. Phys. Chem. Ref. Data, 1989, 18, 1637-1755.) or determined by a number of methods. The pulse radiolysis method, for example, measures the equilibrium constant between the radical anions of the prodrugs, formed upon their 1-electron reduction, and reference standards such as viologen and quinone compounds, from which data the E(1) values of the compounds can be calculated. (Meisel and Czapski. J. Phys. Chem., 1975, 79, 1503-1509.) The E (1) values of prodrugs 13, 15-19 were measured by the pulse radiolysis method and determined to range between −0.428V and −0.417V (Table 3). All are considered to possess appropriate E(1) values to enable enzymatic formation of their radical anions in a biological context.

Prodrugs possessing appropriate E(1) values can be tested for their ability to release effector moieties by a number of methods, following the radiolysis of the prodrugs in solution. For example, mass spectrometry (MS) and/or high performance liquid chromatography (HPLC) before and after radiolysis identifies the starting compound and the products formed as a result of the radiolysis. Several 1-electron reductants can be produced upon the radiolysis of solutions containing different solutes. For example the $CO_2^{.-}$ radical, formed in γ-irradiated solutions containing formate ions, possesses a low E(1) of −1.90 V (Schwarz et al, Inorg. Chem., 1985, 24, 433-439.) and undergoes facile electron transfer to compounds of higher E(1). Under the radiation conditions employed, a concentration of 0.66 µM in 1-electron reducing equivalents (the $CO_2^{.-}$ radical) are produced per Gy (J kg$^{-1}$) of absorbed radiation dose. (Mulazzani et al, J. Phys. Chem., 1980, 90, 5347-5352.) By comparing the loss in prodrug concentration with the concentration of reducing equivalents produced upon the radiolysis of the solution, it is possible to determine whether one or multi-electron reduction is required for complete loss of each prodrug. Typically, evidence for 1-electron removal of a prodrug is sought after 0.95 reducing equivalents are transferred to the prodrug, to minimise multi-electron reduction of the same prodrug molecule. In the case of 1-electron removing a prodrug, this often indicates fragmentation of its radical anion. This conclusion is further supported by combined HPLC MS identification of the released cytotoxic effector and the products arising from the transient benzyl-type radical (e.g. the methyl nitroaromatic compound (MNA) formed by H-atom abstraction. This has been shown to occur in the case of certain related arylmethyl quaternary nitrogen mustards. (Anderson et al. J. Phys. Chem., 1997, 101, 9704-9709; Wilson et al. Radiat. Res., 1998, 149, 237-245.) The data obtained for prodrug 17 is consistent with its consumption at the 1-electron reduction level (>50% loss of prodrug at the 0.95 reducing equivalents level) with the released effector (compound 5) detected by HPLGMS, Table 3.

It is desirable that the reductive prodrugs are selected to have controlled fragmentation rate constants upon 1-electron reduction of the trigger moiety. Whilst fast fragmentation to release high concentrations of the cytotoxic effectors in the hypoxic regions of tumour cells is desirable, this is not so for normal tissue cells under normoxia. The rate constant of the back oxidation of the 1-electron reduced nitroarene-based prodrugs by oxygen, $kO_2$, which effectively inhibits the release of the effector, is given by the expression:—(Wardman et al, Biochem. Soc. Symp., 1995, 61, 171-194; Anderson et al, Org. Biomol. Chem. 2005, 3, 2167-2174.)

$$\log kO_2/M^{-1} s^{-1} = (4.6 \pm 0.1) - (5.0 \pm 0.2) \times E(1)C/C^-$$

where $E(1)C/C^-$ is the 1-electron reduction potential of the prodrug. This means, for over the preferred range in E (1), −0.5 V to −0.3 V, the pseudo $1^{st}$-order rate constants for this back oxidation in normal cells (which can be, under physiological conditions, as low as 10 μM in oxygen concentration) decrease from 130 s$^{-1}$ to 13 s$^{-1}$. Hence, over the preferred range in E(1) of the prodrug, the ranges in fragmentation rate to allow for sufficient back-oxidation in normoxic tissue and therefore to impart hypoxia-selective fragmentation to the prodrug (e.g. 5:1), is most preferably in the region of ca. 2-30 s$^{-1}$ for prodrugs in the upper range of desirable E(1) and ca. 20-300 s$^{-1}$ for prodrugs in the lower range of desirable E(1). The rate constants for fragmentation, kfrag, of the 1-electron reduced prodrugs can be measured using pulse radiolysis to observe the time-resolved formation of the absorption spectrum of the benzyl-type radical produced upon fragmentation of the radical anion. (Anderson et al, J. Phys. Chem. A, 1997, 101, 9704-9709.) The kfrag values of prodrugs 13, 15-17 were measured by pulse radiolysis and are presented in Table 3. All of the prodrugs possess fragmentation rates upon 1-electron reduction under hypoxia in the desirable range, consistent with them showing acceptable hypoxic cytotoxicity ratios (HCRs) in vitro in A431, H1975 and SKOV3 cell-based anti-proliferative assays (Table 3).

TABLE 3

Radiolytic reduction of selected prodrugs by the $CO_2^-$ radical.

| Prodrug | $E(1)/V^a$ | kfrag.$^b$/s$^{-1}$ | % Loss of prodrug$^c$ | Detection of NINA$^d$ |
|---|---|---|---|---|
| 13 | −0.417 | 60 ± 10 | | |
| 15 | −0.423 | 60 ± 10 | | |
| 16 | −0.418 | 60 ± 10 | | |
| 17 | −0.425 | 70 ± 10 | 70 | Yes |
| 18 | −0.428 | | | |
| 19 | −0.425 | | | |

Footnotes for Table 3
$^a$Determined against methylviologen, $E(1)MV^{2+}/MN^{+\cdot} = -447 \pm 7$ mV.
$^b$Pulse radiolysis data for the formation of the benzyl-type radicals absorbing in the 360-390 nm region.
$^c$Measurements made by HPLC-MS at 0.95 reducing equivalents; >50% indicates fragmentation upon 1-electron reduction.
$^d$Detection of methyl nitroaromatic (MNA) by HPLC-MS.

2.3.1 Radiolytic Reduction Experimental

The relative activities of example prodrugs in solution to release effectors, upon the introduction of reducing equivalents, were determined by the use of a $^{60}$Co γ-ray irradiator. Prodrugs were dissolved in Millipore water (containing added 50 mM sodium formate buffered at pH 7 by 5 mM sodium phosphate) at a concentration of 50 μM or below. Solutions, contained in air-tight glassware continuously saturated with $N_2O$ gas for 30 mins prior to radiolysis at a dose rate of 7.5 Gy min$^{-1}$, previously determined using Fricke dosimetry (Fricke and Hart, "Chemical Dosimetry" in *Radiation Dosimetry* Vol. 2, Attrix, F. H.; Roesch, W. C.; Tochilin, E. (Eds.), Academic Press, New York, 1966, pp 167-239.) Under the radiation conditions employed above, a concentration of 0.66 μM in 1-electron reducing equivalents (the $CO_2^-$ radical) are produced per Gy (Mulazzani et al, J. Phys. Chem., 90, 5347-5352, 1980.) and the prodrugs, (P), are reduced by electron transfer,

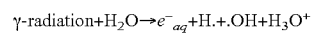

$$\gamma\text{-radiation} + H_2O \rightarrow e^-_{aq} + H\cdot + \cdot OH + H_3O^+$$

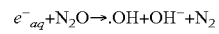

$$e^-_{aq} + N_2O \rightarrow \cdot OH + OH^- + N_2$$

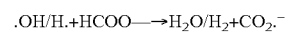

$$\cdot OH/H\cdot + HCOO^- \rightarrow H_2O/H_2 + CO_2^-$$

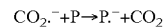

$$CO_2^- + P \rightarrow P\cdot^- + CO_2$$

The loss of prodrug 17 and formation of its effector 5 was monitored by HPLC-mass spectrophotometry (MS) in duplicate irradiated samples. The percentage loss in the concentration of the prodrugs and formation of the effectors at the 0.95 reducing equivalents level was determined. In addition, the detection of the methyl-nitroaromatic from prodrug 17 was recorded. Prodrugs exhibiting >50% loss in concentration at the 0.95 reducing equivalents level, indicate 1-electron stoichiometry.

Pulse radiolysis was used to monitor the 1-electron reduction and stability of the compounds in real time. A linear accelerator delivering short pulses of high energy electrons (2-3 Gy in 200 ns of 4 MeV) equipped with a fast spectophotometric detection system was used. (Anderson et al, J. Phys. Chem., A, 101, 9704-9709, 1997). Prodrugs were dissolved in NP-saturated solutions containing formate ions, as above, which, following pulse radiolysis, resulted in the rapid formation of the radical anions of the compounds within a few microseconds. The rate of fragmentation was determined by analysing kinetic transients at wavelengths corresponding to the formation of the benzyl-type radical of the trigger moiety. (Bays et al, J. Am. Chem. Soc., 105, 320-324, 1983; Anderson et al, J. Phys. Chem. A, 101, 9704-9709, 1997).

2.4 In vivo Efficacy of Compounds of the Invention

Methods

Specific pathogen-free female NIH-III nude mice, derived from breeding mice supplied by Charles River Laboratories (Wilmington, Mass.), were housed in groups of 4-6 in a temperature-controlled room (22±2° C.) with a 12-hour light/dark cycle and were fed ad libiturnwater and a standard rodent diet (Harlan Teklad diet 2018i). All animals were uniquely identifiable by ear tag number.

Freshly harvested cell suspensions were subcutaneously inoculated (100 μL) on the right flank with 5×10$^6$ H1975 or A431 cells in PBS. Mean tumour diameter was averaged from the longest diameter (length) multiplied by the perpendicular measurement (width). Tumour volume (mm$^3$) was calculated using the formula $(L \times w^2) \times \pi/6$ (where; L=length and w=width in mm of the carcinoma).

Growth Delay Experimental Procedure

Treatment was initiated when the turnouts reached a volume of approximately 250 mm³, as determined by calliper measurement. All drugs were given by intraperitoneal injection at dosing volumes of 10-20 ml/kg. Mice were dosed at the MID over a q3dx4, q5dx4 or q7dx4 schedule with tumour growth measured by callipers every 3-5 days over the 30-day duration of the study. Mice were culled if they developed signs of toxicity or if bodyweight loss exceeded 20% of starting weight. All animal experiments followed protocols approved by the Animal Ethics Committee of The University of Auckland.

Tumour bearing mice were assigned randomly to treatment groups when tumour diameter reached treatment size. Animals were rejected if xenografts show evidence of: (i) attachment to underlying muscle (due to risk of local invasion), (ii) signs of ulceration, or (iii) indolent tumour growth. Drug administration begins on the day of assignment.

During and after treatment, tumour size and body weights were measured regularly. Animals were culled if (i) the average diameter of the tumour exceeds 15 mm (survival endpoint), (ii) body weight loss exceeds 20% of pre-treatment value, (iii) there is evidence of prolonged or excessive morbidity, or (iv) tumour ulceration occurred. The experiment was terminated at day 21 (A431 tumours) or day 30 (H1975 tumours) after treatment initiation.

Efficacy Analysis

The time for individual tumours to increase in volume by 4 fold relative to treatment day-1 ($RTV^4$) was recorded. The median $RTV^4$ is calculated for each group and the difference in $RTV^4$ between control and treatment groups is described as the Tumour Growth Delay (TGD) in days. $RTV^4$ values normalise for any bias in tumour treatment volume on day 0.

Kaplan-Meier plots were constructed and median survival was calculated ($TTE_{50}$). The statistical significance of any differences in overall survival time taken to reach $RTV^4$ between treatment groups and control was analysed by Log Rank P statistical test.

Toxicity

Weight loss nadirs (time independent maxima) were recorded for each treatment group. Any signs of treatment related morbidity were documented. Acceptable toxicity was defined as no mean group weight loss of over 15% during the test, no individual weight loss over 20% and no individual weight loss over 10% in any 24 h period. All unscheduled deaths were recorded.

Results

Median tumour growth curves following treatment are presented in FIGS. 1-11. Summary tables of the effect of treatment on toxicity and efficacy are presented in Tables 4-6 below.

Overall, nine kinase inhibitors and nine prodrugs were administered to mice with human H1975 or A431 tumour xenografts. The mean (±SD) tumour volume at treatment initiation was 245 mm³±60 mm³ for H1975 tumours and 268 mm³±124 mm³ for A431 tumours.

At tolerated dose levels, all kinase inhibitors delayed tumour growth. This tumour growth delay was particularly significant for compounds 2-9 when administered at q3dx4 (P<0.05, log-rank test) in both H1975 (FIGS. 1-3) and A431 (FIG. 4) tumours. There was only minor bodyweight loss across all groups, although there was 1 death following treatment with compounds 5 and 7 in H1975 xenograft mice (Table 4).

TABLE 4

Summary of treatment toxicity and efficacy parameters for kinase inhibitors

| Compound | Dose[a] (μmol/kg) | Schedule | Cell line | N | Drug related deaths[b] | Weight Loss Nadir (%)[c] | TGD[d] | Log Rank[e] |
|---|---|---|---|---|---|---|---|---|
| 1 | 23.7 | q3dx4 | H1975 | 3 | 0 | −3.6 ± 3.0 | 12.5 | ns |
| 2 | 56.2 | q3dx4 | H1975 | 3 | 0 | −7.9 ± 0.6 | 100 | <0.05 |
| 3 | 100 | q3dx4 | H1975 | 3 | 0 | −4.7 ± 0.4 | 150 | <0.05 |
| 4 | 56.2 | q3dx4 | H1975 | 3 | 0 | −9.7 ± 4.0 | 188 | <0.05 |
| 5 | 75 | q3dx4 | H1975 | 3 | 1 | −8.5 ± 0.6 | 175 | <0.05 |
| 5 | 75 | q3dx4 | A431 | 3 | 0 | −6.3 ± 4.5 | >250 | <0.05 |
| 6 | 42.2 | q3dx4 | A431 | 3 | 0 | −1.5 ± 0.8 | >250 | <0.05 |
| 7 | 56.2 | q3dx4 | H1975 | 3 | 1 | −4.9 ± 2.4 | 156 | <0.05 |
| 8 | 100 | q3dx4 | H1975 | 3 | 0 | −3.3 ± 3.0 | 87.5 | <0.05 |
| 9 | 75 | q3dx4 | A431 | 3 | 0 | −1.7 ± 1.7 | >250 | <0.05 |

Footnotes for Table 4

[a]Administered in lactate buffer (pH 4) by intraperitoneal injection (<0.02 ml/g);

[b]all animal deaths considered likely to be drug related;

[c]Mean weight loss nadir (time independent maxima) relative to day 0 weight (%) for each individual;

[d]Tumour Growth Delay calculated as % increase in time required to reach 4 times initial treatment volume ($RTV^4$; relative to day 0 volume) relative to control growth;

[e]Kaplan-Meier Log Rank survival analysis of compound treated relative to buffer treated control assuming a survival endpoint of $RTV^4$.

Similarly, the prodrugs (compounds 12, 13, 15-21) all significantly delayed tumour growth in H1975 (FIG. 5-7) or A431 (FIG. 8) xenograft models after treatment at a q3dx4 schedule (P<0.05, log-rank test). Again, there was only minor bodyweight loss in the mice in all treatment groups, although there was 1 death following treatment with compound 19 (Table 5).

TABLE 5

Summary of treatment toxicity and efficacy parameters for prodrugs

| Compound | Dose[a] (μmol/kg) | Schedule | Cell line | N | Drug related deaths[b] | Weight Loss Nadir (%)[c] | TGD[d] | Log Rank[e] |
|---|---|---|---|---|---|---|---|---|
| 12 | 133 | q3dx4 | H1975 | 3 | 0 | −7.8 ± 0.6 | 87.5 | <0.05 |
| 13 | 75 | q3dx4 | H1975 | 3 | 0 | −4.1 ± 2.5 | 138 | <0.05 |
| 15 | 133 | q3dx4 | H1975 | 3 | 0 | −9.4 ± 3.3 | >250 | <0.05 |
| 16 | 100 | q3dx4 | H1975 | 3 | 0 | −10.1 ± 0.7 | 188 | <0.05 |
| 17 | 178 | q3dx4 | H1975 | 3 | 0 | −12.8 ± 2.3 | >275 | <0.05 |
| 17 | 178 | q3dx4 | A431 | 3 | 0 | −3.6 ± 1.8 | >250 | <0.05 |
| 18 | 178 | q3dx4 | A431 | 3 | 0 | −4.1 ± 0.4 | >250 | <0.05 |
| 19 | 75 | q3dx4 | H1975 | 4 | 1 | −2.7 ± 0.6 | 138 | <0.05 |
| 20 | 178 | q3dx4 | H1975 | 3 | 0 | −4.4 ± 2.3 | 150 | <0.05 |
| 21 | 178 | q3dx4 | A431 | 3 | 0 | −4.3 ± 2.3 | >250 | <0.05 |

Footnotes for Table 5
[a] Administered in lactate buffer (pH 4) by intraperitoneal injection (<0.02 ml/g);
[b] all animal deaths considered likely to be drug related;
[c] Mean weight loss nadir (time independent maxima) relative to day 0 weight (%) for each individual;
[d] Tumour Growth Delay calculated as % increase in time required to reach 4 times initial treatment volume ($RTV^4$; relative to day 0 volume) relative to control growth;
[e] Kaplan-Meier Log Rank survival analysis of compound treated relative to buffer treated control assuming a survival endpoint of $RTV^4$.

Figure 9:
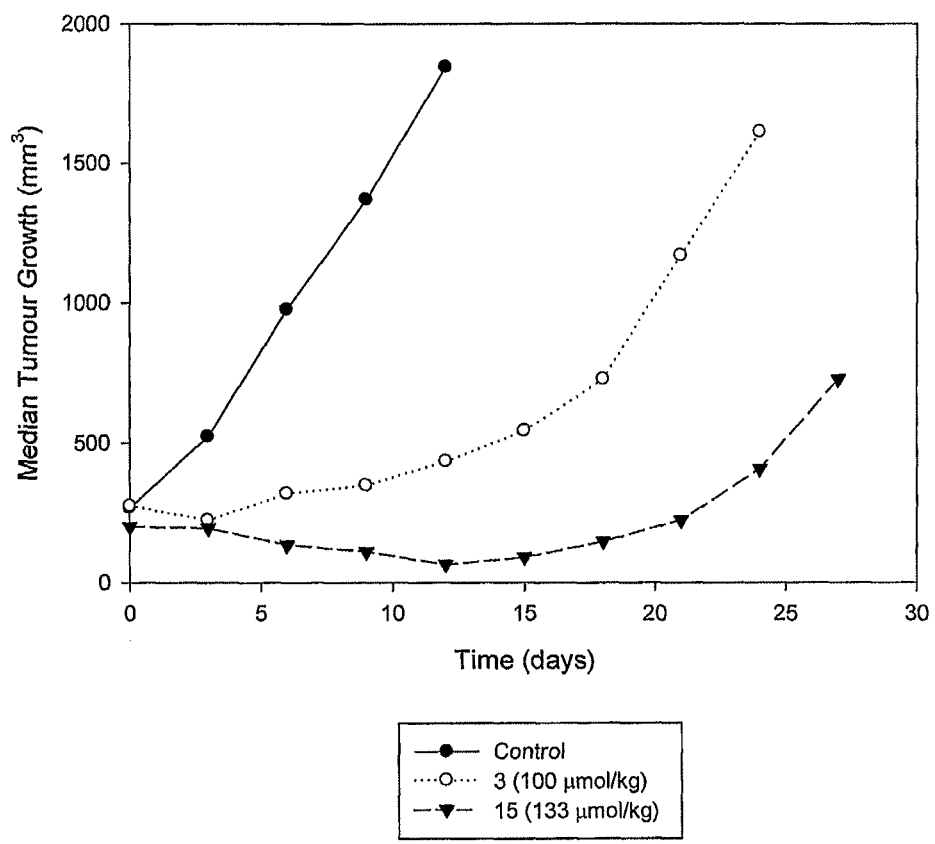
FIG. 9 shows median H1975 tumour growth after q3dx4 treatment with prodrug 15 and its cognate kinase inhibitor 3 (n=3)
Figure 10:
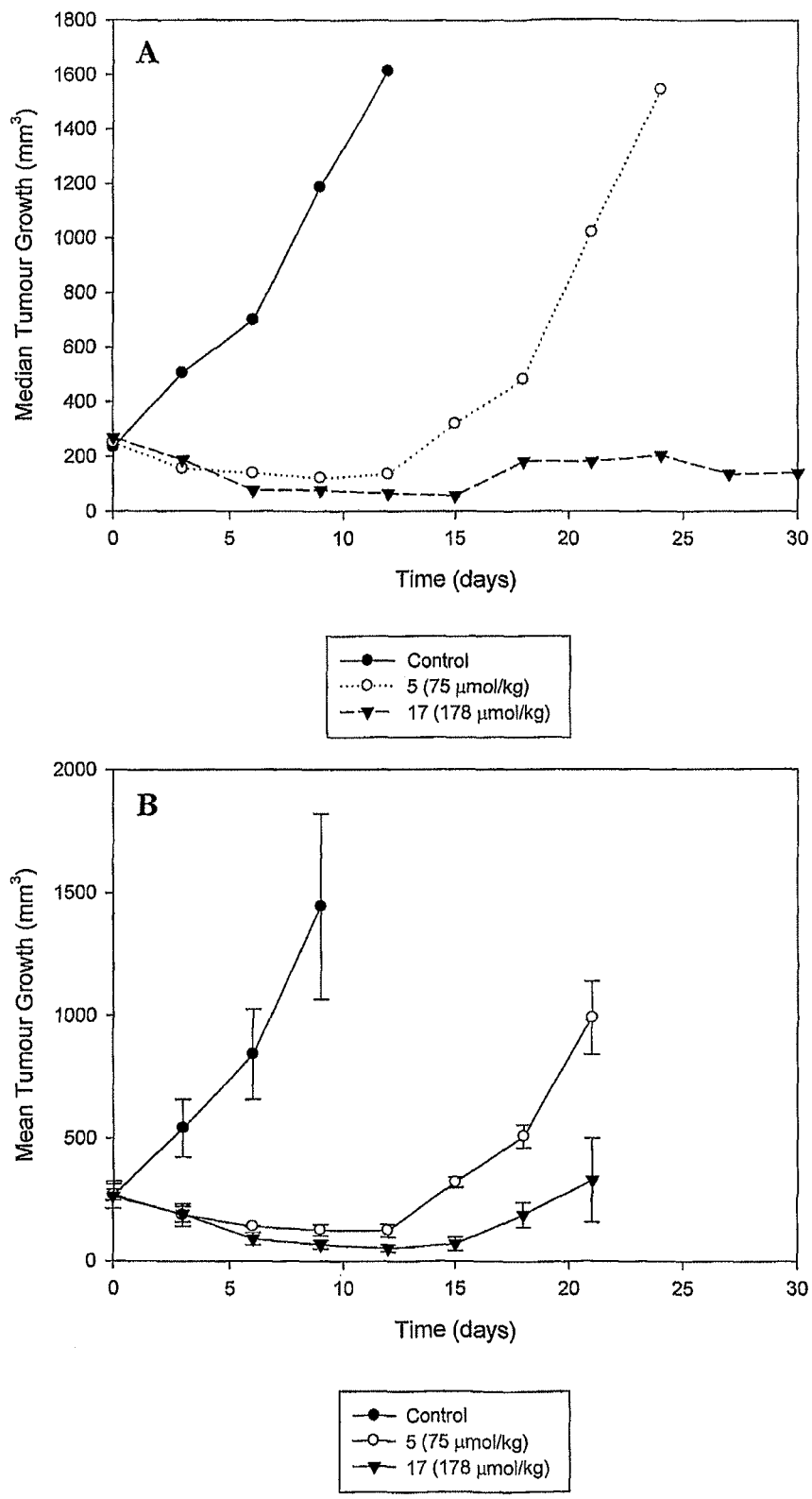
FIG. 10 shows median (A) and mean (B) H1975 tumour growth after q3dx4 treatment with prodrug 17 and its cognate kinase inhibitor 5 (n=3)

Administration of prodrugs 15 and 17, alongside their cognate kinase inhibitors, 3 and 5 respectively, revealed an extended period of growth delay in H1975 tumours for the prodrugs compared to the kinase inhibitors (FIGS. 9-10).

Figure 11:
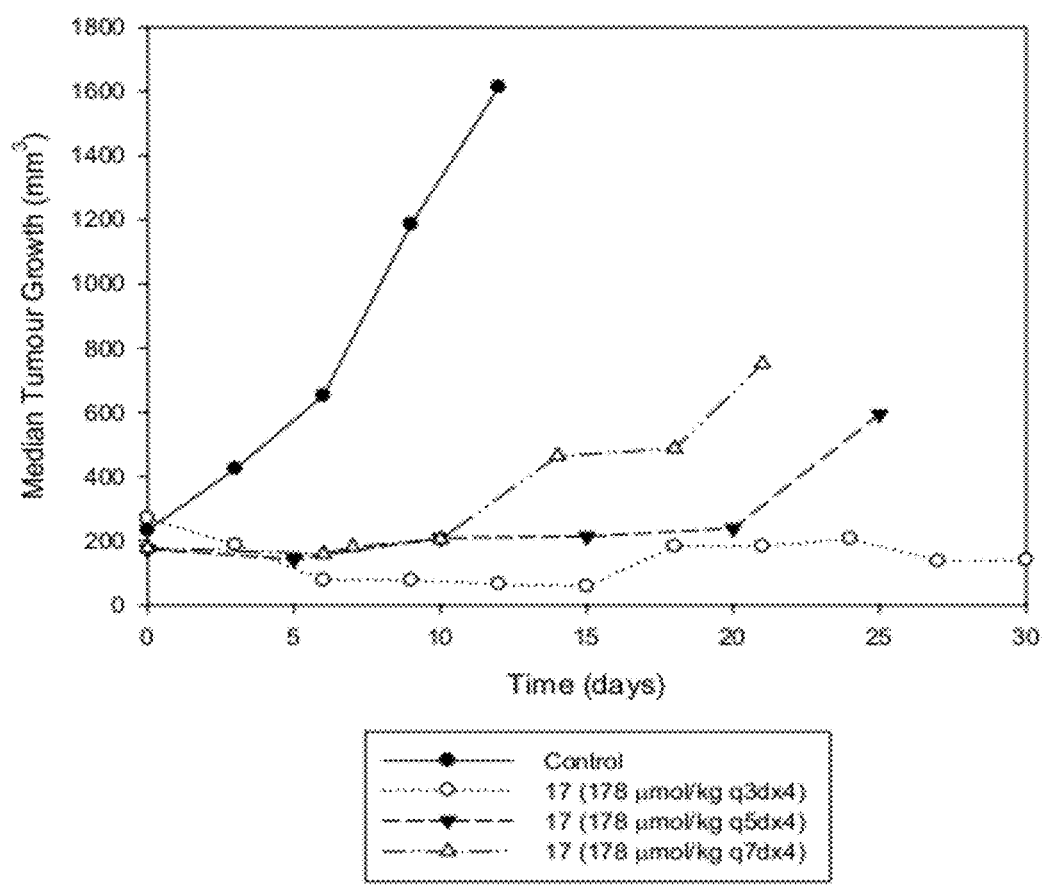
FIG. 11 shows median H1975 tumour growth after treatment with prodrug 17 at q3dx4, q5dx4 and q7dx4 dosing schedules (n=3)

Prodrug 17 was tested at multiple dosing schedules: q3dx4, q5c1×4 and q7dx4 at its q3dx4 MID. At all 3 dosing schedules, compound 17 significantly delayed tumour growth in H1975 tumours compared to controls (FIG. 11). There were no statistically significant differences in tumour growth between the 3 dosing schedules. Bodyweight loss was greatest after q3dx4 dosing and minimal after q7dx4 dosing (Table 6). However, 1 death was observed in the q7dx4 treatment group. It is not clear if this death was drug-related or not. Compound 17 was also administered at q3dx4 and q5c1×4 at its q3dx4 MTD to A431 xenograft mice, with both dosing schedules causing similar delays in A431 tumour growth and similar losses in animal bodyweight (Table 6).

Overall, the in vitro and in vivo activity data illustrate the effectiveness of the compounds of the invention as kinase inhibitors. The compounds are therefore suitable for use in kinase-inhibitory therapy. This is particularly the case with the reductive prodrugs and cancer therapy as tumours commonly have hypoxic regions. The prodrugs are reduced under hypoxia to release the parent kinase inhibitor and produce a tumour-targeted effect.

Prodrugs 15, 17 and 18 are considered particularly promising therapeutic candidates.

While the present invention is broadly as described above, those persons skilled in the art will appreciate that the specific description is illustrative only and that variations may be made without departing from the invention as defined in the following claims.

All publications referenced above are incorporated herein in their entirety.

TABLE 6

Summary of treatment toxicity and efficacy parameters for 17 at q3dx4, q5dx4 and q7dx4 schedules

| Compound | Dose[a] (μmol/kg) | Schedule | Cell line | N | Drug related deaths[b] | Weight Loss Nadir (%)[c] | TGD[d] | Log Rank[e] |
|---|---|---|---|---|---|---|---|---|
| 17 | 178 | Q3dx4 | H1975 | 3 | 0 | −12.8 ± 2.3 | >275 | <0.05 |
| 17 | 178 | Q5dx4 | H1975 | 3 | 0 | −7.6 ± 0.8 | 225 | <0.05 |
| 17 | 178 | Q7dx4 | H1975 | 3 | 1 | −1.9 ± 0.3 | 194 | <0.05 |
| 17 | 178 | Q3dx4 | A431 | 3 | 0 | −3.6 ± 1.8 | >250 | <0.05 |
| 17 | 178 | Q5dx4 | A431 | 3 | 0 | −4.6 ± 0.8 | >250 | <0.05 |

Footnotes for Table 6
[a] Administered in lactate buffer (pH 4) by intraperitoneal injection (<0.02 ml/g);
[b] all animal deaths considered likely to be drug related;
[c] Mean weight loss nadir (time independent maxima) relative to day 0 weight (%) for each individual;
[d] Tumour Growth Delay calculated as % increase in time required to reach 4 times initial treatment volume ($RTV^4$; relative to day 0 volume) relative to control growth;
[e] Kaplan-Meier Log Rank survival analysis of compound treated relative to buffer treated control assuming a survival endpoint of $RTV^4$.

The invention claimed is:
1. A compound of Formula III:

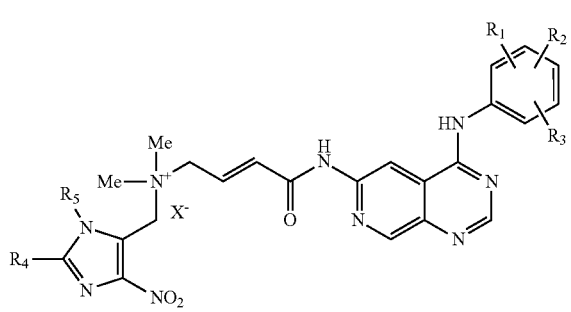

wherein:
X is a negatively charged counterion; and
either
(1) $R_1$ is H, and
 (a) $R_2$ is (3-chlorobenzyl)oxy-and $R_3$ is chloro;
 (b) $R_2$ and $R_3$, together with the carbon atoms to which they are attached, form 1-(3-fluorobenzyl)-1H-pyrazole;
 (c) $R_2$ is 2-pyridinylmethoxy and $R_3$ is chloro;
 (d) $R_2$ and $R_3$ are both chloro;
 (e) $R_2$ is chloro and $R_3$ is bromo;
 (f) $R_2$ and $R_3$ are both bromo;
 (g) $R_2$ is fluoro and $R_3$ is ethynyl;
 (h) $R_2$ is chloro and $R_3$ is ethynyl;
 (i) $R_2$ is bromo and $R_3$ is ethynyl;
 (j) other than when $R_2$ is in the 3-position in combination with $R_3$ in the 4-position, $R_2$ is bromo and $R_3$ is fluoro;
 (k) $R_2$ is 2-pyridinylmethoxy and $R_3$ is fluoro; or
 (l) $R_2$ is 2-pyridinylmethoxy and $R_3$ is bromo; or
(2) at least one of $R_1$, $R_2$ and $R_3$ is selected from the group consisting of benzyloxy, 3-chlorobenzyloxy and 2-pyridinylmethoxy and when at least one of $R_1$, $R_2$ and $R_3$ is not benzyloxy, 3-chlorobenzyloxy or 2-pyridinylmethoxy, each of the other of $R_1$, $R_2$ and $R_3$ is independently selected from the group consisting of H, halogen, and $C_2$-$C_4$ alkynyl, with the proviso that when one of $_1$, $R_2$ and $R_3$ is benzyloxy or 2-pyridinylmethoxy, the other two of $R_1$, $R_2$ and $R_3$ re not H; or
(3) two of $R_1$, $R_2$ and $R_3$, together with the carbon atoms to which they are attached, form 1-(3-fluorobenzyl)-1H-pyrazole, and the other of $R_1$, $R_2$ and $R_3$ is selected from the group consisting of H, halogen and $C_2$-$C_4$ alkynyl;
(4) two of $R_1$, $R_2$ and $R_3$, together with the carbon atoms to which they are attached, form 1-(3-fluorobenzyl)-1H-pyrazole, and the other of $R_1$, $R_2$ and $R_3$ is selected from the group consisting of H, halogen and $C_2$-$C_4$ alkynyl;
$R_4$ is selected from the group consisting of H, methyl, ethyl, trifluoromethyl, —CN, —CONH$_2$ and propyn-1-yl; and
$R_5$ is $C_1$-$C_6$ alkyl;
or a pharmaceutically acceptable salt or solvate thereof.
2. The compound according to claim 1, wherein
 (a) $R_1$ is H, and
 (b) $R_2$ is (3-chlorobenzyl)oxy and $R_3$ is chloro;
 (c) $R_2$ and $R_3$, together with the carbon atoms to which they are attached, form 1-(3-fluorobenzyl)-1H-pyrazole;
 (d) $R_2$ is 2-pyridinylmethoxy and $R_3$ is chloro;
 (e) $R_2$ and $R_3$ are both chloro;
 (f) $R_2$ is chloro and $R_3$ is bromo;
 (g) $R_2$ and $R_3$ are both bromo;
 (h) $R_2$ is fluoro and $R_3$ is ethynyl;
 (i) $R_2$ is chloro and $R_3$ is ethynyl;
 (j) $R_2$ is bromo and $R_3$ is ethynyl;
 (k) other than when $R_2$ is in the 3-position in combination with $R_3$ in the 4-position, $R_2$ is bromo and $R_3$ is fluoro;
 (l) $R_2$ is 2-pyridinylmethoxy and $R_3$ is fluoro; or
 (m) $R_2$ is 2-pyridinylmethoxy and $R_3$ is bromo.
3. The compound according to claim 1, wherein at least one of $R_1$, $R_2$ and $R_3$ is selected from the group consisting of benzyloxy, 3-chlorobenzyloxy and 2-pyridinylmethoxy and when at least one of $R_1$, $R_2$ and $R_3$ is not benzyloxy, 3-chlorobenzyloxy or 2-pyridinylmethoxy, each of the other of $R_1$, $R_2$ and $R_3$ is independently selected from the group consisting of H, halogen, and $C_2$-$C_4$ alkynyl, with the proviso that when one of $R_1$, $R_2$ and $R_3$ is benzyloxy or 2-pyridinylmethoxy, the other two of $R_1$, $R_2$ and $R_3$ are not H.
4. The compound according to claim 1, wherein two of $R_1$, $R_2$ and $R_3$, together with the carbon atoms to which they are attached, form 1-(3-fluorobenzyl)-1H-pyrazole, and the other of $R_1$, $R_2$ and $R_3$ is selected from the group consisting of H, halogen and $C_2$-$C_4$ alkynyl.
5. The compound according to claim 1, wherein $R_5$ is selected from the group consisting of methyl, ethyl, and propyl.
6. The compound according to claim 5, wherein $R_4$ is H.
7. The compound according to claim 5, wherein $R_4$ is H and $R_5$ is methyl.
8. The compound according to claim 1, wherein the compound has Formula IIIA

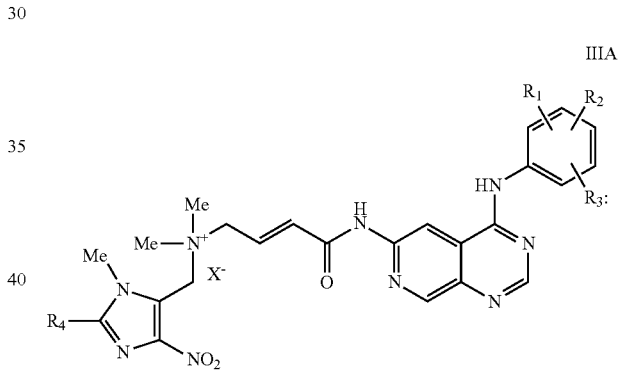

wherein X, $R_1$, $R_2$ and $R_3$ are defined for Formula III in claim 1 and $R_4$ is selected from the group consisting of H, methyl, ethyl, trifluoromethyl, —CN, —CONH2 and propyn-1-yl.
9. The compound according to claim 1, wherein the prodrug is a compound or Formula IIIB

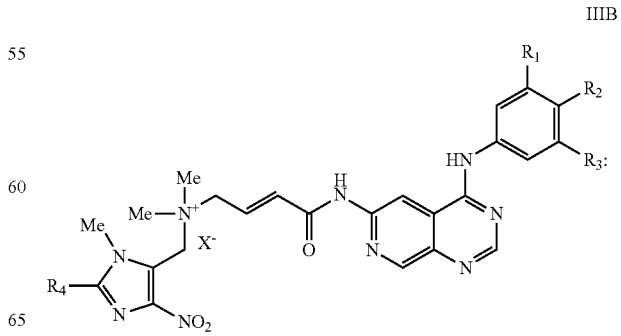

wherein X, R₁, R₂ and R₃ are as defined in claim 2 and R₄ is selected from the group consisting of H, methyl, ethyl, trifluoromethyl, —CN, —CONH2 and propyn-1-yl.

10. The compound according to claim 9, wherein:
R₁ is H, and either
R₂ is (3-chlorobenzyl)oxy- and R₃ is chloro;
R₂ and R₃, together with the carbon atoms to which they are attached, form 1-(3-fluorobenzyl)-1H-pyrazole;
R₂ is 2-pyridinylmethoxy and R₃ is chloro;
R₂ and R₃ are both chloro;
R₂ is chloro and R₃ is bromo;
R₂ is bromo and R₃ is chloro
R₂ and R₃ are both bromo;
R₂ is fluoro and R₃ is ethynyl;
R₂ is chloro and R₃ is ethynyl;
R₂ is bromo and R₃ is ethynyl;
R₂ is bromo and R₃ is fluoro;
R₂ is 2-pyridinylmethoxy and R₃ is fluoro; or
R₂ is 2-pyridinylmethoxy and R₃ is bromo.

11. The compound according to claim 9, wherein R₄ is H.

12. The compound according to claim 1, selected from the group consisting of:
- (2E)-4-[(4-{3-chloro-4-[(3-chlorobenzyl)oxy]anilino}pyrido[3,4-d]pyrimidin-6-yl)amino]-N,N-dimethyl-N-[(1-methyl-4-nitro-1H-imidazol-5-yl)methyl]-4-oxo-2-buten-1-ammonium bromide,
- (2E)-4-[(4-{[1-(3-fluorobenzyl)-1H-indazol-5-yl]amino]pyrido[3,4-d]pyrimidin-6-yl)amino}-N,N-dimethyl-N-[(1-methyl-4-nitro-1H-imidazol-5-yl)methyl]-4-oxo-2-buten-1-ammonium bromide,
- (2E)-N-[(1,2-dimethyl-4-nitro-1H-imidazol-5-yl)methyl]-4-[(4-{[1-(3-fluorobenzyl)-1H-indazol-5-yl]amino]pyrido[3,4-d]pyrimidin-6-yl)amino}-N,N-dimethyl-4-oxo-2-buten-1-ammonium bromide,
- (2E)-4-({4-[3-chloro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide,
- (2E)-4-{[4-(3,4-dichloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-{[4-(3,4-dibromoanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-{[4-(3-ethynyl-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-{[4-(4-chloro-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide,
- (2E)-4-[(4-{3-chloro-4-[(3-chlorobenzyl)oxy]anilino}pyrido[3,4-d]pyrimidin-6-yl)amino]-N-[(1,2-dimethyl-4-nitro-1H-imidazol-5-yl)methyl]-N,N-dimethyl-4-oxo-2-buten-1-ammonium bromide,
- (2E)-4-[(4-{3-chloro-4-[(3-chlorobenzyl)oxy]anilino}pyrido[3,4-d]pyrimidin-6-yl)amino]-N-[(2-ethyl-1-methyl-4-nitro-1H-imidazol-5-yl)methyl]-N,N-dimethyl-4-oxo-2-buten-1-ammonium bromide,
- (2E)-4-[(4-{3-chloro-4-[(3-chlorobenzyl)oxy]anilino}pyrido[3,4-d]pyrimidin-6-yl)amino]-N,N-dimethyl-N-{[1-methyl-4-nitro-2-(trifluoromethyl)-1H-imidazol-5-yl]methyl}-4-oxo-2-buten-1-ammonium bromide,
- (2E)-4-[(4-{3-chloro-4-[(3-chlorobenzyl)oxy]anilino}pyrido[3,4-d]pyrimidin-6-yl)amino]-N-[(2-cyano-1-methyl-4-nitro-1H-imidazol-5-yl)methyl]-N,N-dimethyl-4-oxo-2-buten-1-ammonium bromide,
- (2E)-N-{[2-(aminocarbonyl)-1-methyl-4-nitro-1H-imidazol-5-yl]methyl}-4-[(4-{3-chloro-4-[(3-chlorobenzyl)oxy]anilino}pyrido[3,4-d]pyrimidin-6-yl)amino]-N,N-dimethyl-4-oxo-2-buten-1-ammonium bromide,
- (2E)-4-[(4-{3-chloro-4-[(3-chlorobenzyl)oxy]anilino}pyrido[3,4-d]pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide,
- (2E)-N-[(2-ethyl-1-methyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide,
- (2E)-4-[(4-{[1-(3-fluorobenzyl)-1H-indazol-5-yl]amino}pyrido[3,4-d]pyrimidin-6-yl)amino]-N,N-dimethyl-N-{[1-methyl-4-nitro-2-(trifluoromethyl)-1H-imidazol-5-yl]methyl}-4-oxo-2-buten-1-ammonium bromide,
- (2E)-N-[(2-cyano-1-methyl-4-nitro-1H-imidazol-5-yl)methyl]-4-[(4-{[1-(3-fluorobenzyl)-1 H-indazol-5-yl]amino}pyrido[3,4-d]pyrimidin-6-yl)amino]-N,N-dimethyl-4-oxo-2-buten-1-ammonium bromide,
- (2E)-N-{[2-(aminocarbonyl)-1-methyl-4-nitro-1H-imidazol-5-yl]methyl}-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide,
- (2E)-4-[(4-{[1-(3-fluorobenzyl)-1H-indazol-5-yl]amino}pyrido[3,4-d]pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide,
- (2E)-4-({4-[3-chloro-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide,
- (2E)-4-({4-[3-chloro-4-(2-pyridinylmethoxy)anilino]pyrido[3,4-d]pyrimidin-6-yl}amino)-N-[(2-ethyl-1-methyl-4-nitro-1H-imidazol-5-yl)methyl]-N,N-dimethyl-4-oxo-2-buten-1-ammonium bromide,
- (2E)-4-({4-[3-chloro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide,
- (2E)-4-({4-[3-chloro-4-(2-pyridinylmethoxy)anilino]pyrido[3,4-d]pyrimidin-6-yl}amino)-N-[(2-cyano-1-methyl-4-nitro-1H-imidazol-5-yl)methyl]-N,N-dimethyl-4-oxo-2-buten-1-ammonium bromide,
- (2E)-N-{[2-(aminocarbonyl)-1-methyl-4-nitro-1H-imidazol-5-yl]methyl}-4-({4-[3-chloro-4-(2-pyridinylmethoxy)anilino]pyrido[3,4-d]pyrimidin-6-yl}amino)-N,N-dimethyl-4-oxo-2-buten-1-ammonium bromide,
- (2E)-4-({4-[3-chloro-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide, (2E)-4-{[4-(3,4-dichloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(3,4-dichloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(3,4-dichloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-N-[(2-cyano-1-methyl-4-nitro-1H-imidazol-5-yl)methyl]-4-{[4-(3,4-dichloroanilino)pyrido[3,4-d]pyrimidin-6-yl]amino}-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(3,4-dichloroanilino)pyrido[3,4-d]pyrimidin-6-yl]amino}-N,N-dimethyl-4-oxo-2-buten-1-ammonium bromide, (2E)-4-{[4-(3,4-dichloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(3-bromo-4-chloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(3-bromo-4-chloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(3-bromo-4-chloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-4-{[4-(3-bromo-4-chloroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(3-bromo-4-chloroanilino)pyrido[3,4-d]pyrimidin-6-yl]amino}-N,N-dimethyl-4-oxo-2-buten-1-ammonium bromide, (2E)-4-{[4-(3-bromo-4-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(4-bromo-3-chloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(4-bromo-3-chloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(4-bromo-3-chloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-4-{[4-(4-bromo-3-chloroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(4-bromo-3-chloroanilino)pyrido[3,4-d]pyrimidin-6-yl]amino}-N,N-dimethyl-4-oxo-2-buten-1-ammonium bromide, (2E)-4-{[4-(4-bromo-3-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(3,4-dibromoanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(3,4-dibromoanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(3,4-dibromoanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-N-[(2-cyano-1-methyl-4-nitro-1H-imidazol-5-yl)methyl]-4-{[4-(3,4-dibromoanilino)pyrido[3,4-d]pyrimidin-6-yl]amino}-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(3,4-dibromoanilino)pyrido[3,4-d]pyrimidin-6-yl]amino}-N,N-dimethyl-4-oxo-2-buten-1-ammonium bromide, (2E)-4-{[4-(3,4-dibromoanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-N-[(1,2-dimethyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide, (2E)-N-[(2-ethyl-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide, (2E)-4-{[4-(3-ethynyl-4-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-N-[(2-cyano-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(3-ethynyl-4-fluoroanilino)pyrido[3,4-d]pyrimidin-6-yl]amino}-N,N-dimethyl-4-oxo-2-buten-1-ammonium bromide, (2E)-4-{[4-(3-ethynyl-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(4-chloro-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(4-chloro-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(4-chloro-3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-4-{[4-(4-chloro-3-ethynylanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(4-chloro-3-ethynylanilino)pyrido[3,4-d]pyrimidin-6-yl]amino}-N,N-dimethyl-4-oxo-2-buten-1-ammonium bromide, (2E)-4-{[4-(4-chloro-3-ethynylanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(4-bromo-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide, (2E)-4-{[4-(4-bromo-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(4-bromo-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(4-bromo-3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-4-{[4-(4-bromo-3-ethynylanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(4-bromo-3-ethynylanilino)pyrido[3,4-d]pyrimidin-6-yl]amino}-N,N-dimethyl-4-oxo-2-buten-1-ammonium bromide, (2E)-4-{[4-(4-bromo-3-ethynylanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-{[4-(4-bromo-3-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide, (2E)-4-{[4-(4-bromo-3-fluoroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide, (2E)-4-{[4-(4-bromo-3-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide, (2E)-4-{[4-(4-bromo-3-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide, (2E)-4-{[4-(4-bromo-3-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-{[4-(4-bromo-3-fluoroanilino)pyrido[3,4-d]pyrimidin-6-yl]amino}-N,N-dimethyl-4-oxo-2-buten-1-ammonium bromide, (2E)-4-{[4-(4-bromo-3-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide, (2E)-4-({4-[3-fluoro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide, (2E)-N-[(1,2-dimethyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide, (2E)-N-[(2-ethyl-1-methyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide, (2E)-4-({4-[3-fluoro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide, (2E)-N-[(2-cyano-1-methyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide, (2E)-N-{[2-(aminocarbonyl)-1-methyl-4-nitro-1H-imidazol-5-yl]methyl}-4-({4-[3-fluoro-4-(2--pyridinylmethoxy)anilino]pyrido[3,4-d]pyrimidin-6-yl}amino)-N,N-dimethyl-4-oxo-2-buten-1-ammonium bromide, (2E)-4-({4-[3-fluoro-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide, (2E)-4-({4-[3-bromo-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide, (2E)-4-({4-[3-bromo-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide, (2E)-4-({4-[3-bromo-4-(2-pyridinylmethoxy)anilino]pyrido[3,4-d]pyrimidin-6-yl}amino)-N-[(2-ethyl-1-methyl-4-nitro-1H-imidazol-5-yl)methyl]-N,N-dimethyl-4-oxo-2-buten-1-ammonium bromide, (2E)-4-({4-[3-bromo-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide, (2E)-4-({4-[3-bromo-4-(2-pyridinylmethoxy)anilino]pyrido[3,4-d]pyrimidin-6-yl}amino)-N-[(2-cyano-1-methyl-4-nitro-1H-imidazol-5-yl)methyl]-N,N-dimethyl-4-oxo-2-buten-1-ammonium bromide, (2E)-N-{[2-(aminocarbonyl)-1-methyl-4-nitro-1H-imidazol-5-yl]methyl}-4-({4-[3-bromo-4-(2-pyridinylmethoxy)anilino]pyrido[3,4-d]pyrimidin-6-yl}amino)-N,N-dimethyl-4-oxo-2-buten-1-ammonium bromide and (2E)-4-({4-[3-bromo-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide;

and pharmaceutically acceptable salts and solvates thereof.

13. The compound according to claim 12, which is (2E)-4-({4-[3-chloro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (15), or a pharmaceutically acceptable salt thereof.

14. The compound according to claim 12, which is (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide, or a pharmaceutically acceptable salt thereof.

15. The compound according to claim 12, which is (2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide, or a pharmaceutically acceptable salt thereof.

16. A pharmaceutical composition comprising a compound according to claim 1, in combination with one or more pharmaceutically acceptable excipients.

17. A method of inhibiting kinase activity within a subject, comprising the step of administering an inhibitory amount of a compound according to claim 1 to a subject in need of such treatment.

* * * * *